(12) United States Patent
Demaster et al.

(10) Patent No.: US 11,582,979 B2
(45) Date of Patent: Feb. 21, 2023

(54) SELECTIVELY TREATING PLANT ITEMS

(71) Applicant: COMESTAAG LLC, Osceola, WI (US)

(72) Inventors: Andrew A. Demaster, Pacific Grove, CA (US); T. Howard Killilea, North Oaks, MN (US); Rachel E. Demaster, Pacific Grove, CA (US)

(73) Assignee: ComestaAg LLC, Fargo, ND (US)

( * ) Notice: Subject to any disclaimer, the term of this patent is extended or adjusted under 35 U.S.C. 154(b) by 0 days.

(21) Appl. No.: 17/545,969

(22) Filed: Dec. 8, 2021

(65) Prior Publication Data
US 2022/0095638 A1 Mar. 31, 2022

Related U.S. Application Data

(63) Continuation-in-part of application No. PCT/US2021/036202, filed on Jun. 7, 2021.
(Continued)

(51) Int. Cl.
*A23B 7/16* (2006.01)
*A23L 19/00* (2016.01)
(Continued)

(52) U.S. Cl.
CPC .............. *A23B 7/16* (2013.01); *A23B 7/154* (2013.01); *A23B 7/158* (2013.01); *A23L 19/05* (2016.08);
(Continued)

(58) Field of Classification Search
CPC .......... A23B 7/16; A23B 7/154; A23B 7/158; A23L 19/05; G01N 33/025; A23V 2002/00
(Continued)

(56) References Cited

U.S. PATENT DOCUMENTS 2,404,373 A * 7/1946 Harlow
4,335,145 A * 6/1982 Stanley
(Continued)

FOREIGN PATENT DOCUMENTS

EP 1 107 000 B1 11/2005
EP 3 476 216 A1 5/2019
(Continued)

OTHER PUBLICATIONS

Hagenmaier et al. 1992 "Gas Permeability of Fruit Coating Waxes", J. Amer.Soc.Hort.Sci.117(1):105-109. (Year: 1992).*
(Continued)

*Primary Examiner* — Helen F Heggestad
(74) *Attorney, Agent, or Firm* — Merchant & Gould P.C.

(57) ABSTRACT

Methods and systems for selectively applying a treatment to a plant item is provided. The method may include conveying, in an industrial processing line, at least one plant item in the batch of plant items to a sensing region having one or more sensors, assessing, with the one or more sensors and a computing device, one or more properties of the at least one plant item associated with ripeness and/or another attribute, conveying the at least one plant item to a treatment region, determining a treatment to apply to the at least one plant item based on the assessed one or more properties; and applying, in the treatment region, the treatment to the at least one plant item.

27 Claims, 6 Drawing Sheets

Related U.S. Application Data

(60) Provisional application No. 63/195,147, filed on May 31, 2021, provisional application No. 63/065,484, filed on Aug. 13, 2020, provisional application No. 63/045,155, filed on Jun. 28, 2020, provisional application No. 63/035,818, filed on Jun. 7, 2020.

(51) Int. Cl.
*A23B 7/154* (2006.01)
*A23B 7/158* (2006.01)
*G01N 33/02* (2006.01)

(52) U.S. Cl.
CPC ........ *G01N 33/025* (2013.01); *A23V 2002/00* (2013.01)

(58) Field of Classification Search
USPC ........ 426/231, 289, 293, 302, 308, 506, 615
See application file for complete search history.

(56) References Cited

U.S. PATENT DOCUMENTS

| | | | |
|---|---|---|---|
| 4,726,898 A | 2/1988 | Mills et al. | |
| 4,959,230 A | 9/1990 | Wyss et al. | |
| 5,019,403 A | 5/1991 | Krochta | |
| 5,101,763 A * | 4/1992 | Creason et al. | |
| 5,315,879 A | 5/1994 | Crochon et al. | |
| 5,376,391 A | 12/1994 | Nisperos-Carriedo et al. | |
| 5,489,442 A | 2/1996 | Dunn et al. | |
| 6,068,867 A | 5/2000 | Nussinovitch et al. | |
| 6,313,068 B1 | 11/2001 | Daly et al. | |
| 6,401,913 B1 | 6/2002 | Blanc | |
| 6,482,455 B1 | 11/2002 | Freire et al. | |
| 6,539,781 B1 | 4/2003 | Crezee | |
| 6,655,878 B1 | 12/2003 | de Vos et al. | |
| 6,742,647 B2 | 6/2004 | De Greef | |
| 6,847,447 B2 | 1/2005 | Ozanich | |
| 7,228,958 B2 | 6/2007 | Hendrik De Greef | |
| 7,267,743 B2 | 9/2007 | Borsinger et al. | |
| 7,708,822 B2 | 5/2010 | Lahav et al. | |
| 7,776,928 B2 | 8/2010 | Borsinger et al. | |
| 8,061,501 B2 | 11/2011 | Benedetti | |
| 8,424,243 B1 | 4/2013 | Narciso et al. | |
| 8,752,328 B2 | 6/2014 | Kaiser et al. | |
| 9,044,045 B2 | 6/2015 | Brown et al. | |
| 9,073,707 B2 | 7/2015 | Ruissen et al. | |
| 9,163,151 B2 | 10/2015 | Lock et al. | |
| 9,283,173 B2 | 3/2016 | Lederman | |
| 9,363,880 B2 | 6/2016 | Keener et al. | |
| 9,475,643 B1 | 10/2016 | Odman et al. | |
| 9,568,438 B1 | 2/2017 | Kim et al. | |
| 9,648,890 B2 | 5/2017 | Nussinovitch et al. | |
| 9,739,737 B2 | 8/2017 | Swager et al. | |
| 9,789,518 B2 | 10/2017 | Iino | |
| 9,919,345 B1 | 3/2018 | Lu et al. | |
| 10,194,672 B2 | 2/2019 | Keener et al. | |
| 10,253,208 B2 | 4/2019 | Alcantar et al. | |
| 10,271,561 B2 | 4/2019 | Omenetto et al. | |
| 10,330,531 B2 | 6/2019 | Goldring et al. | |
| 10,408,748 B2 | 9/2019 | Schwartzer et al. | |
| 10,421,103 B2 | 9/2019 | Benedetti | |
| 10,481,589 B1 | 11/2019 | Drouillard | |
| 10,502,679 B2 | 12/2019 | Aphek | |
| 10,537,130 B2 | 1/2020 | Rogers | |
| 2005/0122524 A1 | 6/2005 | Ibarra et al. | |
| 2006/0037892 A1 | 2/2006 | Blanc | |
| 2014/0147015 A1 | 5/2014 | Bajema et al. | |
| 2014/0308402 A1 | 10/2014 | Girard | |
| 2016/0231267 A1 | 8/2016 | Swager et al. | |
| 2016/0324174 A1 | 11/2016 | Rojas Graü et al. | |
| 2016/0349230 A1 | 12/2016 | Kirkjan | |
| 2017/0156356 A1 | 6/2017 | Omenetto et al. | |
| 2017/0292908 A1 | 10/2017 | Wilk et al. | |
| 2018/0317539 A1 | 11/2018 | Nabeiro | |
| 2019/0217341 A1 | 7/2019 | Nijland | |
| 2019/0281844 A1 | 9/2019 | Vergara Salinas et al. | |
| 2019/0285577 A1 | 9/2019 | Swager et al. | |
| 2019/0340749 A1 | 11/2019 | Schwartzer et al. | |
| 2019/0364916 A1 | 12/2019 | Jung et al. | |
| 2020/0178576 A1 | 6/2020 | Behrens et al. | |
| 2021/0333185 A1 | 10/2021 | Hayward et al. | |

FOREIGN PATENT DOCUMENTS

| | | | |
|---|---|---|---|
| GB | 2562275 A | | 11/2018 |
| JP | 3-272639 A | | 12/1991 |
| JP | 2001525928 A | * | 12/2001 |
| WO | 93/06735 A1 | | 4/1993 |
| WO | 99/07230 A1 | | 2/1999 |
| WO | 00/49899 A1 | | 8/2000 |
| WO | 02/077608 A2 | | 10/2002 |
| WO | 2004/026035 A1 | | 4/2004 |
| WO | 2005/089416 A2 | | 9/2005 |
| WO | 2006/002671 A1 | | 1/2006 |
| WO | 2011/017959 A1 | | 2/2011 |
| WO | 2011/123949 A1 | | 10/2011 |
| WO | 2012/039597 A2 | | 3/2012 |
| WO | 2012/141566 A2 | | 10/2012 |
| WO | 2013/144961 A1 | | 10/2013 |
| WO | 2014/124128 A1 | | 8/2014 |
| WO | 2015/017450 A1 | | 2/2015 |
| WO | 2016/084094 A1 | | 6/2016 |
| WO | 2016/187581 A1 | | 11/2016 |
| WO | 2017/048951 A1 | | 3/2017 |
| WO | 2017/100636 A1 | | 6/2017 |
| WO | 2017/132281 A1 | | 8/2017 |
| WO | 2017/172951 A1 | | 10/2017 |
| WO | 2017/200930 A1 | | 11/2017 |
| WO | 2018/009846 A1 | | 1/2018 |
| WO | 2018/094269 A1 | | 5/2018 |
| WO | 2019/028043 A1 | | 2/2019 |
| WO | 2019/036686 A1 | | 2/2019 |
| WO | 2019/104272 A1 | | 5/2019 |
| WO | 2019/129822 A1 | | 7/2019 |
| WO | 2019/145932 A1 | | 8/2019 |
| WO | 2019/169434 A1 | | 9/2019 |
| WO | 2019/177663 A1 | | 9/2019 |
| WO | 2020/023319 A1 | | 1/2020 |
| WO | 2020/051238 A1 | | 3/2020 |
| WO | 2020/123400 A1 | | 6/2020 |
| WO | 2020/181228 A1 | | 9/2020 |
| WO | 2020/247667 A1 | | 12/2020 |
| WO | 2021/009753 A1 | | 1/2021 |
| WO | 2021/055818 A1 | | 3/2021 |
| WO | 2021/092251 A1 | | 5/2021 |
| WO | 2021/222261 A1 | | 11/2021 |
| WO | 2021/25403 A1 | | 12/2021 |

OTHER PUBLICATIONS

Gongal et al. 2015 "Sensors and systems for fruit detection and localization: A review", Computers and Electronic in Agriculture, 116(2005, pp. 8-19. (Year: 2015).*

Spraying Fruit on a conveyor or Washing Fruit, www.pro-fruit.com/product/fruit-and-vegetable-washer-elevator-mill-maximill-3000/. pp. 1-3 (Year: 2010).*

Tiwari et al. "Fruit Ripeness Detection with machine learning using Raspberry Pi", IJIRT, vol. 6, issue 1, pp. 781-785. (Year: 2019).*

Amudipe, "Development of Lipid-Based Coatings for the Quality Maintenance of Fruit and Vegetables," Thesis submitted to the University of New South Wales for Doctor of Philosophy, 295 pages (Jun. 1996).

Baldwin, "Surface Treatments and Edible Coatings in Food Preservation," Chapter 21, in Handbook of Food Preservation, Second Edition, CRC Press, pp. 477-507 (Jul. 2007).

Baldwin et al., "Edible Coatings and Films to Improve Food Quality," Second Edition, CRC Press, 450 pages (2012).

Bhargava et al., "Fruits and vegetables quality evaluation using computer vision: A review," Journal of King Saud University—Computer and Information Sciences, vol. 33, pp. 243-257 (2021) (Available online Jun. 5, 2018).

(56) References Cited

OTHER PUBLICATIONS

Certified U.S. Appl. No. 63/016,074, filed Apr. 27, 2020.
Embuscado et al., "Edible Films and Coatings for Food Applications," Springer, 410 pages (2009).
GRAS Notice (GRN) No. 648, http://www.fda.gov/Food/Ingredients/PackagingLabeling/GRAS/NoticeInventory/default.htm, GRAS Notification for Mixture of Monoacylglycerides, 33 pages (Apr. 7, 2016).
GRAS Notice (GRN) No. 886, https://www.fda.gov/food/gernerally-recognized-safe-gras/gras-notice-inventory, Apeel Sciences GRAS Notice Submission for a Mixture of Monoacylglycerides Derived from Grape Seed, 45 pages (Oct. 9, 2019).
International Search Report and Written Opinion for Application No. PCT/US2021/036202 dated Oct. 27, 2021.
International Search Report and Written Opinion for Application No. PCT/US2021/036270 dated Oct. 28, 2021.
Kerbel et al., "Effects of "Semperfresh" coating on postharvest life, internal atmosphere modification and quality maintenance of 'Granny Smith' apples," J.K. Fellman (ed.), Proceedings of the Fifth International Controlled Atmosphere Research Conference, pp. 247-254, vol. 1—Pome fruits (Jun. 14-16, 1989, Wenatchee, WA).
Kore et al., "Application of Edible Coatings on Fruits and Vegetables," Imperial Journal of Interdisciplinary Research (IJIR), vol. 3, Issue-1, pp. 591-603 (2017).
Lazaro et al., "Color Measurement and Analysis of Fruit with a Battery-Less NFC Sensor," Sensors, 19, 1741; doi:10.3390/s19071741, 21 pages (2019).
Lin et al., "Innovations in the Development and Application of Edible Coatings for Fresh and Minimally Processed Fruits and Vegetables," Comprehensive Reviews in Food Science and Food Safety, vol. 6, pp. 60-75 (2007).
Lu et al., "Comparison of Four Nondestructive Sensors for Firmness Assessment of Apples," www2.atb-potsdam.de/CIGR-ImageAnalysis/images/images12/table_137_C2309.pdf, 6 pages (2012).
Mahajan et al., "Postharvest treatments of fresh produce," Phil. Trans. R. Soc. A, 372: 20130309, http://dx.doi.org/10.1098/rsta.2013.0309, 19 pages (2014).
Otoni et al., "Recent Advances on Edible Films Based on Fruits and Vegetables—A Review," Comprehensive Reviews in Food Science and Food Safety, vol. 16, pp. 1151-1169 (2017).
Pathare et al., "Colour Measurement and Analysis in Fresh and Processed Foods: A Review," Food Bioprocess Technol., vol. 6, pp. 36-60 (2013).
Quirós-Sauceda et al., "Edible coatings as encapsulating matrices for bioactive compounds: a review," J. Food. Sci. Technol., vol. 51, No. 9, pp. 1674-1685 (Sep. 2014).
Ruiz-Altisent et al., "Sensors for product characterization and quality of specialty crops—A Review," Computers and Electronics in Agriculture, vol. 74, pp. 176-194 (2010).
Shit et al., Edible Polymers: Challenges and Opportunities, Journal of Polymers, vol. 2014, Article ID 427259, 13 pages, http://dx.doi.org/10.1155/2014/427259 (2014).
Slaughter, Presentation of "Nondestructive Quality Measurement of Horticultural Crops," 20 pages (Publicly known at least as early as Dec. 7, 2021).
Wang et al., "Fruit Quality Evaluation Using Spectroscopy Technology: A Review," Sensors, vol. 15, pp. 11889-11927; doi:10.3390/s150511889 (2015).

\* cited by examiner

SELECTIVELY TREATING PLANT ITEMS

CROSS-REFERENCE TO RELATED APPLICATIONS

This application claims priority to International PCT Application Serial No. PCT/US2021/036202, filed on Jun. 7, 2021, which claims the benefit of: U.S. Provisional Application Ser. No. 63/035,818, titled "Barrier Coating Compositions and Wash Compositions for Perishables and Method and Systems Relating Thereto," filed by DeMaster et al. on Jun. 7, 2020; U.S. Provisional Application Ser. No. 63/045,155, titled "Barrier Coating Compositions, Wash Compositions, and Other Compositions for Perishables and Methods, Systems, Kits, and Coated Items Relating Thereto," filed by DeMaster et al. on Jun. 28, 2020; U.S. Provisional Application Ser. No. 63/065,484, titled "Barrier Coating Compositions, Wash Compositions, and Other Compositions for Perishables and Methods, Systems, Kits, and Coated Items Relating Thereto," filed by DeMaster et al. on Aug. 13, 2020; and U.S. Provisional Application Ser. No. 63/195,147 entitled "Selectively Treating Plant Items" filed by DeMaster et al. on May 31, 2021; the entire contents of each of which are herein incorporated by reference. To the extent appropriate, a claim of priority is made to each of the above-disclosed applications.

TECHNICAL FIELD

Various embodiments relate generally to selectively treating, and especially coating, plant items (e.g., fruits and vegetables), to, for example, prolong their shelf life or duration of freshness or usability.

BACKGROUND

Food spoilage is a major global problem, especially with respect to fresh fruits and vegetables. Studies have estimated that more than 40% of food that is grown is wasted without being consumed. Much of this waste is due to spoilage that occurs in the food supply chain. Such food waste leads to a myriad of problems, including excessive land cultivation for agriculture and an outsized carbon footprint associated with shipping and refrigeration of ultimately wasted food, which may contribute to climate change and other environmental problems. Moreover, such excessive waste increases food prices, which deprives vulnerable populations sufficient access to nutritious fresh produce.

Fruits and vegetables have natural skins that resist degradation processes and help delay rotting or drying out of the fresh produce prior to consumption. Damage to these natural protective surfaces can result in rapid degradation that can negatively impact the quality and taste of the produce, and even render the produce unfit for consumption. Such damage can occur during any of the multitude of supply chain steps prior to consumption, including, for example, during harvest, during processing at fruit or vegetable processors, during the many transportation steps in the supply chain, during storage, during stocking or display at the retailer, during the purchasing process by the end consumer, and during transport and storage by the end consumer.

Moreover, even if the fruit or vegetable is not damaged, spoilage or unsuitable quality degradation can occur due to timing factors in the supply chain. Steps such as air transport and refrigeration can be employed to help avoid such timing-related problems; however, such steps are expensive and are not environmentally friendly. Such issues are also a problem for other agricultural products such as, for example, plant bulbs, seedlings, plant cuttings, fresh-cut flowers, nuts, seeds, and the like.

SUMMARY

The present disclosure provides methods, equipment, and systems for selectively treating, and particularly coating, harvested plant items such as perishable live plant items, and particularly fresh fruits and vegetables, to prolong their shelf life or duration of freshness or usability. The methods and equipment may also have utility with plant cuttings for vegetative propagation, cut flowers, nuts, and bulbs.

In some embodiments, the present disclosure provides a method for selectively applying treatments to at least some of a batch of plant items, the method comprising conveying, in an industrial processing line, at least one plant item in the batch of plant items to a sensing region having one or more sensors, assessing, with the one or more sensors and a computing device, one or more properties of the at least one plant item associated with ripeness and/or another attribute, conveying the at least one plant item to a treatment region, determining a treatment to apply to the at least one plant item based on the assessed one or more properties, and applying, in the treatment region, the treatment to the at least one plant item.

In some embodiments, the present disclosure provides a system configured to operate with an industrial processing line for selectively applying treatments to plant items, the system comprising one or more sensors, and a computing device in communication with the one or more sensors, the computing device having a memory and a processor, the memory storing instructions which when executed by the processor cause the computing device to assess properties of a plant item associated with ripeness and/or another attribute with the one or more sensors, determine a treatment to apply to the plant item based on the assessed one or more properties, and generate a treatment instruction to apply the determined treatment to the plant item.

In some embodiments, the present disclosure provides a non-transitory computer readable medium storing instructions which, when executed by a computing system, cause a system for selectively applying treatments to at least some of a batch of plant items to convey at least one plant item in the batch of plant items to a sensing region having one or more sensors, assess, with the one or more sensors and the computing system, one or more properties of the at least one plant item associated with ripeness and/or another attribute of the at least one plant item, convey the at least one plant item to a treatment region, determine a treatment to apply to the at least one plant item based on the assessed one or more properties, and apply, in the treatment region, the treatment to the at least one plant item.

In some embodiments, the present disclosure provides a method of coating a plant surface. The method comprises assessing (e.g., measuring or identifying) a characteristic of a plant item, which can optionally comprise assessing two or more different characteristics of a plant item; adjusting one or both of a wash characteristic or a coating characteristic (e.g., a crosslinking parameter, coating solids, an amount of applied coating per substrate area, a ripening agent, a ripening inhibitor, an antimicrobial parameter, a color parameter, surface tension, etc.) of a plant coating composition as a function of the assessed plant item characteristic (e.g., a carbon dioxide level, an oxygen level, an ethylene level, a sugar level, an acid level, a firmness level, a color indicator or other visual indicator, whether the plant item has been treated with a ripening agent such as ethylene gas, whether the plant item has been treated with a ripening inhibitor such as, e.g., an ethylene receptor antagonist, etc.); and applying a liquid plant coating composition to at least a portion of a surface of the plant item.

In some embodiments, the present disclosure provides a method of selectively applying a treatment to a plant item, the method comprising: in an industrial processing line, conveying a plant item to a treatment region (preferably a coating region, optionally a washing region); and applying a treatment (preferably a coating composition treatment, but optionally a wash treatment) to the plant item based on a property of the plant item, or one or more other plant items of a like kind (e.g., a representative sample of plant items), determined using sensor information.

In some embodiments, the present disclosure provides a method for selectively applying a treatment to at least some of a batch of plant items. The method comprises, in an industrial processing line, conveying at least one plant item in the batch of plant items to a sensing region having one or more sensors; with the one or more sensors and a computing device, assessing one or more properties of the plant item associated with ripeness and/or another attribute; conveying at least one of the batch of plant items to a treatment region; in the treatment region, applying (preferably via spraying, dipping, brushing or curtain coating) a first treatment to at least one of the batch of plant items if the assessed property exceeds a first threshold, or applying, preferably (preferably via spraying, dipping, brushing or curtain coating), a second treatment to at least one of the batch of plant items if the assessed property is equal to or less than the first threshold, the first treatment being different than the second treatment. In some embodiments, a machine learning model is used to select an optimal treatment to apply to the at least one of the batch of plant items. In some examples, the optimal treatment is selected from one of the first treatment or the second treatment. In some embodiments, a machine learning model is used to predict an optimal value to use as the first threshold. In some examples, the machine learning model is trained with various training data including historical data of related plant items such as data previously collected from the one or more sensors with associated tags. Other methods can be used for identifying the optimal treatment to apply to the at least one of the batch of plant items.

In some embodiments, the present disclosure provides a method for selectively applying a treatment to at least some of a batch of plant items. The method comprises, in an industrial processing line, conveying at least one plant in the batch of plant items to a sensing region having one or more sensors; with the one or more sensors and a computing device, assessing one or more properties of the plant item associated with ripeness and/or another attribute; determining, based on (i) the one or more assessed properties, (ii) a customer-defined standard for a customer, and optionally (iii) shipping parameters associated with the customer, whether the plant item is likely to meet the customer-defined standard upon arrival at the customer; and based on a determination that the plant item is likely to meet the customer-defined standard upon arrival at the customer, applying a first treatment to the plant item or based on a determination that the plant item is not likely to meet the customer-defined standard upon arrival at the customer, applying a second treatment that is different than the first coating.

In some embodiments, the present disclosure provides a method for selectively applying a treatment to at least some of a batch of plant items. The method comprises, with one or more sensors and a computing device, assessing one or more properties of at least one plant item in the batch of plant items, the assessed one or more properties being associated with ripeness and/or another attribute; in the treatment region of an industrial processing line, applying (preferably via spraying, dipping or curtain coating) a first treatment to at least one of the batch of plant items if the assessed property exceeds a first threshold, or applying (preferably via spraying, dipping or curtain coating) a second treatment to at least one of the batch of plant items if the assessed property is equal to or less than the first threshold, the first treatment being different than the second treatment. In some embodiments, a machine learning model is used to select an optimal treatment to apply to the at least one batch of plant items. For example, the optimal treatment is selected from one of the first treatment or the second treatment using the machine learning model. In some embodiments, a machine learning model is used to predict an optimal value to use as the first threshold. As described above, the machine learning model can be trained on various training data including historical data of related plant items including data collected by sensors with associated tags. Other methods can be used for identifying the optimal treatment to apply to the at least one batch of plant items. In some embodiments, the present disclosure provides a coating system for coating a perishable plant item comprising: a sensor, more typically a plurality of sensors;

and a computing device including at least a processing device and including, or in communication with (e.g., via an internet connection, wired network connection, or wireless network connection), a computer readable storage device, the computing device in communication with the sensor, the computer readable storage device storing data instruction executable by the computing device to cause the computing device to: (a) determine a level of ripeness and/or another attribute of the plant item, and (b) generate a coating instruction for the plant item.

In some embodiments, the present disclosure provides a computer readable storage device storing data instructions that, when executed by a processing device, cause the processing device to perform operations comprising: receive an input from one or more sensors, wherein the input comprises a measurement and/or identification associated with a plant item to be coated (e.g., any of those disclosed herein, preferably an edible fruit or vegetable, more preferably a harvested edible fruit or vegetable); and generate a coating recommendation or instruction.

In some embodiments, the present disclosure provides a system comprising an industrial processing line, or one or more portions thereof, for processing live plant items, the system comprising: (a) one or more sensors for generating sensor information for conveyed live plant items, the sensor information relating to a ripeness parameter and/or other parameter of the live plant items; (b) one or more applicators for applying a liquid treatment (preferably a coating composition and/or a wash solution or other liquid pretreatment) other than water to the live plant items; (c) a computing device configured to execute instructions that, when executed, perform a method for determining, based on the sensor information, which liquid treatment to apply to the live plant items out of a plurality of potential treatment choices.

In some embodiments, the present disclosure provides methods and packaging for supplying a batch of produce to a consumer including produce having differential ripeness, thereby enhancing the consumer's ability to consume produce of a desired ripeness over time.

The description that follows more particularly exemplifies illustrative embodiments. In several places throughout this description, guidance is provided through lists of examples, which examples may be used in various combinations. In each instance, the recited list serves only as a representative group and should not be interpreted as an exclusive list. Thus, the scope of the present description should not be limited to the specific illustrative structures described herein, but rather extends at least to the structures described by the language of the claims, and the equivalents of those structures. Any of the elements that are positively recited in this description as alternatives may be explicitly included in the claims or excluded from the claims, in any combination as desired. Although various theories and possible mechanisms may have been discussed herein, in no event should such discussions serve to limit the claimable subject matter.

DETAILED DESCRIPTION

Terminology

Figure 1:
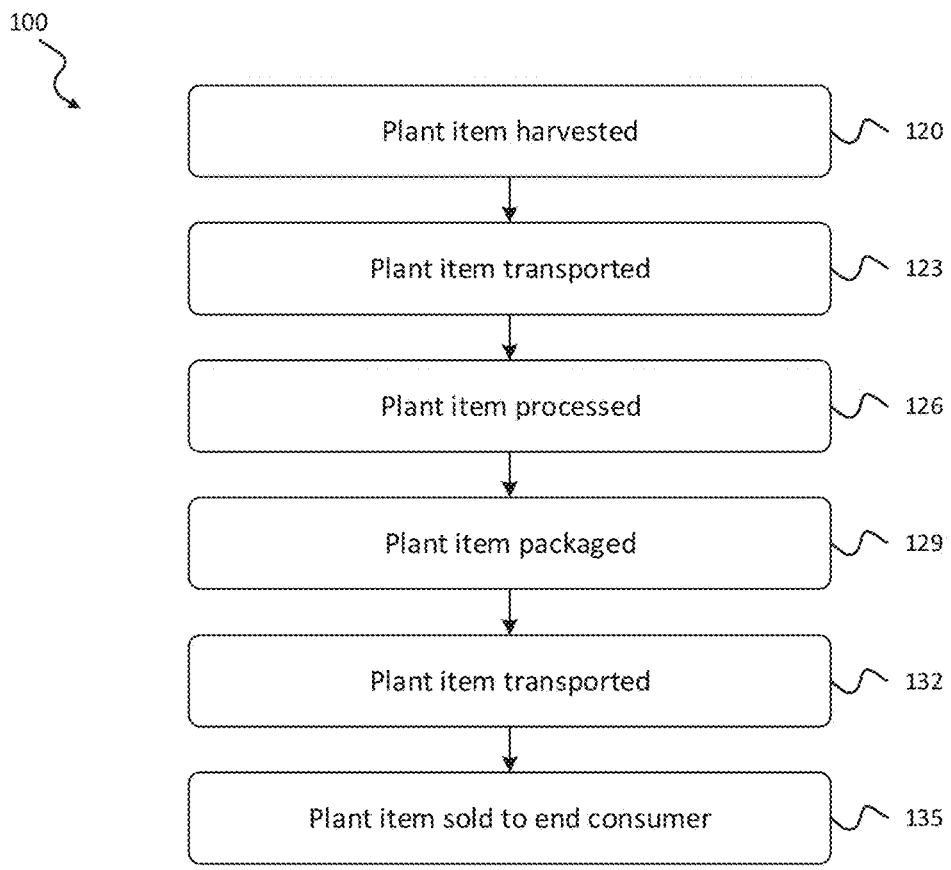
FIG. 1 depicts an exemplary method by which a plant item may move from its point of cultivation to an end consumer.

Herein, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the description for the listed elements. Thus, the phrase "consisting essentially of" indicates that the listed elements are required or mandatory, but that other elements are optional and may or may not be present depending upon whether or not they materially affect the activity or action of the listed elements. Any of the elements or combinations of elements that are recited in this description in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the description that may afford certain benefits, under certain circumstances. However, other embodiments may also be preferred, under the same or other circumstances. Furthermore, the recitation of one or more preferred embodiments does not imply that other claims are not useful and is not intended to exclude other embodiments from the scope of the description.

In this description, terms such as "a," "an," and "the" are not intended to refer to only a singular entity but include the general class of which a specific example may be used for illustration. The terms "a," "an," and "the" are used interchangeably with the terms "at least one" and "one or more."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints and all subranges (e.g., 1 to 5 includes 1, 1.5, 2, 2.75, 3, 3.80, 4, 5, etc. as well as 2 to 5, 1 to 4, 2 to 4, 1.5 to 3, etc.).

As used herein, the terms "room temperature" or "ambient temperature" refers to a temperature of 20° C. to 25° C. If humidity can affect a given parameter measured at room temperature or ambient temperature and a relative humidity is needed, then a relative humidity of 50% should be used, unless indicated otherwise herein.

Reference throughout this description to "one embodiment," "an embodiment," "certain embodiments," or "some embodiments," etc., means that a particular feature, configuration, composition, or characteristic described in connection with the embodiment is included in at least one embodiment of the description. Thus, the appearances of such phrases in various places throughout this description are not necessarily referring to the same embodiment of the description. Furthermore, the particular features, configurations, compositions, or characteristics may be combined in any suitable manner in one or more embodiments.

The term "skin" as used herein in the context of a fruit or vegetable is used expansively and encompasses rinds, peels, and any other outer endogenous coverings of fruit or vegetables. Depending on the fruit or vegetable, the skin may or may not be edible.

The phrases "free of", "does not include", "does not include any" and the like used herein are not intended to preclude the presence of trace amounts (e.g., parts-per-billion (ppb) or parts-per-trillion (ppt) levels) of the pertinent structure or compound that may be unintentionally present, for example, as environmental contaminants.

As used herein, the terms "harden" and "hardened" are used in their broad contexts as understood by persons of skill in the art. The terms are not intended, for example, to require any particular level of rigidity, firmness, scratch resistance, or crosslinking. Rather, the terms are used for convenience to allow for efficient differentiation between liquid coating compositions and "dry" coatings subsequently formed from the liquid coating compositions in which all or substantially all of a liquid carrier is no longer present in the composition (e.g., due to evaporation or other drying or curing). The term may also be used to indicate a continuous or substantially continuous coating formed from a powder coating composition—e.g., by subjecting the applied powder coating composition to heat or other cure conditions.

As used herein, the term "chemically-different" in the context of a chemically-different composition (or part) refers to a composition that (i) includes a different concentration (e.g., other than a trivial concentration difference due, for example, to unavoidable/unintentional concentration variations that do not impact coating outcomes) of one or more ingredients relative to a comparison composition, (ii) includes one or more ingredients not present in the comparison composition and/or (iii) does not include one or more ingredients present in the comparison composition. Dilution of a base liquid composition with an additional amount of the liquid carrier (e.g., water and/or organic solvent) results in a chemically-different composition.

As used herein, the term "soon-to-be-harvested" refers to a plant item such as a fruit or vegetable that is fully grown or substantially fully grown and market ready or substantially market ready. By way of example, a fruit or vegetable within a day or two prior to harvest is a soon-to-be-harvested plant item.

The term "treatment" is used broadly herein and encompasses both wash compositions and coating compositions. Unless specifically indicated otherwise herein, pure water (e.g., tap water) does not constitute a "wash treatment" or "wash composition".

The terms "coating" and "coating composition" as used herein do not encompass the application of water alone to a substrate to be coated. By way of example, dipping a plant item into tap water or well water does not constitute coating the plant item or applying a coating composition to the plant item. However, by way of further example, an aqueous composition constituting 99% by weight water and 1% by weight of a lipid constitutes a coating composition.

The term "aqueous" is broadly used herein to encompass a substance, solution or system having water as a medium, including, for example, substances, solutions or systems that are water-soluble, water-dispersible, and emulsions, including "oil-in-water" and "water-in-oil" microemulsions, nanoemulsions, microdispersions, nanodispersions, and the like.

Unless indicated otherwise, the term "carboxyl-functional compound" as used herein refers to compounds having one or more carboxyl groups (—COOH), one or more salt groups formed from carboxyl groups (typically base-neutralized carboxyl groups), or a combination thereof.

Unless indicated otherwise, the term "hydroxyl-functional compound" as used herein refers to compounds having one or more hydroxyl groups (—OH), one or more salt groups formed from hydroxyl groups (typically base-neutralized acidic hydroxyl groups, e.g., on ascorbic acid), or a combination thereof.

The terms "total solids" and "total non-volatiles" and the like are used interchangeably herein. As will be appreciated by persons having ordinary skill in the art, the amount of total solids in a component or composition may be calculated based on the amount of starting material(s) employed and the amount of solids in the starting material(s). The amount of solids (or non-volatiles) in starting materials is typically provided by the manufacturer and/or supplier of the material in, for example, a technical data sheet (TDS). If for some reason a reliable calculation is not possible, standard test methods for determining solids and volatile content are well known in the art. An example of such a standard test method is ASTM D2369-20. Care should be exercised in the event a composition includes a sensitive material that chars in the test conditions (e.g., certain sensitive biopolymers). In such situations, appropriate adjustments may need to be made such as, for example, use of a modified temperature to remove volatiles that avoids charring.

The terms "crosslink" or "crosslinking" are used broadly herein to encompass one or more compounds capable of preferentially interacting or associating with another component of the coating composition such as, for example, via a functional group (e.g., an active hydrogen group) present on the component (e.g., the active hydrogen group), which preferably results in one or more desirable coating properties when enough such interactions occur. Such interactions include covalent bonding, chelation, electrostatic complexation, and the like.

The terms "tag", "tags", "tagged", and "tagging" are used broadly herein to refer to adding details (sometimes referred to as tags or labels) to raw data. An example of the raw data includes the data collected by the sensors, images, videos, etc. Some of the tags represent a type, classification, outcome, treatment applied (including indicating when no treatment was applied) for the raw data. One or more tags can also be used to link raw data, for example, with an item ID number. In some embodiments, some or all of the tags are used to help train a machine learning model to identify a particular classification, recommendation, prediction, or predicted tag, when encountering similar input data without some or all of the tags.

In some embodiments, a material may qualify as one or more different recited materials of an embodiment. Unless indicated otherwise herein, such materials should be considered in determining the concentrations or amounts of any material categories in which they fit under. Thus, for example, a composition that includes 0.25% by weight ("wt-%") of monolaurin is considered to be a composition that includes 0.25 wt-% of a mono-glyceride (i.e., an organic water-barrier material) and 0.25 wt-% of an antimicrobial agent, even if such composition does not include any other organic binder component or antimicrobial agent. The discussions herein should be understood to explicitly disclose both "over-lapping" embodiments, e.g., as described above in which an ingredient can fulfill two or more material categories and "non-overlapping" embodiments in which each recited ingredient is fulfilled by a separate ingredient (e.g., where a composition including both a mono-glyceride and an anti-microbial agent includes at least two ingredients—as opposed to merely one that fulfills both material categories).

Cultivation to End Consumer

An exemplary method 100 for advancing a plant item from its point of cultivation to an end consumer is depicted in FIG. 1. Specifically, a plant item may be harvested (120) from the point at which it is cultivated. Part of the harvesting (120) process may include removing undesirable material that is initially harvested with the plant item (e.g., leaves, stems, shells, protective skins, etc.). Harvesting (120) may be performed manually or with automated equipment.

Once harvested, typically with many other like items, the plant item may be transported (123) from the point of harvest to a processing facility. For example, plant items may be loaded directly onto a truck, or quantities may be loaded into carts, crates, or boxes; and the carts, crates or boxes may be transported (123) to a processing site (e.g., by truck, train, plane, boat, etc.). In some embodiments, the harvested plant items may be stored for a period of time prior to delivery to the processing facility and/or prior to being processed at the processing facility as described herein. It is also contemplated that one or more optional storage steps may occur at one or more intermediate points in the processing methods described herein. In some embodiment, no storage step is included during processing at a processing facility.

At the processing facility, the plant item may be processed (126) in a variety of different ways, as described herein. Although certain preferred embodiments include one or more coating steps, such coatings and coating steps are optional and may not be present in some embodiments. Thus, in some embodiments, no treatment is applied to the plant item.

After processing (126), the plant item may be packaged (129) for further transport and distribution, ultimately to an end consumer. In some embodiments, like plant items are packaged (129) in small quantities for ultimate sale to individual consumers; in other embodiments, like plant items are packaged (129) in larger quantities for wholesale consumers or for distribution through multiple steps (e.g., to regional warehouses, then local warehouses, then individual stores). In some embodiments, the plant items may be stored prior to or after packaging such as, for example, in a ripening room or storage room. Although not shown in FIG. 1, method 100 may include cooling to remove field heat from the harvested plant items to reduce the rate of respiration of the plant item (e.g., for certain produce), microbial activity, and/or refrigeration load. Similarly, although not shown in FIG. 1, method 100 may include a storage step (e.g., low temperature storage) at some point after being processed (126) to, for example, enable orderly marketing and distribution during times of peak production.

After being appropriately packaged (129), plant items may be further transported (132). One or more wholesalers, distributors, produce storage companies or the like may optionally handle the plants items in the supply chain to end consumers.

Finally, the plant items may be sold (135) to end consumers, such as individual retail consumers, restaurants, wholesale clubs or cooperatives, etc.)

Exemplary Processing Methods
Overview

Figure 2:
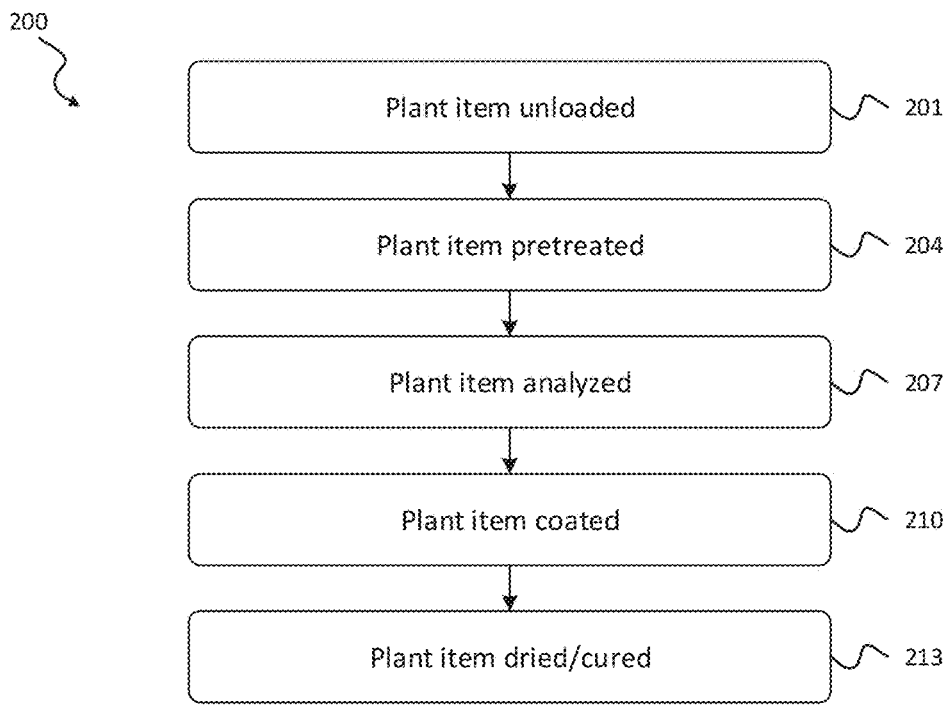
FIG. 2 depicts an exemplary method by which a plant item may be processed at a processing facility.

FIG. 2 depicts an exemplary method 200 by which plant items (e.g., perishable live plant items such as fresh fruit, fresh vegetables, plant cuttings for vegetative reproduction, and cut flowers) may be processed at a processing facility (e.g., corresponding to processing (126) in the method 100 depicted in FIG. 1). Example method 200 may be performed with a fully automated, or at least partially automated, system, which preferably includes multiple components that are in data communication with one another to provide improved overall performance. In some embodiments, as shown, method 200 may include unloading (201), pretreating (204), analyzing (207), coating (210), and drying/curing (213). In some embodiments, method steps may be omitted; in other embodiments, other steps may be added.

As shown, the method 200 may include unloading (201) plant items. For example, plant items may be unloaded (201) from a container in which they are transported (e.g., a truck, crate, box, cart, etc.), to a processing line. In some embodiments, the processing line is an automated or partially automated line that conveys plant items from the point of unloading, through various processing steps, to a point of being packaged for another transport and/or storage (e.g., low temperature storage).

The method 200 may further include pretreating (204) plant items. In some embodiments, pretreating (204) may include further separating the plant items from undesirable material that may remain attached to or transported with the desirable portions of the plant items—such as, for example, stalks, stems, leaves, shells, skins, overly ripe or damaged plant items, etc. In addition, the plant items may be washed and otherwise treated (e.g., wet or dry dumping, debris removal, leaf and/or stem or stalk removal, washing, water or mechanical transport and the like)—to clean and sanitize them and/or to prepare them for subsequent analysis and coating.

Typically, a transporter (e.g., conveyor belts; auger or screw conveyors; and/or wheels, diabolos, cups, brush rollers, holders, or clamping conveyor systems) moves plant items from one area to another in a processing facility. Various washing, sanitizing and/or pretreatment steps may be performed, exemplary details of which are described below.

The method 200 may further include analyzing (207) the plant items various ways. In some embodiments, the analyzing (207) is employed to assess a characteristic (e.g., with one or more sensors and a computer-implemented algorithm), or a plurality of characteristics, such as ripeness in the case of a fruit or vegetable, sheen, moisture content, sugar content, nutritional density, etc. In some embodiments, details of the assessed characteristic(s) may be employed to selectively coat the plant item.

In an analyzing (207) step, one or more sensors may collect information (e.g., via measuring or identifying) relating to one or more characteristics associated with the plant item. Examples of such characteristics include an acid level (e.g., total acid, ascorbic acid, etc.), a sugar level (e.g., a degrees Brix, commonly abbreviated as Bx°), a ratio of sugar to acid, a level of soluble solids, a color parameter (e.g., a color intensity, a fraction of surface area that is a particular color, etc.), a visible indicator, a gloss level, a gas amount (e.g., an internal or emitted gas amount such as, e.g., carbon dioxide, ethylene, oxygen, or water vapor), a vitamin content, an internal color, lycopene content, prevalence of cotyledons, a wall thickness, a starch content, a microbial parameter, a firmness amount, or a combination thereof. The sensors may be in a static location or may move, for example, to allow for the plant item to be in the sensor's sensing zone for a longer time.

As part of the analyzing (207), a determination may be made based upon the one or more characteristics. In preferred embodiments, the determination relates to the ripeness and/or quality of the plant item such as, for example, the extent of ripeness and/or the quality (e.g., grade) of the plant item.

A treatment decision for the plant item may be made as a function of the determination. Examples of such treatment decisions include adjusting one or both of a wash characteristic or a coating characteristic. That is, a treatment decision may include selectively applying a first treatment or a second treatment (or one of more than two possible treatments). In some embodiments, the treatment may include a wash (i.e., a wash treatment other than merely washing with water) and/or an etch; in some embodiments, the treatment may include application of a coating composition having a particular coating thickness when hardened (e.g., dried) or other characteristics; in some embodiments, the coating composition is a liquid coating composition. In some embodiments, the treatment method includes two or more of a wash treatment, an etch, or application of a coating composition.

Within the analyzing (207) step, determinations and treatment decisions may be typically made by a computing device in communication with the one or more sensors, which typically includes a processing device and a computer readable storage device.

The treatment decision may be implemented with respect to the plant item. That is, the method 200 may include coating (210) the plant item. Examples of such implemented decisions include one or more of the following: application of a coating having a particular coating chemistry to the plant item (e.g., presence or amount of crosslinking component(s); presence or amount of barrier ingredient(s) such as water-barrier, ethylene-barrier, oxygen-barrier, and/or the like barrier ingredients; presence or amount of active ingredient(s) such as, e.g., ripening-related active ingredients such as ripening inhibitor(s), ripening accelerator(s), or ripening-related adjuvant(s); presence or amount of antimicrobial agent(s); presence or amount of flavorant(s); presence or amount of probiotic(s); presence or amount of enzyme(s) or other digestive aids; presence or amount of wetting additive(s); and/or presence or amount of adhesion promoter(s)); application of a coating at a particular determined coating thickness to the plant item; application of a coating to particular determined portion(s) of a plant item; application of a wash solution having a particular chemistry to the plant item (e.g., presence or amount of antimicrobial agent(s), presence or amount of ripening-related active ingredients such as ripening inhibitor(s), ripening accelerator(s), or ripening-related adjuvant(s)); and the like.

In some embodiments, the coatings are customized to a particular plant item, subset (such as a current population of items advancing on a processing line, including a subset of a batch) or batch or lot of plant items, based on one or more previously assessed characteristics as derived by sampling on behalf of the whole batch or lot, or advancing through a sensing step on a processing line assessing in-line the parts or subsets of the whole, or other method. In some embodiments, a coating may enable a plant item to retain a high moisture content (and/or corresponding weight, shape and size) for a longer period of time than without the coating; in some embodiments, a coating may enable a plant item to retain its color or sheen for a longer period of time (and/or better meet customer expectations) than would be possible without the coating; in some embodiments, a coating may enable a plant item to resist spoilage (including by resisting the growth of mold or fungus) and/or maintain a higher level of quality for a longer period of time than without the coating. The coating may enable two or more, or all of these, beneficial outcomes to be accomplished simultaneously.

A coating system may preferably include one or more sensors capable of providing one or more signal outputs (e.g., data values), more typically a plurality of sensors, and one or more coating applicators for applying the coating composition to a plant item. In some embodiments, the sensor is configured to output a signal carrying a value of a measurement associated with the plant item to be coated. For example, the sensor may be configured to identify, measure, or both identify and measure a ripeness or quality parameter associated with a plant item, or population of plants items, to be coated. The coating systems may include two or more different types of sensors, which may be configured to measure a same or different parameter associated with a plant item or population of plant items.

A coating system may be included within a high-throughput industrial processing line, or one or more portions thereof, for treating and/or packing perishable plants items such as freshly harvested plant items, including any of those disclosed herein, and particularly fruits, vegetables, cut flowers, or plant cuttings. The coating systems and methods described herein may also be used with plant item processing lines others than high-throughput processing lines. High-throughput produce packing lines are preferred industrial processing lines. (As used herein, "industrial processing line" generally refers to a high-volume, typically fast-moving line for handling in an automated or semi-automated manner, commercially significant volumes of plant items for shipment often to many disparate customers or customer locations over a potentially large geographic area—i.e., volumes that typically represent many truckloads of plant items (or volumes corresponding to train cars, containers, etc.) over a short period of time (e.g., an hour, a working shift, one day, etc.)—in contrast to small scale operations that may be more tailored to serving local, on-site retail customers). Any suitable coating applicators, or combination thereof, capable of applying a desired coating weight to preferably form a coating, which is preferably an at least substantially continuous coating, may be employed.

Examples of suitable applicators for liquid coating compositions include curtain or wash coaters, dip coaters, spray coaters (e.g., spray, flood, fog, or misting bars; spray, flood, fog, or misting guns or nozzles; and the like), brush applicators, and combinations thereof. As used herein, the terms "spray" and "spraying" also encompass mist and misting, respectively, as well as fog and fogging, respectively. The coating composition may optionally be subjected to air flow to remove excess coating material (e.g., using an air-knife) and/or an electric charge or voltage just prior to and/or during spray application to modify one or more properties of the spray applied coating composition such as, for example, to increase one or more reactivities. (See, for example, U.S. Pat. No. 10,537,130 for equipment, methods, and materials.)

Plant items to be coated may be rotating as the coating composition is applied to facilitate coating of the desired surface portions. In some embodiments, the coating system is configured such that the plant item or other perishable is coated while simultaneously rotating and being transported in a direction of travel, such as, for example, in the direction of travel of a transporter such as, for example, a conveyor belt or drive. An example of equipment for causing such rotation during coating is provided in WO2019/028043 (Holland et al.), which describes a conveyor apparatus for simultaneously transporting and rotating fresh produce during coating.

In some embodiments, excess residual coating composition after application (e.g., resulting from over-spray, flood coating, and the like) may be collected and recycled—i.e., used again to treat perishable items. Such collected coating composition may optionally be subjected to one or more sanitization steps prior to re-use.

The method may include drying/curing (213) the previously applied (210) coatings (e.g., coatings that are applied wet or in a manner requiring a chemical reaction to achieve a final desired state). Any conditions effective to form a hardened adherent coating on the plant item may be used so long as such conditions preferably do not unsuitably impact the plant item. In some embodiments, the coatings may cure naturally within a set period of time; in some embodiments, coated plant items are exposed to heat or streams of air; in some embodiments, a second coating may be applied to a first coating to initiate, catalyze or accelerate curing of the first coating. Such a second coating may be applied prior to drying of the first coating (i.e., "wet-on-wet") or after drying and/or curing of the first coating (i.e., "wet-on-dry"). In some embodiments, for example, ventilation or heat or energy, e.g., in the form of infrared, radiative heat energy, ultraviolet light, e-beam energy, or other energy forms may be applied.

Additional details of each of the exemplary steps of the method 200 are now described with reference to FIG. 3.

Unloading

Figure 3:
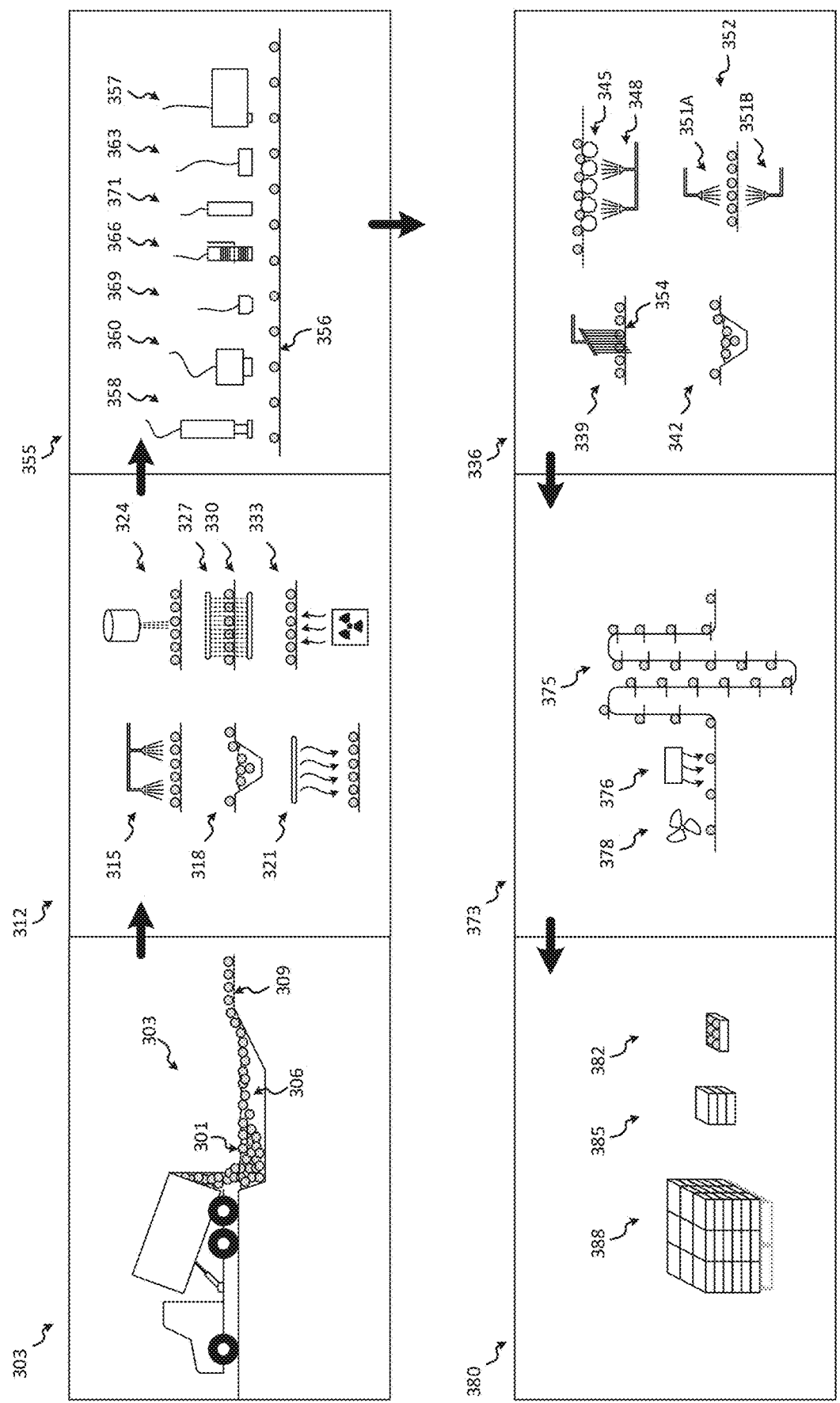
FIG. 3 provides a graphical depiction of various aspects of an exemplary processing facility.

As shown in FIG. 3, harvested live plant items (depicted as round objects, of which item 301 is representative) are unloaded in an unloading area 303. As depicted in one embodiment, the plant items are dumped into a bath 306, from which they are drawn onto an automated line, such as conveyor 309. The unloading area 303 is merely representative; other unloading schemes may be employed.

Pretreatment

From the unloading area 303, plant items may be conveyed to one or more optional pretreatment stations that comprise a pretreatment area 312. The pretreatment stations may include sprayers 315 for delivering various washes, sanitizing rinses, chemical washes, and/or other liquid compositions. A liquid bath 318 may be provided to as another manner in which to expose plant items to similar washes, sanitizing rinses, chemical washes, and/or other liquid compositions. An ultraviolet (UV) light source 321 may be provided as another pretreatment station. An electron beam 324 may be provided as another pretreatment station. A pulsed electric field 327 or low-temperature plasma 330 may be provided as another pretreatment station. Gamma radiation 333 may be provided at another pretreatment station. The foregoing are merely exemplary; other pretreatment stations and processes are possible for various possible purposes, which are now described.

In some embodiments, a surface of the plant item to be coated (e.g., the skins of fresh fruit or vegetables) is subjected to one or more pretreatment steps prior to coating to improve application of the coating composition and/or improve one or more coating properties of the resulting coating. In some embodiments, the surface of the plant item to be coated may be subjected to a plurality of different pretreatment steps which may be the same or different. The pretreatment process may lead to a variety of beneficial outcomes. For example, pretreatment may lead to better wetting out of the surface of the plant item by the liquid coating compositions, thereby enabling formation of a more continuous and/or uniform coating. Alternatively, or additionally, the pretreatment step may lead to enhanced adhesion of the hardened coating to the plant surface, which may lead to a variety of beneficial outcomes such as, for example, enhanced shelf-live for the coated live plant item (e.g., via reduced initial microbial load), reduced mass loss, enhanced resistance against the coating being prematurely washed away, enhanced abrasion resistance, enhanced coating flexibility or other mechanical properties, and the like.

The pretreatment process may include application of one or more compositions to the surface of the plant item to be coated (e.g., liquid compositions, plasma, gas or otherwise), application of one more energy forms to such surface (e.g., UV light, electron-beam, or pulsed electric field (PEF)), application of one or more physical forces to such surface (e.g., lightly abrading the plant surface to gently texturize or roughen the surface and/or remove or reduce waxiness without appreciably affecting its overall thickness or integrity), or both in multiple discrete steps and/or combined steps. The pretreatment may be combined with a wash (e.g., a chemical wash) or rinse step such that, for example, a pretreatment composition also functions as a wash composition to remove dirt and other contaminants or residuals from the surface of the plant item to be coated. The plant item to be coated may optionally be washed (e.g., with a water rinse) before the pretreatment, after pretreatment, or both before and after the pretreatment.

While not intending to be bound by theory, it is believed that certain pretreatment steps can modify the low-energy surface of certain fruit and vegetable skins (including, e.g., peels and rinds) to make the surfaces more conducive to coating. For example, suitable acidic pretreatment compositions (e.g., having an acidic pH such as less than 3.5, less than 3, less than 2, less than 1.5, and so on) may be used to gently "etch" the surface of the plant skin without appreciably damaging it in a manner that would compromise the integrity of the skin. Alternatively, alkaline pH chemical-etch solutions may also be used that include one or more bases such as, for example, one or more strong bases such as sodium hydroxide. Enzymatic pretreatments may be used to treat the surface, preferably in a manner that lowers the surface energy or otherwise improves coating application, with examples of suitable enzymes including cutinase, pectinase, and mixtures thereof. Applied energy forms such as, e.g., UV and electron-beam may also be used to gently etch the surface. While not intending to be bound by theory, it may be advantageous to use a higher strength (e.g., more intense) and/or longer duration of such applied energy than that typically used for fruit or vegetable sanitization.

In some embodiments, the pretreatment composition includes one or more phosphorus-containing compounds in an efficacious amount to achieve a desired result (e.g., mildly "etch" the surface of the plant skin, lower the surface energy of the plant skin (e.g., as indicated by a decrease in the contact angle of deionized water disposed on the treated skin), improve wetting out of the plant skin, and/or improve coating adhesion). While not intending to be bound by theory, phosphorus acids may function as adhesion promoters through associating with metal-containing compounds present on the plant item and/or as a mild etching compound when present in a suitable amount. Examples of suitable phosphorus acids may include a phosphinic acid ($H_3PO_2$), a phosphonic acid ($H_3PO_3$), or a phosphoric acid ($H_3PO_4$), or a combination thereof. The one or more phosphorus acids can be used in any suitable amount to achieve a desired result, such as, for example, 0.005 wt-% or greater, 0.01 wt-% or greater, 0.05 wt-% or greater, or 0.1 wt-% or greater. The upper amount of phosphorus acid should be selected to avoid unsuitable degradation to the surface of the plant item, the quality of the plant item, and/or the equipment of the processing line and should preferably factor in exposure duration. Typically, the phosphorus acid, if used, is present in pretreatment compositions in an amount of less than 5 wt-%, less than 1 wt-%, less than 0.05 wt-%, or less than 0.02 wt-%. The above acid concentrations reflect the amount of the acid itself, and not the combined amount of acid and solvent (water and/or organic solvent), if used, which may be present in the acid feedstock used to formulate the pretreatment composition. In some embodiments, other acids may alternatively or additionally be used, such as, for example, citric acid, maleic acid, or other acids that are commonly used in the processing of plant items (e.g., to assist in sanitizing), including edible fruits and vegetables.

The perishable plant item to be coated may also be subjected to one or more sanitization steps prior to coating, simultaneous to coating, after coating, or combinations thereof. Chemical sanitization, non-chemical sanitization, or combinations thereof, may be used. Examples of non-chemical sanitization include, for example, application of ultraviolet (UV) light (e.g., with wavelengths from 100 to 400 nanometers) to the plant item such as, for example, non-ionizing artificial UV-C light (100 to 280 nanometers wavelength, preferably 200 to 280 nanometer wavelength for enhanced antimicrobial effect). Other forms of sterilizing irradiation may also be used, if desired. For example, three sources of radiation are approved by the FDA for use on a variety of foods: gamma ray, x-ray, and electron-beam, although labeling requirements may apply and also render the treated foods ineligible for organic status. When used, such sanitization steps are preferably of a duration and/or intensity to substantially reduce (e.g., reduce by at least 50%, at least 75%, at least 90%, at least 95%, or at least 99%) or appreciably eliminate one or more of: (i) the overall microbial load of *Escherichia coli*, if any is present, (ii) the overall microbial load of *Salmonella*, if any is present, or (iii) the overall microbial load of other harmful bacteria or fungus, if any is present (e.g., "gray mold" such as that belonging to the *Botrytis* genus such as *Botrytis cinerea*). A reduction in such microbial loads is in the context of a reduction of viable cell counts present. Standard cell count techniques may be used in such quantitation.

Typically, the pretreatment composition will be water-based, but it may optionally contain organic solvent (e.g., any of those disclosed herein such as ethanol), and may even be organic-solvent-based in some embodiments. The pretreatment composition may even include any of the polyvalent metal crosslinking agents (PMCAs) disclosed herein (e.g., in any of the concentrations disclosed herein), which may function, for example, as an adhesion promoter to improve adhesion of the coating and/or improve one or more other properties of the coating (e.g., via facilitating and/or enhancing crosslinking of the coating). The pretreatment composition may include one or more adhesion promoter compounds such as, for example, certain phosphorus-containing compounds such as, for example, phosphorus acid and other suitable phosphorylated compounds. At least for inedible plant items, as well as perhaps on inedible skins of fruit or vegetables assuming the compound does not pose an unsuitable risk to edible portions of the fruit or vegetable, certain silicon-containing adhesion promoter compounds (e.g., silane coupling agents such as, for example, those used in food or beverage packaging coatings—see, e.g., U.S. Pat. No. 9,163,151) may also be used in an efficacious amount for improving coating adhesion.

The surface of the plant item to be coated may also be plasma treated to, for example, mildly etch the plant skin as described above and/or lower its surface energy. As previously discussed, plasma treatment in the form of high voltage cold plasma (HVCP) treatment is known for use with fruits and vegetables for purposes of its antimicrobial effect. See, for example, the materials, processes, and equipment disclosed in U.S. Pat. Nos. 10,194,672, 9,363,880, and WO2017200930. Thus, sanitizing may also be a benefit of plasma treatment and it may be used for that purpose as well, in addition to or instead of modifying adhesion and/or surface energy. In some embodiments, however, the particular plasma treatment is selected to achieve a desire level of etching and/or surface energy modification of the plant skin. In this regard, plasma etching or cleaning processes known for such purposes (with respect to metal or plastic substrates) in the industrial coating space may, for example, be employed, with appropriate modifications due to the differing nature of the plant skins to be treated. Surface energy modifications resulting from plasma treatment may be temporary.

Figure 4:
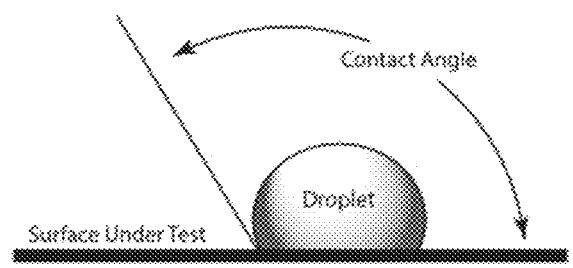
FIG. 4 illustrates measurement of contact angle of a droplet on a surface.

In some embodiments, suitable plasma treatment, or any other surface pretreatment preferably effective to increase surface energy of a plant surface, including any of the other pretreatment methods disclosed herein such as, e.g., acid etching, results in a measurable decrease in the contact angle of a droplet of deionized water relative to the plant surface (e.g., a decrease in such contact angle of at least 1°, at least 2°, at least 3°, at least 4°, at least 5°, at least 6°, at least 7°, at least 8°, at least 9°, at least 10°, at least 11°, at least 12°, at least 13°, at least 14°, or 15° or more). FIG. 4 is a representative diagram illustrating measurement of contact angle of a droplet of deionized water on a surface (e.g., fruit or vegetable skin). As depicted, in one embodiment, the contact angle is measured based on a line that is tangent to the surface of a droplet at the point that the droplet contacts a supporting substrate ("surface under test" in FIG. 4). In other embodiments, contact angle may be measured differently—for example, a droplet may be placed on a test surface and the test surface may be tilted in different directions; an advancing angle may be measured at the "front" of the droplet as it begins moving along the tilted surface; a receding angle may be measured at the "back" of the droplet when it begins moving in the opposite direction when the tilt of the test surface is reversed. Other techniques may be employed for measuring contact angle.

An optical tensiometer and image analysis software may be used to precisely determine the contact angle of the droplet relative to the surface being tested. An example of a useful optical tensiometer equipped with image analysis software is the DCA-100 contact angle tensiometer manufactured by First Ten Angstroms, Inc. of Portsmouth, Va., USA. Such an optical tensiometer may be used, for example, to measure the static contact angle of a 10-microliter sessile drop of room temperature deionized water (or other liquid to be tested) measured 30 seconds after application at room temperature. Unless specifically indicated otherwise, all contact angles referenced herein are static contact angles (as, opposed, e.g., to dynamic contact angles such as advancing or receding contact angles). Typically, contact angles are reported as the average value of at least six separate measurements.

Coating

With continued reference to FIG. 3, plant items—after being pretreated in the pretreatment area 324—may be conveyed to a coating area 336. Coatings may be applied various ways and any suitable coating application method may be used. For example, in some embodiments, plant items may pass through a curtain applicator 339 (e.g., one in which a liquid coating composition is applied as a spray or "sheet" of liquid). As another example, coatings may be applied via a coating bath 342. As another example, coatings may be applied (e.g., in the case of round or cylindrical plant items) by rollers 345 that transfer coating material that may be applied by sprayers 348 or by other means, to plant items that pass over and through the rollers. As another example, coatings may be sprayed onto the plant items by sprayers 351A and 351B. The compositions (e.g., barrier coating compositions or wash compositions) of the present description may be sprayable to facilitate application. In some embodiments, all, or substantially all, of the surfaces of the plant item may be effectively coated using applicator(s) located in substantially a single direction relative to the conveyor (e.g., such as from above) by rolling, tumbling, or otherwise rotating the plant item. (See, e.g., the rolling conveyors described in WO2019/028043 (Holland et al.) or WO2020/023319 (Hegel et al.).) In some embodiments, such as embodiment 352, multiple sprayers may facilitate application of different kinds of coatings on different parts of the plant item, or coatings with different thickness.

Coating variation may be implemented in other embodiments in other ways. For example, an automated conveyor 354 for the plant items may be accelerated or decelerated through a curtain applicator 339; the amount of coating or makeup of that coating dispensed by a curtain applicator 339 could be varied; the speed of rollers 345 could be increased or decreased, thereby adjusting the amount or time of contact with rollers 345 configured to transfer coating material to plant items as they pass; speed of travel through a bath could be varied; etc.

As already discussed, in certain preferred embodiments, the applied coating compositions yield hardened clear, or at least substantially clear coatings. Preferred such coatings are free of eye-visible haze (i.e., haze visible to the unaided human eye under typical representative viewing conditions). In some embodiments, the hardened coating is at least substantially free of haze in testing pursuant to ASTM D1003-13, Procedure A (e.g., a haze value of less than 20%, less than 10%, less than 5%, less than 2.5%, or less than 1%). The hardened coating is preferably free of particulates and agglomerates visible to the unaided (20/20) human eye. In some embodiments, the coating composition is preferably free, or substantially free, of particles having a maximum dimension of greater than about 50 microns, greater than about 30 microns, greater than about 20 microns, greater than about 15 microns, greater than about 10 microns, greater than about 5 microns, greater than about 1 micron, or greater than about 0.1 microns.

In some embodiments, the hardened coatings are sufficiently optically transparent so as to prevent the coatings from being detectable by the human eye. For example, the coatings can have an average transmittance of at least about 60%, at least about 65%, at least about 70%, at least about 80%, at least about 85%, at least about 90%, at least about 95%, or at least about 99% for light in the visible range such as, e.g., sunlight (i.e., the portion of the solar spectrum having a wavelength between 400 nanometers and 700 nanometers). As used herein, "transmittance" is defined as the ratio of transmitted light power to incident light power. As used herein, "average transmittance" refers to the average value of the transmittance over the entire area of the coating. Because transmittance typically decreases with coating thickness, the hardened coatings can be made thin enough to allow for sufficient transmittance of visible light while still preferably being thick enough to serve as a barrier to mass/moisture loss, as previously described. An example of a useful test method for determining light transmittance is ASTM D1003-13, Procedure A.

The thickness of the hardened coating employed may vary depending upon, for example, the plant item to be coated, the desired aesthetic properties of the coating, cost considerations, and the desired level of coating performance. In some embodiments, the coating will be of substantially uniform thickness. Examples of typical dry coating thickness include average thicknesses of less than about than about 75 microns, less than about 20 microns, less than about 15 microns, less than about 10 microns, less than about 9 microns, less than about 8 microns, less than about 7 microns, less than about 6 microns, less than about 5 microns, less than about 4 microns, less than about 3 microns, less than about 2 microns, or less than about 1.5 microns. The coating will typically be used at an average dry coating thickness of at least about 0.01 micron, at least about 0.100 micron, at least about 0.5 micron, at least about 1 micron, at least about 1.5 microns, at least about 2 microns, at least about 2.5 microns, or at least about 3 microns.

In some embodiments, it may be desirable to employ a coating on a plant item having a non-uniform coating thickness throughout. For example, it may be desirable to have two or more hardened coating portions having different average coating thickness. In some embodiments, at least a portion of the hardened coating is at least 5%, at least 10%, at least 15%, at least 20%, at least 25%, at least 50%, at least 75%, or 100% or more or even 200% or more thicker than the coating thickness present on other portions of coated perishable item. For example, a thicker coating portion may be selectively positioned over portions of a plant item that are more prone to damage (e.g., bruising or abrasion) and/or more susceptible to spoilage initiation. In some embodiments, the selectively applied coating is applied on and/or around a stem portion of a perishable plant item (e.g., a stem and/or calyx button of a fruit such as an avocado). While not intending to be bound by theory, it has been observed that for certain fruits (e.g., avocados), over-ripening and spoilage tends to occur first in portions of the plant flesh adjacent to the stem area. In the case of avocados, this may be due, at least in part, to the transition/interface between the fruit skin and the stem area and, for example, shrinkage of the skin which may open up a gap in the interface area and allow for increased ingress of oxygen, water vapor, ethylene gas, and/or microbial agents (e.g., biotic stressors). Although not presently preferred, it is also contemplated that, in some embodiments, coating composition may be selectively applied to one or more portions of a plant item (e.g., that are relatively more susceptible to spoilage and/or spoilage initiation), with one or more other portions left uncoated to minimize the overall amount of applied coating and save on material costs.

In addition to, or as an alternative to a thicker coating portion, a chemically-different coating (i.e., from other coating portion(s)) may be selectively applied on a portion of a perishable item such as, for example, a portion of a plant item (e.g., freshly harvested fruit or vegetable) that is relatively more susceptible to damage or spoilage initiation. As compared to one or more other coating composition applied on the plant item, the selectively applied chemically-different coating composition may, for example, yield a coating have an increased barrier property relative to oxygen, carbon dioxide, and/or water vapor transmission; include an increased amount of antimicrobial agent; include an increased amount of ripening inhibitor; yield a coating have an increased abrasion resistance; yield a coating having an increased mechanical strength (e.g., tensile strength); yield a coating having an increased flexibility; yield a coating with a different ripening time; yield a coating with a different appearance (e.g., color, glossiness, etc.); or any combination thereof. In some embodiments, one or more additional layers of the coating composition are selectively applied on one or more portions of the perishable item to achieve the thicker dry coating thickness. The one or more additional layers may be formed using a same or a chemically-different coating composition than: (a) that used to provide a base coating layer over which the one or more additional layers are disposed and/or (b) that used to provide a topcoat layer applied over the one or more additional layers. Thus, in some embodiments, the one or more additional layers of coating are applied first to the perishable item. The one or more additional layers may be applied at any suitable point or time in the supply chain. For example, for fresh produce, the one or more additional layer may be applied at a fruit or vegetable processor as part of a fruit or vegetable packing process.

Hardened coatings of the present description are preferably capable of reducing the mass loss of perishable items over a commercially pertinent time period, and particularly plant items such as fresh fruits and vegetables, cut flowers, and plant cuttings. For example, hardened coatings of the present description preferably reduce the mass loss rate of a given perishable plant item by at by at least: 10%, 15%, 20%, 25%, 30%, 35%, 40%, 45%, 50%, 55%, 60%, 65%, 70%, 75%, 80%, 85%, or 90% or greater compared to untreated analogous perishable plant items. As used herein, the term "mass loss rate" refers to the rate at which the product loses mass (e.g., by releasing water and other volatile compounds). The mass loss rate is typically expressed as a percentage of the original mass per unit time (e.g., percent per day) and may be determined by weighing a coated perishable plant item at different time points. Examples of pertinent time periods for assessing mass loss rate include just prior to coating (to establish a baseline mass for the uncoated perishable), immediately after coating and hardening of the coating composition (to establish a baseline mass for the coated perishable item such that the hardened coating weight can be determined), 24 hours after coating, 48 hours after coating, 72 hours after coating, 96 hours after coating, 120 hours after coating, 7 days after coating, 10 days after coating, 14 days after coating, 21 days after coating, and 28 days after coating. The pertinent time periods for assessing mass loss rate may vary widely depending upon the particular perishable item coated. For example, an overall testing time period for mass loss rate may be much longer for relatively long shelf-life perishables such as fresh avocados compared to relatively short shelf-life perishables such as fresh strawberries. Useful freshly harvested plant items for assessing mass loss of coating compositions include any of those disclosed herein, and especially avocados, blueberries, cherries, strawberries, lemons, limes (e.g., finger limes), and spring greens.

Hardened coatings of the present description preferably exhibit a mass loss factor of at least 1.1, at least 1.2, at least 1.3, at least 1.4, at least 1.5, at least 1.6, at least 1.7, at least 1.8, at least 1.9, at least 2.0, at least 2.2, at least 2.4, at least 2.6, at least 2.8, at least 3.0. As used herein, the term "mass loss factor" is defined as the ratio of the average mass loss rate of uncoated produce (measured for a control group) to the average mass loss rate of the corresponding coated produce at a given time. Hence a larger mass loss factor corresponds to a greater reduction in average mass loss rate for the coated produce.

In preferred embodiments, hardened coatings of the present description are preferably capable of reducing the occurrence of microbial infection (e.g., bacterial and/or fungal) of perishable items over a commercially pertinent time period, and particularly plant items such as fresh fruits and vegetables, cut flowers, and plant cuttings. For example, hardened coatings of the present description are preferably capable of reducing the infection occurrence rate (e.g., of gray mold) of a given batch of coated similarly situated plant items over a given time period by at least 10%, 15%, 20%, 25%, 30%, 35%, 40%, 45%, 50%, 55%, 60%, 65%, 70%, 75%, 80%, 85%, or 90% or greater compared to untreated similarly situated plant items from the same batch.

In preferred embodiments, hardened coatings of the present description are preferably capable of reducing the rate of softening for a treated fresh fruit or vegetable over a commercially pertinent time period for the fruit or vegetable (e.g., 3 days, 7 days, 10 days, 14 days, 21 days and the like). For example, hardened coatings of the present description are preferably capable of reducing the rate of softening of a given batch of coated similarly situated fruit or vegetable over a given time period by at least: 10%, 15%, 20%, 25%, 30%, 35%, 40%, 45%, 50%, 55%, 60%, 65%, 70%, 75%, 80%, 85%, or 90% or greater compared to untreated similarly situated plant items from the same batch.

In preferred embodiments, hardened coatings of the present description are preferably capable of reducing the rate of discoloration for a treated fresh fruit or vegetable over a commercially pertinent time period for the fruit or vegetable (e.g., 3 days, 7 days, 10 days, 14 days, 21 days and the like). For example, hardened coatings of the present description are preferably capable of reducing the rate of discoloration of a given batch of coated similarly situated fruit or vegetable over a given time period by at least: 10%, 15%, 20%, 25%, 30%, 35%, 40%, 45%, 50%, 55%, 60%, 65%, 70%, 75%, 80%, 85%, or 90% or greater compared to untreated similarly situated plant items from the same batch.

In another aspect, the present description provides methods, equipment, and systems for selecting or modifying a coating composition (e.g., any of those disclosed herein) based on one or more observed (e.g., measured) characteristics of a plant item. Such an approach allows for better tailoring of the properties of the coating composition to the type and/or condition (e.g., level of ripeness) of the plant item to be coated. In so doing, a better outcome can be achieved (e.g., enhanced shelf-life, enhanced aesthetics, enhanced flavor profiles, and the like) for the coated plant item as compared to a conventional coating process that utilizes, for example, a single fixed coating composition. In addition, the amount of applied coating material can be optimized for cost-savings by only applying the amount of coating composition required to achieve the desired result.

A non-limiting discussion relating to examples of materials for use in formulating coating compositions for use with the treatment method, equipment, and systems described herein is provided below. Additional disclosure regarding suitable coating ingredients and coating compositions, and methods relating thereto, is provided in International application No. PCT/US2021/036270 entitled "Barrier Coating Compositions, Wash Compositions, and Other Compositions for Perishables and Methods, Systems, Kits, and Coated Items Relating Thereto," filed on Jun. 7, 2021 by DeMaster et al (as well as any of those referenced herein). In preferred embodiments, the coating composition is formulated such that it does not negatively impact the ability to label the treated plant item (when, for example, edible produce) as being "organic" and/or "vegan". Moreover, in preferred embodiments, the coating composition is not formulated using any ingredients from feedstocks derived from petroleum. Thus, in preferred embodiments, all of the organic compounds present in the coating composition originate from bio-sourced feedstocks. Accordingly, in some embodiments, each and every one of the organic compounds (i.e., carbon-containing compounds) present in the coating composition has at least about 1.5 dpm/gC (disintegrations per minute per gram carbon) of carbon-14, more preferably at least 2 dpm/gC, most preferably at least 2.5 dpm/gC, and especially at least 4 dpm/gC. Carbon-14 levels can be determined by measuring its decay process (disintegrations per minute per gram carbon or dpm/gC) through liquid scintillation counting). In preferred embodiments, the coating composition is also not intentionally formulated using any ingredients commonly recognized as food allergens.

Any suitable coating composition may be used. However, preferred coating compositions include one or more of a lipid, an oligosaccharide, a polysaccharide, a peptide, an oligopeptide, or a polypeptide. For purposes of convenience, oligopeptides and polypeptides are referred to collectively herein as "polypeptides" and oligosaccharides and polysaccharides are referred to herein collectively as "polysaccharides". Lipids tends to help impart hydrophobicity properties to coatings, which is desirable for coatings on perishable plant items, for example, to help resist water vapor permeation and, therefore, mass loss of the coated perishable item due to water loss. Examples of lipids include fatty acids, fatty acid salts, glycerides (e.g., mono- and di-glycerides), fatty acid esters others glycerides (e.g., a fatty acid monoester of ascorbic acid or a salt thereof), oils (e.g., triglycerides), phospholipids, glycolipids, sterols, and waxes. Such hydrophobicity may also help resist premature washing away of the coating. Polysaccharides and polypeptides tend to help impart good mechanical properties to coatings, but can sometimes suffer from poor barrier properties, especially with respect to water. Thus, in some embodiments, coating compositions employed in methods of the present disclosure are "hybrid" compositions that include: (i) both one or more lipids and one or more polysaccharides, optionally further one or more polypeptides or (ii) one or more polysaccharides and one or more polypeptides, optionally further one or more lipids. If desired, in certain preferred embodiments, crosslinking may be used, for example, to increase the mechanical properties of lipid-based coatings, the barrier properties of polypeptide- and/or polysaccharide-based coatings, and one or both of the barrier and/or mechanical properties of hybrid barrier coatings.

In certain preferred embodiments, the coating composition includes one or more fatty acids, one or more fatty-acid-containing monoesters (e.g., a monoester of glycerol and a fatty acid, also referred to as a "mono-glyceride"), one or more non-wax fatty acid esters other than mono-glycerides, or a combination thereof. In some embodiments, such materials constitute more than 50 wt-%, more than 75 wt-%, or more than 90 wt-% of the total solids in the coating composition. Examples of preferred mono-glycerides include 2,3-dihydroxypropyl palmitate, 1,3-dihydroxypropan-2-yl palmitate, 2,3-dihydroxypropyl stearate (e.g., CAS Registry No. 123-94-4), 1,3-dihydroxpropan-2-yl stearate (e.g., CAS Registry No. 621-61-4), mono-laurin, and mixtures thereof. The EDIPEEL product commercially available from Apeel Sciences of Goleta, Calif. is an example of a suitable mono-glyceride-based coating composition for use, e.g., as a base coating composition in preferred methods of the present disclosure. According to GRAS Notice No. 648 the EDIPEEL product is a mixture of mono-glycerides and primarily contains 2,3-dihydroxypropyl palmitate and 1,3-dihydroxypropan-2-yl palmitate. Further examples of fatty acids or fatty acid monoglycerides or monoesters that may be used are disclosed in WO2020/051238 (by Braden et al.), including, for example, any of the depicted formulas or structure therein (see, e.g., Formula 1 in claim 1 or 2 and the specific compounds depicted in claim 12 or 18).

In some embodiments, the coating composition includes one or more esters of a fatty acid and a hydroxyl-functional compound other than glycerol, where the overall ester compound includes one or more, preferably two or more, more preferably three of more active hydrogen groups (e.g., hydroxyl group(s)). Preferably, the fatty acid ester of a hydroxyl-functional compound other than glycerol includes an active hydrogen group capable of forming a salt (e.g., a carboxyl group or an acidic hydroxyl group), with such group preferably located on a structural unit derived from the hydroxyl-functional compound other than glycerol. The hydroxyl-functional compound is preferably one or both of: i) more polar than glycerol and (ii) more soluble in water than glycerol. The hydroxyl-functional compound other than glycerol may be saturated or unsaturated and preferably has three or more active hydrogen groups, more preferably four or more (e.g., for our more hydroxyl groups). Ascorbic acid, or a salt thereof, is a preferred example of such a hydroxyl-functional compound other than glycerol. The fatty acid ester of a hydroxyl-functional compound other than glycerol, which may optionally be a salt (e.g., an ammonium salt), may be derived from any suitable saturated or unsaturated fatty acid, or combination thereof, although typically the fatty acid(s) will be a C12 or higher fatty acid. Typically, and especially in water-based coating embodiments, the ester is derived from a C20 or lower fatty acid, preferably C18 or lower, more preferably C12, C14, or C16 or C18, or a combination thereof. Although the fatty acid ester of a hydroxyl-functional compound other than glycerol can may be a di- or tri-ester (e.g., of ascorbic acid or a salt thereof), monoesters are preferred. Preferred such monoesters include ascorbyl laurate, ascorbyl myristate, ascorbyl palmitate, ascorbyl stearate, a salt thereof (e.g., an ammonium salt of ascorbyl palmitate and/or an ammonium salt of ascorbyl stearate), or a combination thereof. The coating composition can include any suitable amount of one or more such monoesters. In some embodiments, more than 50 wt-%, more than 60 wt-%, more than 70 wt-%, more than 80 wt-%, more than 90 wt-%, more than 95 wt-%, more than 99 wt-%, or up to about 100 wt-% of the lipid (or the total solids) present in the coating composition is a mono-, di-, and/or tri-ester (more preferably a monoester) of a fatty acid and a hydroxyl-functional compound other than glycerol.

Examples of polypeptides for use in coating compositions may include gelatin, zein, globulin, albumin, whey protein, casein, hemp protein, brown rice protein, alfalfa protein, chia protein, pea protein, flax protein, silk fibroin, soy protein, other protein isolates, or mixtures thereof. For edible embodiments containing one or more polypeptides, polypeptides that are not common food allergens are preferred (e.g., casein, whey protein, and soy protein are common food allergens). Examples of silk fibroin and suitable coating compositions including silk fibroin are provided in U.S. Publ. No. 2020/0178576. In some embodiments, an amphiphilic polypeptide is used. In some embodiments, preferred polypeptides are carboxyl-functional polypeptides such as those containing, and more preferably rich in, structural units provided by amino acids such as aspartic acid and/or glutamic acid. In some embodiments, preferred polypeptides are amino- are amide-functional polypeptides such as those containing, and more preferably rich in, structural units provided by amino acids such as arginine, asparagine, glutamine, histidine, lysine, and combinations thereof.

Examples of polysaccharides for use in coating compositions may include pectin, agarose, agaropectin, alginate, carrageenan, arabinoxylan, chitosan, *psyllium*, carboxy methyl cellulose, hyaluronic acid, dextrin, salts or derivatives thereof, and mixtures thereof. Pectin is an example of a preferred polysaccharide. Polysaccharides included in the coating compositions of the present disclosure can include any suitable functional groups including, for example, one or more, two or more, or three or more selected from hydroxyl groups, carboxyl groups (or salts or alkyl esters thereof), amine groups, and amide groups. Carboxyl-functional polysaccharides are preferred in some embodiments such as, for example, polysaccharides having any of the acid number disclosed herein.

The pectin used may be either high methoxy ("HM") pectin having a degree of esterification ("DE") of 50 or above (e.g., 60 or above, 70 or above, 80 or above, etc.) or low methoxy ("LM") pectin having a DE of less than 50 (e.g., less than 40, less than 30, less than 20, less than 10, etc.), or a mixture thereof. The pectin may also be either amidated or non-amidated, or a mixture thereof. While not intending to be bound by theory, an advantage of using pectin is that it can provide a clean mouth feel (e.g., as opposed to a slimy mouth feel), as well enable crosslinking, for example, via the presence of active hydrogen groups. Preferred pectins for use in food-contact and/or edible embodiments of the present disclosure are derived from edible feedstocks (e.g., apple pomace, citrus peels, plums, or gooseberries).

In some embodiments, the coating composition includes (a) one or more monoesters, typically one or more fatty acid monoesters, more typically one or more mono-glycerides and/or one or more fatty-acid-monoesters of ascorbic acid or a salt thereof and (b) one or more fatty acids and/or salts thereof. In some such embodiments, the coating composition includes more than 50 wt-% of (a), based on the combined weights of (a) and (b). For example, the coating composition can include (a) from 50 to 99 wt-% (e.g., 60 to 95 wt-% or 70 to 90 wt-%) of one or more of a first group of compounds selected from one or more monoesters of fatty acids (e.g., fatty acid mono-glycerides) and (b) from 1 to 50 wt-% (e.g., 5 to 40 wt-% or 10 to 30 wt-%) of one or more of a second group of compounds selected from one or more fatty acid salts, based on the total combined weight of components (a) and (b). In other such embodiments, the coating composition include more than 50 wt-% of (b) (e.g., from 50 to 99 wt-%, 60 to 95 wt-% or 70 to 90 wt-% of (b)), based on the combined weights of (a) and (b). When present, the total combined amounts of components (a) and (b) in the coating composition typically comprises at least 50 wt-%, at least 60 wt-%, at least 70 wt-%, at least 80 wt-%, at least 85 wt-%, at least 90 wt-%, at least 95 wt-%, at least 96 wt-%, at least 97 wt-%, at least 98 wt-%, at least 99 wt-%, or at least 99.9 wt-% of the total solids present in the coating composition.

In certain preferred embodiments, the coating composition includes less than 10 wt-%, less than 5 wt-%, or less than 1 wt-%, if any, of diglycerides, based on the weight of total solids present in the coating composition.

In some embodiments, the coating composition includes less than 10 wt-%, less than 5 wt-%, or less than 1 wt-%, if any, of triglycerides, based on the weight of total solids present in the coating composition. In some embodiments, the coating composition includes less than 20 wt-%, less than 10 wt-%, less than 5-wt-%, or less than 1 wt-%, if any, of waxes (e.g., monoesters of fatty acids and fatty alcohols such as, for example, carnauba wax, plant-based paraffin wax, and the like, which typically do not include any active hydrogen groups), based on the weight of total solids present in the coating composition. In some embodiments, the coating composition, based on total solids, includes at most 10 wt-%, at most 5 wt-%, at most 2 wt-%, at most 1 wt-%, or at most 0.1 wt-%, if any, compounds having an alkyl chain of 26 or more. In some embodiments, the coating composition, based on total solids, includes at most 10 wt-%, at most 5 wt-%, at most 2 wt-%, at most 1 wt-%, or at most 0.1 wt-%, if any, monoester compounds not having an active hydrogen group (e.g., monoesters of a fatty acid and fatty alcohol).

In preferred embodiments, the coating composition includes one or more active hydrogen groups. While not intending to be bound by any theory, the presence of active hydrogen groups can provide various benefits including, for example, polarity, hydrophilicity, water-dispersibility (e.g., neutralized acid or base groups), hydrogen bonding sites or other preferential interactions (e.g., other Van der Waals bonding), and/or cross-linking sites. Examples of suitable active hydrogen groups include carboxyl groups (or anhydride groups); hydroxyl groups; amine groups (typically primary or secondary amine groups); or any other suitable active hydrogen group having a hydrogen attached to an oxygen atom (O), sulfur atom (S), or nitrogen (N) atom such as, for example, in the groups: —SH, =NH, —S(=O)$_2$(OH), —S(=O)OH; acid groups including P, O, and H such as phosphonic or phosphinic groups; salt groups thereof (e.g., base-neutralized acid groups); or any combination thereof. Hydroxyl groups (including salt groups formed from acidic hydroxyl groups) and carboxyl groups (including salt groups formed from carboxyl groups such as base-neutralized carboxyl groups) are particularly preferred. In some embodiments, the coating composition includes two or more different active hydrogen compounds such as for, example, one or more carboxyl groups or salts thereof and one or more hydroxyl groups. The coating composition may also include one or more functional groups other than active hydrogen groups such as, for example, oxirane groups or carbon-carbon double bonds (preferably aliphatic carbon-carbon double bonds). In some embodiments, one or more active hydrogen groups and/or other functional groups present assist with crosslinking of the coating composition. For convenience, compounds including one or more active hydrogen groups are referred to hereinafter as an "active hydrogen compound".

In some embodiments, the coating composition includes a first active hydrogen compound having one or more, more typically a plurality of cationic groups (e.g., —NH$_3^+$ or =NH$_2^+$) and a second active hydrogen compound having one or more, more typically a plurality of anionic groups (e.g., —COO$^-$). In polypeptides, cationic groups may be provided, for example, by structural units derived from arginine, histidine, and lysine and anionic groups from structural units derived from aspartic acid and glutamic acid. In some embodiments, the coating composition of the present disclosure includes (i) a polysaccharide having anionic groups and a polypeptide having cationic groups and/or (ii) a polysaccharide having cationic groups and a polypeptide having anionic groups. For example, one such combination is pectin having carboxylate anionic groups and a polypeptide having, for example, structural units with cationic groups formed from arginine, histidine, and/or lysine. While not intending to be bound by theory, it is believed that pairing of such anionic and cationic groups can lead to beneficial electrostatic complexation, for example, between a polypeptide having cationic groups and a polysaccharide having anionic groups, or vice versa, which can lead to improved coating properties.

In aqueous embodiments in which the coating composition includes carboxyl-functional groups, typically at least some (or all or substantially all) of the carboxyl-functional groups are neutralized with base. Any suitable base can be used, although in some embodiments it may be advantageous to use a fugitive base such as, e.g., a suitable nitrogen-containing volatile base. In embodiments intended for edible end uses, the one or more bases used are preferably safe for use as a direct food-additive (e.g., a base recognized as Generally Recognized as Safe, "GRAS", by the FDA).

Examples of suitable fugitive bases include ammonium hydroxide (resulting in ammonia), amines (e.g., morpholine, dimethylethanolamine, and the like), and combinations thereof. In some embodiments, the one or more base is a metallic salt (e.g., NaOH, KOH, $Ca(OH)_2$, $Mg(OH)_2$, etc.), either alone or in combination with a fugitive base. In certain preferred embodiments, a base is used that forms a water-emulsifiable or water-soluble salt with a carboxyl-functional compound (e.g., a fatty acid having 7 or more, 8 or more, or 9 or more carbon atoms). Non-limiting examples of such bases include sodium bases (e.g., NaOH), potassium bases (e.g., KOH), and combination thereof, which may be optionally combined, for example, with non-metallic bases such as ammonia.

In some embodiments, the coating composition includes one or more unsaturated compounds, which may be mono-unsaturated, polyunsaturated, or a mixture thereof. Cis carbon-carbon double bonds are preferred. In some embodiments, the coating composition includes, if any, less than 1 wt-%, less than 0.1 wt-%, less than 0.01 wt-%, or less than 0.001 wt-% of material including one or more carbon-carbon double bonds in the trans configuration. Examples of preferred unsaturated compounds include unsaturated fatty acids and salts thereof, unsaturated glycerides (particularly mono-glycerides), and mixtures thereof. Preferred unsaturated fatty acids and unsaturated mono-glycerides include one or more or two or more cis carbon-carbon double bonds, and more preferably that are free of trans carbon-carbon double bonds. Examples of preferred cis configuration monounsaturated fatty acids include 9-cis-hexadenoic acid (also referred to as palmitoleic acid), 9-cis-octadenoic acid (also referred to as oleic acid), 13-cis-decosenoic acid (also referred to as erucic acid), and combinations thereof, with oleic acid being particularly preferred due to its ample supply and low cost. In some embodiments, for health benefits, it is advantageous to use one or more polyunsaturated fatty acids selected from omega-3-fatty acids, omega-6-fatty acids, or a mixture thereof—typically, one or more isomer of linoleic acid, one or more isomer of linolenic acid, or a combination thereof. In certain edible embodiments, it is preferred to use only isomers of linoleic acid and/or linolenic acid in which all of the carbon-carbon double bonds are in the cis configuration. Other suitable cis configuration polyunsaturated acids may include 5,8,11,14-all-cis-eicosatetraenoic acid (also referred to as arachidonic acid), eicosapentaenoic acid ("EPA", $C_{20}H_{30}O_2$), and docosahexaenoic acid ("DHA", $C_{22}H_{32}O_2$). Examples of preferred polyunsaturated fatty acids include a non-conjugated linoleic fatty acid (preferably a cis, cis isomer), a conjugated linoleic fatty acid (preferably a cis, cis isomer), an alpha-linolenic fatty acid (preferably a cis, cis, cis isomer), a gamma-linolenic fatty acid (preferably a cis, cis, cis isomer), isomers of any of these, or a combination thereof. Examples of feedstock sources of linoleic fatty acid include safflower, sunflower, soya, rapeseed, and canola. Examples of feedstock sources of linolenic acid include flaxseed, walnut, chia, hemp, rapeseed, canola, and *perilla*. Any of the above fatty acids may be used direct as fatty acids, as fatty acid salts, and/or as the fatty acid portion of a mono-glyceride.

Coating compositions of the present disclosure can exhibit any suitable iodine value. In preferred embodiments, the coating composition exhibits an iodine value, if any, of less than 250, less than 200, less than 150, less than 100, less than 70, less than 50, less than 40, less than 30, less than 20, less than 15, less than 10, less than 5, or less than 1 centigrams of iodine per gram of solids in the coating composition. In some embodiments, a coating composition is used that has an iodine value of greater than 0.1, greater than 1, greater than 2, greater than 3, greater than 4, greater than 5, greater than 6, greater than 7, greater than 8, greater than 9, greater than 10, greater than 15, greater than 20, greater than 30, greater than 40, greater than 50, greater than 60, greater than 70, greater than 80, or greater than 90 or greater than 100, greater than 120, or greater than 150 centigrams iodine per gram of solids in the coating composition. An example of a suitable iodine value test is provided in International application No. PCT/US2021/036270 entitled "Barrier Coating Compositions, Wash Compositions, and Other Compositions for Perishables and Methods, Systems, Kits, and Coated Items Relating Thereto," filed on Jun. 7, 2021 by DeMaster et al., the contents of which are incorporated herein by reference in their entirety. In some embodiments, the presence of unsaturated carbon-carbon double bonds may be advantageous for coating crosslinking purposes. In some such embodiments, the amount of unsaturated compounds present in an applied coating composition is based on one or more sensed parameters associated with the plant item(s) to be coated.

In some embodiments, the coating composition preferably includes one or more compounds capable of preferentially interacting or associating with another component of the coating composition such as, for example, via a functional group (e.g., an active hydrogen group) present on the component, which preferably results in one or more desirable coating properties when enough such interactions occur. For example, the interaction or association can be a covalent bond formation, an ionic interaction (e.g., an ionic bond formation such as a salt bridge), or another type of association (e.g., Van der Waals bonding) that may optionally, and preferably in some embodiments, be reversible. For example, in certain preferred embodiments, the coating composition includes one or more compounds capable of coordinating, complexing and/or chelating (hereinafter "coordinating" for brevity) with one of more active hydrogen compounds via, for example, one or more active hydrogen groups such as salts of carboxyl groups (e.g., carboxylates). Examples of such compounds include polyvalent metal compounds. Preferred polyvalent metal compounds are capable of entering into a "crosslinking" reaction, which is reversible in some embodiments. While not intending to be bound by theory, in some embodiments, the crosslinking reaction may be a coordination or chelation that does not result in a covalent linkage. For convenience, herein the polyvalent metal compound is referred to as a "polyvalent metal crosslinking agent" or "PMCA" for short.

In some embodiments, the PMCA is present in one or more modifier compositions used to modify a base treatment composition. Such a multi-part methodology avoids potential pot-life storage stability issues and allows for an optimized amount of PMCA to be included in the treatment based on sensed data associated with the perishable items to be treated.

In certain preferred embodiments, the PMCA includes a metal atom, such as, e.g., a transition metal atom, in a form (e.g., an oxidation state) capable of coordinating with an active hydrogen group (e.g., a carboxylic acid or carboxylate group) under ambient conditions (e.g., 25° C. and 50% relative humidity) to form a reversible crosslink.

Preferred PMCAs include a polyvalent metal atom such as bismuth (Bi), calcium (Ca), cobalt (Co), iron (Fe), magnesium (Mg), manganese (Mn), zinc (Zn), or a combination thereof. Although edible PMCAs are preferred, it is within the scope of the invention, in for example embodiments in which the coating composition is not intended for human consumption, to use PMCAs including polyvalent metals such as, for example, beryllium, cadmium, copper, zirconium, barium, strontium, aluminum, antimony, nickel, tin, tungsten, and the like. The polyvalent atom is preferably present in the PMCA in a form (e.g., an oxidation state) that facilitates crosslinking with one or more active hydrogen compounds. Although the PMCA can be of any suitable form, it is typically a complex or an oxide of a polyvalent metal. Accordingly, the PMCA may be an organometallic compound, a fully inorganic compound, or a mixture thereof. In some embodiments, the PMCA is a salt. The PMCA may be either soluble or insoluble in water. When insoluble, the PMCA may be provided as finely divided powder, which may optionally be suspended or otherwise dispersed in liquid coating compositions. In some embodiments, the PMCA may be provided as a colloid.

In some embodiments, the PMCA is present in a complex, such as a salt, that includes an organic anion. Examples of such organic anions include salts of organic acids, which may be amino acids, such as, e.g., acetate, glutamate, formate, carbonate, bicarbonate, salicylate, glycollate, octoate, benzoate, gluconate, oxalate, lactate, and combinations thereof. In some embodiments, the PMCA includes an amino acid (e.g., glycine or alanine), which may be present in the PMCA as a bidentate ligand.

Zinc is a preferred polyvalent metal. Examples of suitable zinc-containing PMCA include zinc acetate, zinc carbonate, zinc chloride, zinc citrate, zinc hydroxide, zinc gluconate, zinc oxide, zinc picolinate, zinc stearate, zinc sulfate, salt solutions thereof (e.g., ammonia or amine salts such as zinc ammonium carbonate, zinc ammonium acetate, zinc ammonium citrate, and the like), or a derivative or combination thereof.

Examples of calcium-containing PMCA include calcium acetate, calcium carbonate, calcium chloride, calcium citrate, calcium hydroxide, calcium glycinate, calcium glycolate, calcium gluconate, calcium lactate, calcium oxide, calcium phosphate (e.g., calcium mono-phosphate), calcium pyrophosphate, calcium propionate, calcium pyruvate, calcium silicate, tricalcium silicate, calcium sorbate, calcium stearate, calcium sulfate, calcium acid pyrophosphate, a variant thereof (e.g., calcium lactate gluconate), or a derivative or combination thereof.

Examples of manganese-containing PMCA include manganese chloride, manganese citrate, manganese gluconate, manganese sulfate, base complexes thereof (e.g., amine or ammonia complexes thereof), or a derivative or combination thereof.

Examples of magnesium-containing PMCA include magnesium carbonate, magnesium chloride, magnesium hydroxide, magnesium oxide, magnesium phosphate, magnesium stearate, magnesium sulfate, or a derivative or combination thereof.

Examples of iron-containing PMCA include ferric ammonium citrate, ferric chloride, ferric citrate, ferric phosphate, ferric pyrophosphate, ferric sulfate, ferrous ascorbate, ferrous carbonate, ferrous citrate, ferrous fumarate, ferrous gluconate, ferrous lactate, ferrous sulfonate, or a derivative or combination thereof.

Examples of bismuth-containing PMCA compounds include multivalent bismuth salts of various anions, including bismuth salts of a metal oxyanion, bismuth salts of organic compounds, and the like. These compounds can include their anhydrous forms as well as various hydrates, including hemihydrate, pentahydrate, and other hydrated forms, along with mixtures and combinations thereof, and the like. Examples of bismuth-containing compounds include bismuth silicate, bismuth magnesium aluminosilicate, bismuth aluminate, bismuth borate, bismuth manganate, bismuth phosphate, bismuth aluminate, bismuth manganate, bismuth subcarbonate, bismuth subcitrate, bismuth citrate, bismuth titrate, bismuth gallate, bismuth subgallate, bismuth salicylate, bismuth subsalicylate, bismuth hydroxide, bismuth oxide, bismuth trioxide, bismuth nitrate, bismuth subnitrate, and the like, similar bismuth salts, and derivatives of combinations thereof. Bismuth subcitrate, bismuth subsalicylate, and combinations and derivatives thereof are preferred.

Examples of suitable cobalt-containing PMCA compounds include vitamin B12, also known as cobalamin. Other cobalt-containing compounds may also be used, for example, in certain embodiments in which the coating composition will not be directly consumed.

While not intending to be bound by theory, for embodiments in which the coating composition includes an active hydrogen compound including one or more acid salt groups (e.g., a base-neutralized carboxylic acid group) for "crosslinking" purposes, it is believed that it is advantageous to select a PMCA including an anion that is a stronger base than the anion of the acid salt group of the active hydrogen compound. Again, while not intending to be bound by theory, it is believed that if the PMCA employs an anion that is a weaker base than the anion of the acid salt group of the active hydrogen compound, then crosslinking will not occur, or at least not as effectively, between the PMCA and the acid groups present on the active hydrogen compound. In some embodiments, the conjugate acid of the anion of the PMCA is preferably either volatile or unstable. For example, acetic acid, the conjugate acid of acetate anion, is volatile, and carbonic acid, the conjugate acid of both bicarbonate and carbonate anion, is unstable (e.g., spontaneously decomposes to carbon dioxide and water). PMCA complexes containing bases are preferred in some embodiments, with fugitive bases such as, for example, ammonia and amines being particularly preferred. The bases may be used, for example, to solubilize the polyvalent metal or polyvalent metal complex.

In some embodiments, e.g., coating embodiments in which the coating is likely to be consumed, the PMCA is preferably itself edible (e.g., as a food-grade additive), with all the ingredients used to prepare the PMCA preferably being edible. In edible embodiments, the PMCAs preferably qualifies as a direct food-grade additive under U.S. Food and Drug Administration ("FDA") laws and regulations.

In some embodiments, the coating composition includes a plant extract (e.g., an extract of an edible portion of a plant such as, e.g., a fruit or vegetable). In some embodiments, some or all of the PMCA is supplied by the plant extract, which may be a cuticle extract (e.g., a fruit cuticle extract). In some embodiments, the plant extract is an extract from an edible portion of a plant and is itself also edible. For example, the plant extract can be a fruit extract, which may be produced from any suitable portion or portions of the fruit. Examples of suitable fruit extracts include extracts of tomatoes (e.g., tomato pomace), grapes (e.g., grape skins or pomace), cranberries (e.g., cranberry skins or pomace), apples (e.g., apple skins or pomace), pomegranates (e.g., pomegranate pomace or peel extract), blueberries (e.g., blueberry skins or pomace), or combinations thereof. Typically, the plant extract will have been processed to concentrate (e.g., on a total solids basis) the amount of PMCA and/or other crosslinking compounds (e.g., phenols such as polyphenols and other natural endogenous crosslinkers) present relative to the amount present in the unprocessed original plant material from which the plant extract was derived. The extract may also optionally have been processed to remove one or more undesired impurities or other compounds that may, for example, interfere with the desired crosslinking and/or cause one or more undesired organoleptic properties detectable to a typical human consumer. The plant extract may be processed such that the plant extract has concentrated levels of PMCA relative to the original plant material from which it was process such as, for example, 25% more concentrated, 50% more concentrated, 75% more concentration, 100% more concentrated, 200% more concentrated, 300% more concentrated, 400% more concentrated, and so on.

Any suitable portion of the PMCA may be provided by one or more plant extracts. In some embodiments, at least 10 wt-%, at least 20 t-%, at least 30 wt-%, at least 40 wt-%, at least 50 wt-%, at least 60 wt-%, at least 70 wt-%, at least 80 wt-%, at least 90 wt-%, at least 95 wt-%, or up to 100 wt-% of the PMCA is provided by the plant extract.

Any suitable amount of PMCA may be included in coating compositions of the present disclosure to achieve the desired result. In some embodiments, the amount of PMCA present in an applied coating composition is based on one or more sensed parameters associated with the plant item(s) to be coated. In some embodiments, the coating composition includes one or more PMCA in an amount in an amount of at least 0.1 wt-%, at least 1 wt-%, at least 3 wt-%, at least 7 wt-%, at least 10 wt-%, or at least 15 wt-%, based on the total amount of metal in the one or more PMCA relative to the nonvolatile weight of the coating composition. In some embodiments, the coating composition may include at least about 0.1, at least about 0.5, at least about 1, at least about 2, at least about 3, at least about 4, at least about 5, or at least about 10 moles of active hydrogen compound (e.g., moles of carboxyl-functional active hydrogen compound such as fatty acid and/or acid-functional biopolymer) per mole of polyvalent metal in the PMCA. In some embodiments, the coating composition includes less than about 10, less than about 5, less than about 4, less than about 3, less than about 2, less than about 1, or less than about 0.5 moles of active hydrogen compound (e.g., moles of carboxyl-functional active hydrogen compound such as fatty acid and/or acid-functional biopolymer) per mole of polyvalent metal in the PMCA. In some embodiments, the coating composition includes at least about 0.01, at least about 0.05, at least about 0.1, at least about 0.15, at least about 0.2, at least about 0.25, at least about 0.35, at least about 0.5, at least about 0.6, at least about 0.8, or at least about 1 moles (or equivalents) of the polyvalent metal per mole (or equivalent) of carboxyl groups or salt groups thereof present in the coating composition (e.g., per mole of carboxyl groups or salt groups thereof present in the one or more carboxyl-functional active hydrogen compounds such as fatty acids and/or acid-functional biopolymers). In some embodiments, the coating composition includes no more than about 2.0, no more than about 1.5, no more than about 1.0, no more than about 0.75, no more than about 0.70, no more than about 0.5, no more than about 0.45, no more than about 0.35, no more than about 0.3, or no more than about 0.2 moles of the polyvalent metal per mole of carboxyl groups or salt groups thereof present in the coating composition (e.g., per mole of carboxyl groups or salt groups thereof present in the one or more carboxyl-functional active hydrogen compounds such as fatty acids and/or acid-functional biopolymers).

To achieve enhanced coating properties such as, for example, enhanced mechanical properties and/or barrier properties, it may be advantageous to formulate a coating composition that incorporates two or more different modes of crosslinking. For example, in some embodiments, the coating composition may be capable of cross-linking via two or more of: (i) interaction of a PMCA compound and active hydrogen groups, (ii) via carbon-carbon double bonds, (iii) via natural crosslinking compounds present in a plant extract included in the coating composition, (iv) via purified or exogenous and/or synthetic crosslinking compounds (e.g., phenolic or polyphenol crosslinking compounds, preferably which are naturally occurring in plant materials, more preferably edible plant materials such as grape skins, such as ferulic acid, tannic acid, and the like optionally in combination with a suitable enzyme(s) to assist in crosslinking) and/or (v) via crosslinking enzymes (e.g., transglutaminase) included in the coating composition.

Sensing

As depicted in FIG. 3, in preferred embodiments, prior to being coated, plant items may pass through a sensing area 355 (e.g., the plant items may be conveyed through the sensing area 355 by an automated conveyor 356). In the sensing area 355, a plant item may be analyzed by one or more sensors that are configured to assess a characteristic of the plant item, such as, for example, a level of ripeness or overall quality of a fruit or vegetable. The sensed characteristics of the plant item may be converted by one or more sensors to a value or signal that can be analyzed by a coating algorithm or method (e.g., a computer-implemented algorithm or method) to selectively apply or modify a coating.

In some embodiments, one or more sensors are employed to determine an external property of the plant item (e.g., a size, a dimension, a shape, a mass, a volume, a density, an appearance, a color, the presence or absence of visual blemishes, etc.) and/or an internal property (e.g., composition, flavor, aroma, a concentration, presence or relative presence of interior defects, etc.). In some embodiments, a sensor comprises a gloss meter 357.

In some embodiments, one or more sensor could be an optical sensor, such as an image acquisition device 358 (e.g., a still and/or video camera). A sensor may be capable of providing an output indicative of a color parameter and/or other visible characteristic of the plant item (e.g., a color parameter indicative of a level of fruit or vegetable ripeness such as, for example, a hue angle). A sensor may comprise a spectrophotometer. In some embodiments, a sensor is configured to identify a type of fruit, vegetable, or other plant item.

In some embodiments, one or more sensor comprises an infrared sensor 360. In some embodiments, the infrared sensor is configured to measure infrared light reflected off the plant item (e.g., infrared light emitted by a near infrared reflectance (NIR) device and reflected from the plant item). For discussion of such sensors and sensing methods see, for example, U.S. Pat. No. 10,408,748 (Schwartzer et al.) and U.S. Pub. No. 2019/0340749 (Schwartzer et al.), each of which are incorporated by reference in its entirety.

In some embodiments, one or more sensors are configured to identify, measure, or both identify and measure a ripeness or quality parameter of a plant item. For example, in some embodiments, sensed characteristic comprises an acid level (e.g., total acid amount, ascorbic acid amount, etc.), a sugar level (e.g., a degrees Brix, commonly abbreviated as) Bx°, a ratio of sugar to acid amount, a level of soluble solids, a color parameter (e.g., a color intensity, a fraction of surface area that is a particular color, etc.), a visible indicator, a gas amount (e.g., an internal or emitted gas amount such as, e.g., carbon dioxide, ethylene, oxygen, or water vapor), vitamin or other nutrient content, internal color (e.g., for certain tomatoes or mangos), lycopene content (e.g., for tomatoes), prevalence of cotyledons (e.g., for certain beans or onions), wall thickness (e.g., for bell peppers), starch content, or a combination thereof.

In some embodiments, one or more sensors comprise a hyperspectral imaging system, through which information about a sensed or scanned objected is obtained across a much wider portion of the electromagnetic spectrum than is typically obtained by, for example, visible image acquisition systems or infrared-based imaging equipment. Using such a hyperspectral imaging system, in conjunction with machine learning algorithms and training image sets, it may be possible, through analysis of imaging of an object across multiple portions of the electromagnetic spectrum, to determine ripeness, internal or external chemical content, presence of disease, nutrient and water status, quantity of dry or fibrous matter, and various other parameters mentioned herein. Such information may be communicated upstream to growers (e.g., for continual improvement purposes), may be used for produce grading and/or pricing purposes, and/or may be communicated downstream to customers. Moreover, use of hyperspectral imaging may facilitate removable of undesirable material from an industrial processing line (e.g., leaves, stems, shells, protective skins, other organic matter collected during the harvesting process; other debris; contaminants, such as insects, rodents, parts thereof, plastic, paper, cardboard, wood, sticks, dirt, stones, etc.).

To obtain a sensed characteristic, the sensor area 355 may employ a variety of different kinds of sensors. For example, one sensor may be a firmness sensor, or more preferably a non-destructive firmness sensor (e.g., a sensor for measuring a level of firmness of a fruit or vegetable without damaging the fruit or vegetable). Such a firmness sensor could include an acoustical firmness sensor 363, an impact measurement firmness sensor, or a sensor capable of doing both. An example of a commercially available firmness sensor with both acoustical firmness and impact firmness measurement capabilities is the AFS sensor from Aweta G&P B.V. of Pinjacker, Netherlands. See also, e.g., U.S. Pat. No. 6,539,781, which discusses sensing methods and sensors for measuring the firmness of produce such as fruit via tapping of the produce.

Another sensor may be capable of providing an output that is indicative of an internal or external gas concentration of the plant item. See, e.g., U.S. Pat. No. 9,739,737 (Swager et. al), U.S. Pub. No. 2016/0231267 (Swager et al.), and U.S Pub. No. 2019/0285577 (Swager et al.), each of which is incorporated herein by reference in its entirety, for discussion of sensors and methods for measuring the amount of ethylene gas associated with a plant item. One such type of gas sensor could be a photoacoustic sensor (e.g., the Sensor Sense EDT-300 device available from Sensor Sense, B.V. of Nijmegen, Netherlands or the Gasera F10 device available from Gasera Ltd. of Turko, Finland) capable of measuring a gas concentration, preferably one or more of an ethylene gas concentration, an oxygen concentration, or a carbon dioxide concentration. As another example, a gas sensor could be a catalytic sensor 366 capable of measuring a gas concentration, preferably one or more of an ethylene gas concentration, an oxygen concentration, or a carbon dioxide concentration. For example, the ETH1010 instrument (commercially available from Fluid Analytics LLC of Cle Elum, Wash.) is capable of measuring ethylene gas concentration associated with fresh produce via catalytic sensing. Other examples of catalytic sensors may include those utilizing carbon nanotubes and typically one or more metals/catalysts such as copper or palladium catalyst. See, e.g., U.S Pub. No. 2019/0285577 (Swager et al.).

The sensors and sensing technology disclosed in Intl. Pub. No. WO2021/222261 (Person et. al.) for sensing volatiles (e.g., alcohols, aldehydes, unsaturated aldehydes, and/or terpenes) outgassed by plants items (e.g., avocados) that correlate to quality and/or ripeness may also be used. For example, such outgassed volatiles may be sensed in addition to, and/or instead of, ethylene. Specific examples of such outgassed volatiles for sensing may include ethanol, ethyl acetate, ethyl-esters, acetaldehyde, alpha-pinene, limonene, linalool, germacrene D, beta-farnesene, and combinations thereof. In some embodiments, the plant item is an avocado and the outgassed volatile is an alcohol, aldehyde, a terpene, or a combination thereof. In some embodiments, the plant item is a mandarin, and the outgassed volatile is acetaldehyde, alcohol (e.g., ethanol), alpha-pinene, and beta-farnesene, ethyl acetate, ethyl-ester, germacrene D, limonene, linalool, or a combination thereof. In some embodiments, "sniffers" as described in Person et. al. may be employed, which may utilize one or more chromatographic processes to identify and quantitate the concentrations of such outgassed volatiles.

Other examples of sensors that may be employed include metal-oxide gas sensor(s) 369, electrochemical gas sensor(s) 371, conducting/composite polymer gas sensors(s), photoacoustic gas sensor(s), piezoelectric gas sensors(s), infrared gas sensor(s), photoionization detector gas sensor(s), or combinations thereof.

While FIG. 3 shows sensing area 355 occurring downstream of pretreatment area 312, it is contemplated that the sensing step(s) (e.g., accomplished via a plurality of sensing areas 355) may occur in alternate sequencing relative to the other process steps shown in FIG. 3. For example, some or all of the sensing could occur upstream of pretreatment area 312. Moreover, at least some, or all, of the sensing may occur prior to delivery of the plant items to the processing facility. For example, the sensing may occur just prior to harvest of the plant items (e.g., using a hand-held or other mobile device equipped with one or more sensors or a drone or other vehicle equipped with one or more sensors) or simultaneous with, or after, harvest but prior to delivery to the processing facility, with a value or signal communicated such that it can be analyzed by the coating algorithm or method. By way of example, the mobile application from Clarifruit of Rishon LeZion, Israel may be used for such in-field analysis. See also the equipment and methods of U.S. Pat. No. 10,407,748 (Schwartzer et al.) and WO 2021/009753 (Schwartzer et al.), each assigned to Clarifruit.

In some embodiments, the one or more sensing steps is achieved prior to delivery of the plant item (such as, e.g., in the field just prior to, during, or after harvest), wherein one or more sensing steps and/or tracking or communicating of the sensor information may be achieved using supply chain tracking software and/or hardware sold by, for example, Zebra Technologies.

Selective Coating Based on Sensed Parameters

As already discussed herein, coatings can be applied to certain fruits and vegetables, or other live plant items, to help delay or accelerate their rate of ripening and/or for other purposes. However, various fruits and vegetables ripen at different rates, and even produce harvested at the same time can ripen at different rates. Sensors can be utilized to determine the ripeness of a fruit or vegetables as indicated by one or more ripeness parameters such as, e.g., its ethylene concentration, but even with this information, the coating system is incapable of taking maximal advantage of this information without a decision-making functionality such as a suitable algorithm. If the ideal coating parameters are selected by hand for each piece of food product, this process may take too long to be cost-effective and may be more subjective to human error. The advantage to an automated process with a sensor and algorithm, is it allows for application of a coating optimized relative to the state of the actual food product item (or other plant item) to be coated, thereby optimizing the effectiveness of the coating relative to the particular food product (or other plant item). In some embodiments, a machine learning technique is used to select an optimal coating. For example, a machine learning model may map various detected features, desired outcome (e.g., ripe by date or the like), and/or other received information to an optimal coating for achieving the desired outcome. For example, a desired outcome may be a ripe by date or an expiration date, desired storage time before treatment, or desired storage time after treatment. In other examples, the machine learning model may map the various detected features with any associated tags to predict when a plant item will expire with given coatings. This prediction can be printed on a label for the plant item or items and/or associated packaging, if any. The machine learning can be trained to make other predictions or classifications related to a feature of the plant item with different coatings or with no coatings. In alternative embodiments, the machine learning model makes a prediction of one or more features for the plant item. These features can be used by related systems to make downstream decisions (e.g., supply chain decisions). For example, the features of the plant item can be used to determine the priority for shipping plant items, to determine pricing, to determine how long to store plant items before shipping, to determine a type of shipping container (e.g., refrigerated/non-refrigerated) to ship the plant item, to determine a type of shipping or combination of shipping types (e.g., air freight, rail, trucking, and/or boat) to ship the plant items, or any combination thereof. In some of these embodiments, the predictions are automatically implemented using a machine to sort plant items based on the determined priority, other shipping requirements, and/or supply chain management decisions. In other embodiments, the features of the plant item are used to classify a quality of the plant item (e.g., appearance, color, firmness, deformities, ripeness) and the plant item is sorted, removed and/or labeled with the quality of the plant item. The quality of the plant item may further be used for pricing the plant item. In one example, the model is trained to predict a price for each plant item (or group of plant items). In some of these embodiments, the items are automatically labeled with the price using a labeling machine.

In some embodiments, the machine learning model is trained using training data including sensed parameters (described above) from previously analyzed plant items, historical data (e.g., related to the plant items, sales data, etc.), other data about the plant items, and applied treatment information. In some embodiments, the training data (including the raw sensor data) is supplemented by one or more tags. The tags add details (sometimes referred to as tags or labels) to raw data. Example tags include a type of plant item, the type of treatment applied to the plant item, the length of time for the plant item to ripen (or time until optimal ripeness with an applied treatment), the length of time for the plant item to expire, sales data, etc. In some embodiments, the model is trained to detect features in the training data to predict the effect of applying different coatings and ultimately predict an optimal coating. Once trained, the model receives input data (such as the sensed parameters) and predicts an optimal coating based on features detected in the input data. In some examples, the features detected include information about the state, quality, type, and other features of the plant item. Additionally, in some examples, the model receives a desired outcome (e.g., a desired ripe by date or the like) and selects the optimal coating to achieve the desired outcome. In some examples, some of the tags are used to validate a trained model. For example, the training data is split into a training set and a validation set, where the tagged outcomes are hidden in the validation set and compared to the predictions made by the model.

These embodiments are in contrast to existing processes which apply coatings in bulk over the whole harvest, and typically across harvests using a fixed "one-size-fits-all" type of approach for a given food type or food class, and has the potential to result in some fruits and vegetables that still ripen too quickly or others that take too long to ripen. In addition, such "one-size-fits-all" approaches can lead to cost inefficiencies due to over-application of coating materials.

Accordingly, the present description also provides coating treatment systems and methods for selecting or modifying a coating composition, or a dry coating thickness and/or application pattern, based on one or more observed (e.g., measured) characteristics of a plant item to be coated. Such an approach allows for better tailoring of the properties of the coating composition to the type and/or condition (e.g., level of ripeness) of the plant item to be coated. In this manner, a better outcome can be achieved as compared to conventional coating processes that utilize a single "one-size-fits-all" coating composition such as, for example, enhanced shelf-life, enhanced aesthetics, enhanced flavor profiles, and/or delayed or accelerated ripening (for certain plant items) and the like for the coated perishable item. In addition, the amount of applied coating material can be optimized for cost-savings by only applying the amount of coating composition required to achieve the desired result. Moreover, the desired outcomes of a given customer can be better achieved. In some embodiments, historical outcomes are received from customers or plant quality inspectors. The historical outcomes can be used for further training or validating a machine learning model. For example, the customer outcomes can be used to tag future training data for positive or negative training examples. For example, a customer receiving a shipment of plant items may determine the plant items are received with the correct ripeness and provide feedback which is used for further training of the model. Similarly, if an issue is detected by a customer the feedback is used to further train the model as a negative example (e.g., that the selected coating was not correct for the circumstance with the given detected features). Similar tagging can be done automatically (e.g., with image processing) or manually (e.g., by an expert user). Similar feedback can be provided for further training a model for supply chain or shipping decisions. In preferred embodiments, the methods, equipment, and systems are suitable for use in high-throughput agricultural product processing lines such as, for example, used in produce packing houses.

In some embodiments, a plant item may be selectively coated based on previously sensed parameter(s) for that particular plant item—that is, one or more parameters associated with each individual plant item may be sensed, those parameters analyzed, and selective coating be determined and applied to the particular plant item. In other embodiments, the sensing and analysis may occur at a higher, "batch" (or lot) level. That is, parameters from representative samples may be sensed and analyzed, and the selective coating may be determined and applied based on the representative samples (e.g., based on a calculated average or the like for the batch). In such embodiments, sampling and analysis may be repeated periodically, for different batches, and a customized coating may be applied to each batch. Batches and their corresponding representative samples may be based on upstream processing steps (e.g., individual loads of similarly situated plant items, such as from a same harvest, that enter the processing line), or the batches and corresponding representative samples may simply be separated by, for example, periods of time or fixed numbers of plant items.

Although not as efficient, it is also contemplated that one or more steps of the method may also be done in a non-automated step such as, for example, in a manual step. For example, one or more of measurements associated with a perishable item may be conducted by an operator using, for example, a hand-held sensor. Additionally, or alternatively, one or more measurements may be taken in a laboratory, for example, by testing a chemical (e.g., a concentration) or physical (e.g., a firmness or contact angle) property of a perishable item. Such one or more measurements taken via a non-automated technique may then be entered by an operator into a user interface associated with the coating treatment system or otherwise communicated to the coating treatment system.

Drying/Curing

In some embodiments, it may be beneficial or necessary for coatings that are applied to plant items to be dried or cured. In such embodiments, this curing or drying may occur within a drying/curing area 373 of an automated processing line. The drying/curing area 373 may include a drying or storing rack 375 that provides some time for a coating to dry or cure. The drying/curing area 373 may include a heat or energy source 376, such as an infrared or radiative heat source, to facilitate drying/curing of the applied coating composition. Ventilation 378 may also be provided to dry/cure plant items. Other forms of drying maybe provided as well, such as UV curing or e-beam curing (not shown). Other examples of suitable driers include devices (e.g., one or more blowers and/or air knives) configured to apply a moving volume of air or other gasses (e.g., nitrogen gas and/or air and nitrogen mixtures) onto the coated plant item to facilitate removal of solvent (i.e., hardening) from the applied coating composition.

Packaging

After plant items have been dried and cured after any coating process, they may be suitably packaged in a packaging area 380 of an automated line. In the packaging area 380, the plant items may be packaged, for example, in small boxes 382, in units of boxes 385, or on pallets 388 for distribution to end consumers. While not presently preferred, the coated plant items may be packaged prior to complete drying/curing, with some or all of the drying/curing occurring after packaging. Alternatively, or additionally, the plant items may be coated after packaging via, for example, fogging of coating composition into packaging or other enclosure. Such fogging may occur just prior to, during, and/or after locating the plant items in the packaging or other include references. For examples of materials and equipment for accomplishing such fog coating see, for example, WO2020/247667 (Rodriguez et al.).

One or more temporal indications of ripeness may be printed on the packaging or otherwise associated with the packaging or the plant items. For example, a ripeness "window" (i.e., a date range), a use by date, a best by date, a ripe by date, a "ready-to-eat" date range, an optimal ripeness date range, or the like may be associated with the packaging and/or the plant item itself (e.g., via a sticker or other label or indicia applied to the plant item). A ripeness "window" may also include a ripe by color label, where a ripe plant matches a color (e.g., when a color of the plant item substantially matches a color of the label, thereby indicating ripeness) or the label itself changes color to indicate ripeness (e.g., changes from red or orange to green). The particular temporal indication associated with the packaging may vary depending upon customer preferences. In some embodiments, a sticker including one or more such temporal indications of ripeness may alternatively, or additionally, be placed on an exterior surface of the plant items. An algorithm and/or machine learning may be used to determine and/or continuously improve such ripeness temporal indications.

In some embodiments, the coating treatment is applied to the plant items (optionally as a function of customer ripeness preference) so as to meet a targeted ripeness window indication printed or otherwise associated with the packaging in which the plant items are packaged after treatment. As described elsewhere herein, the chemistry, thickness, extent of coating, etc. of the coating can be varied in order to target a ripeness window.

In some embodiments the packaged plant items comprise plants with different ripeness dates. For example, a package could contain plant items that are designed to be consumed at least several days apart. Such differential ripeness in a given package could be achieved through a variety of different means, including, for example, any combination of some plant items being uncoated, some plants items being coated with chemically-different coatings, some plants items being coated with coatings of different thicknesses, including plants items of differing initial ripeness levels (e.g., as determined by sensor data), and the use of ripeness inhibitors and/or accelerants (e.g., in a coating or other treatment). In some embodiments, the package itself may be configured to readily communicate the forecasted differential ripeness to consumers. For example, a clamshell package could be configured to arrange plant items by expected ripeness or expiration date—e.g., in a top-down, left-to-right, and/or front-back format in either descending or ascending ripeness or expiration ordering, with temporal indications optionally included on the package or plant item.

In some embodiments, a plant supply chain is managed by a distributed, or decentralized, ledger based on blockchain. The ledger may also be programmed to trigger transactions automatically. Such transactions may, for example, be activated based upon a targeted ripeness window or other customer preference. Such a digital system can record transactions among multiple parties, as well as supporting access to financing. Inventory, orders, loans, and bills of lading, etc. in the blockchain ledger may be given unique identifiers, i.e. digital tokens. The parties in the blockchain may also have unique identifiers, such as digital signatures, to access the blocks which are added to the blockchain. The blockchain records all stages of the transaction on the digital token, as it passes from one party to the next.

In some embodiments, an enterprise resource planning (ERP) system triggers transactions automatically. Such transactions may, for example, be activated based upon a targeted ripeness window or other customer preference. RFID tags or electronic product codes that adhere to GS1 standards (globally accepted rules for handling supply chain data) may also be used to track plants in the supply chain.

Coating Treatment System

An exemplary coating system 500 is now described with reference to FIG. 5. A coating system (or, similarly, a pretreatment system) may include one or more tanks for holding one or more wash or coating compositions to be applied. More typically, the coating treatment system includes a plurality tanks, such as, for example, tanks 501, 502, 503 and 504. For example, at least one tank may hold a base coating composition (e.g., tank 501) and another tank (e.g., tank 502) may hold a composition for modifying the base coating composition as a function of one or more measured properties. In some embodiments, the base coating composition and one or more modifying compositions are kept separate for, e.g., pot-life stability purposes or the ability to modify to meet differing customer expectations. For example, in some embodiments, the one or more modifying composition includes one or more ingredients (e.g., an enzyme, a catalyst, a metal drier, a produce or plant extract, a reactive ingredient, a digestive aid for the type of produce to be coated, a probiotic, a nutrient or vitamin, a colorant, a gloss additive, etc.) that reacts with the base coating composition and/or facilitates reaction (e.g., crosslinking) of the base coating composition and/or otherwise modifies the base coating composition. Additionally, or alternatively, the coating treatment system may include a plurality of tanks each holding a chemically different coating composition (e.g., tanks 501, 502, 503 and 504) such that the system can select, and optionally further modify, a coating composition to be applied based on one or more measured properties. One or more mixing vessels or devices (e.g., mixing valve 507 or an in-line static mixer or the like) may be present in the system to facilitate the modification or formation of a coating composition, preferably providing sufficient mixing to produce an at least substantially homogenous composition. In some embodiments, the mixing device 507 is computer-controlled (e.g., via a control interface 510). In alternative embodiments, some or all of the mixing may occur on the surface of the plant item itself, for example, via inter-molecular diffusion driven by concentration gradients, surface tensions gradients, and/or thermal gradients. In some embodiments, the base coating composition and one or more modifying compositions can be applied "wet-on-wet" or "wet-on-dry" (e.g., after one or more drying steps) relative to one another in any application order on the plant item to be coated. The two or more different compositions may additionally, or alternatively, be at least partially mixed during application such as, for example, via application of two or more different sprays, mists, or fogs that at least partially combine between release from the applicator and deposition on the plant item.

The one or more tanks are preferably in liquid communication (e.g., via piping) with one or more spray applicators (e.g., applicators 513, 516, and 519) or other coating applicators, with the coating treatment system configured to supply (e.g., under computer control, via control interfaces 514, 517 and 520) the coating product from the one or more tanks to the one or more applicators. Typically, one or more valves, and optionally one or more pumps, are present to facilitate liquid transmission.

In some embodiments, the system includes one or more of: a treatment controller that controls the operation of the respective systems and interfaces with the control system, positioning system electronics configured to receive signals usable to determine the ripeness and/or one or more other parameters of a produce, live plant or other perishable plant product, and a computing device including at least a processing device and a computer readable storage device, the computing device in data communication with the sensor. In preferred embodiments, the computer readable storage device stores data instructions executable by the computing device to cause the computing device to: identify the ripeness and/or one or more other parameters of a produce, live plant, or other perishable plant product, at least some of the products often having different ripeness parameters (e.g., concentrations) and/or other parameters from each other based on various measurable parameters (e.g., concentrations such as an acid level (e.g., total acid, ascorbic acid, etc.), a sugar level (e.g., a degrees Brix, commonly abbreviated as Bx°), a ratio of sugar to acid, a level of soluble solids, a color parameter (e.g., a color intensity, a fraction of surface area that is a particular color, etc.), a visible indicator, a gas amount (e.g., an internal or emitted gas amount such as, e.g., carbon dioxide, ethylene, oxygen, or water vapor)); determine an ideal coating or wash solution composition or both; cause a mix system to prepare the coating or wash solution or both; optionally determine or confirm the current concentration of the coating or wash solution in the applicator; optionally determine or confirm that the applicator contains the correct coating or wash solution concentration for the food products ripeness; and automatically treat the produce, live plant, or other perishable plant product using an optimized coating or wash solution concentration and/or composition.

Exemplary Computer Architecture

Figure 6:
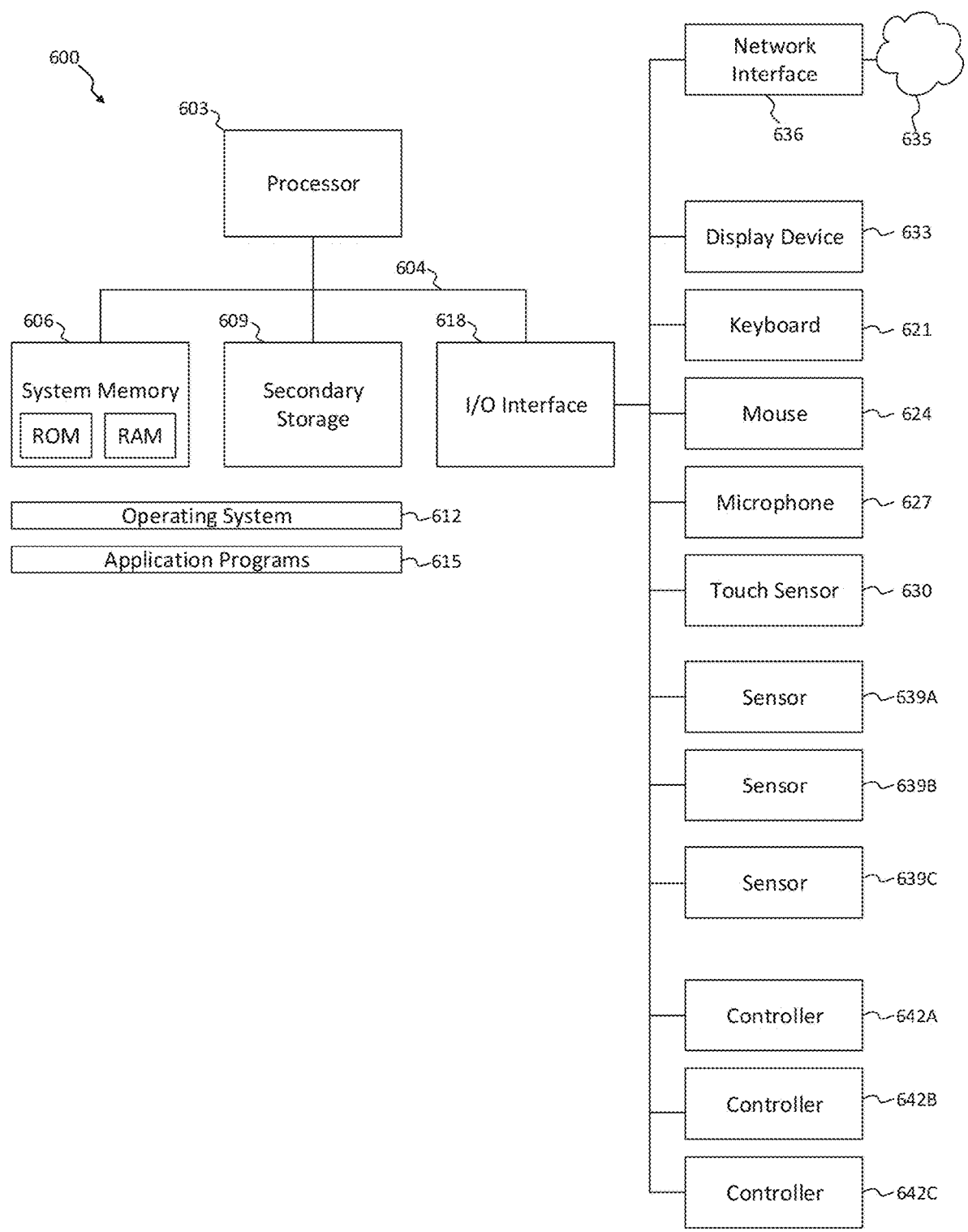
FIG. 6 illustrates an exemplary architecture for a computing system.

FIG. 6 illustrates an exemplary architecture of a computing system 600 that can be used to implement aspects of the present description, including any of the plurality of computing devices described herein. The computing system 600 can be used to execute the operating system, application programs, and software described herein.

Examples of computing devices suitable for the computing device 600 include a server computer, a desktop computer, a laptop computer, a tablet computer, a mobile computing device (such as a smart phone, an iPhone® or iPad® mobile digital device, or other mobile devices), or other devices configured to process digital instructions.

As shown, the computing system 600 includes, in some embodiments, at least one processing device, such as processor 603. A variety of processing devices are available from a variety of manufacturers, for example, Intel or Advanced Micro Devices (AMD).

The processor 603 can be coupled to various other system resources through a system bus 604. The system bus 604 can take many different forms and can include multiple bus structures including a memory bus, or memory controller; a peripheral bus; and a local bus using any of a variety of bus architectures.

The computing system 600 also includes system memory 606. In some embodiments, as shown, the system memory 606 includes read only memory (ROM) and random-access memory (RAM). The computing system 600 can also include a secondary storage device(s) 609 in some embodiments, such as a hard disk drive, for storing digital data. The secondary storage device 609 and their associated computer readable media can provide nonvolatile storage of computer readable instructions (including application programs and program modules), data structures, and other data for the computing system 600.

Although the exemplary environment described herein employs a hard disk drive as a secondary storage device, other types of computer readable storage media are used in other embodiments. Examples of these other types of computer readable storage media include flash memory cards, digital video disks (DVDs), compact disc read only memories, digital versatile disk read only memories, random access memories, or read only memories. Some embodiments include non-transitory media. Additionally, such computer readable storage media can include local storage, cloud-based storage, or a combination of the two.

A number of program modules can be stored in secondary storage device 609 or system memory 606, including an operating system 612 and/or one or more application programs 615. The computing system 600 may utilize any suitable operating system, including, for example, Microsoft Windows™, Google Chrome™, Apple OS, and any other operating system suitable for a computing device.

In many embodiments, users provide inputs to the computing system 600 through one or more input devices that may be integrated through an input/output ("I/O") interface 618. Examples of input devices include a keyboard 621, mouse 624, microphone 627, and touch sensor 630 (such as a touchpad or touch sensitive display). Other embodiments include other input devices.

As shown, the input devices can be connected to the processor 603 through the I/O interface 618 and system bus 604. Input devices can be connected by any number of input/output interfaces, such as a parallel port, serial port, game port, or a universal serial bus. Wireless communication between input devices and the interface is possible as well, and may include, for example, infrared, BLUETOOTH® wireless technology, 802.11a/b/g/n, cellular, or other radio frequency communication systems in some possible embodiments.

In this example embodiment, a display device 633, such as a monitor, liquid crystal display device, projector, or touch sensitive display device, is also included. In addition to the display device 633, the computing system 600 can include various other peripheral devices (not shown), such as speakers, or a printer, or an augmented reality sensor/camera/display system (e.g., to allow an operator to view a portion of an industrial processing line and plant items thereon, with information/analysis overlayed images of the same).

In addition to receiving input from user devices (e.g., keyboard 621, mouse 624, touch sensor 630, etc.), the computing system 600 can also receive input from various sensors, including, for example, sensors 639A, 639B and 639C. For example, with reference to FIG. 3, the sensors 639A-639C could include sensors included in the sensing area 355.

Moreover, in addition to providing output to user devices (e.g., the display device 633), the computing system 600 can also provide outputs to control external equipment, such as, for example elements of an automated processing line. More particularly, controllers 642A, 642B and 642C could control an automated conveyor line, controllers for valves (e.g., the control interfaces 514, 517 or 520 shown in FIG. 5), sprayers (e.g., sprayers 339, 348, 351A or 351B shown in FIG. 3) or other applicators, drying/curing equipment (e.g., drying rack 375, heater 376 or ventilator 378, shown in FIG. 3).

When used in a local area networking environment or a wide area networking environment (such as the Internet), the computing system 600 may be connected to a network 635 through a network interface 636, such as an Ethernet interface. Other possible embodiments use other communication devices. For example, some embodiments of the computing system 600 include a modem or other interface for communicating across the network.

The computing system 600 may include some form of computer readable media (e.g., removable secondary storage 609). Computer readable media can include any available media that can be accessed by the computing system 600. By way of example, computer readable media include computer readable storage media (accessible through a secondary storage device 609, such as a universal serial bus (USB) port or a secure digital (SD) card) and computer readable communication media (e.g., which may be accessible through the network interface 636).

Computer readable storage media can include volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing system 600. Some embodiments include non-transitory media. Additionally, such computer readable storage media can include local storage or cloud-based storage. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing system 600 illustrated in FIG. 6 is also an example of programmable electronics, which may include one or more such computing devices, and when multiple computing devices are included, such computing devices can be coupled together with a suitable data communication network so as to collectively perform the various functions, methods, or operations disclosed herein.

Exemplary Selective Applied Coatings and Methods

Figure 7A:
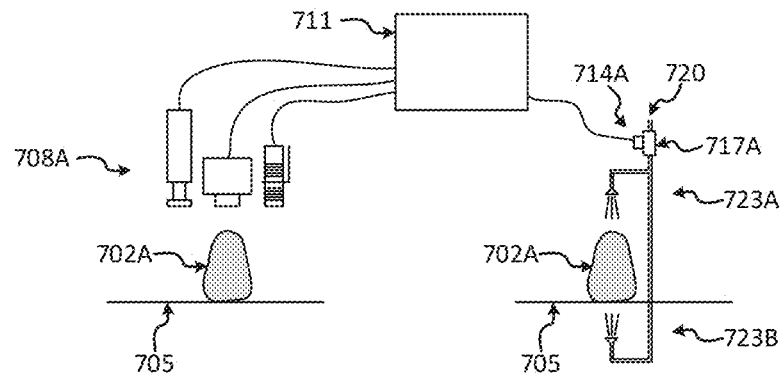
FIGS. 7A, 7B and 7C depict exemplary applications of a selective coating process.

FIG. 7A depicts an exemplary application of the principles described herein. As shown, a plant item (e.g., an avocado 702A) is conveyed, via an automated processing line 705, past one or more sensors (e.g., sensors 708A). Signals from the sensors 708A may be transmitted to a computing device 711.

Using the signals and information from the sensors 708A, the computing device 711 may, through execution of an application program, identify the plant item (e.g., as an avocado), by optically analyzing, for example, its color and shape. Identification of the particular type of plant item may not be necessary in certain embodiments, such as, for example, certain processing lines dedicated to processing a single variety of produce. The computing device 711, using additional sensor data, may further assess the ripeness of the plant item 702A (e.g., by detecting a level of ethylene gas in its proximity, by sensing its firmness, by sensing sound (e.g., ultrasonic waves such as, e.g., employed in a sensor configured for ultrasound imaging to sense internal features) off the plant items, and/or by measuring one or more internal concentrations present in the plant item such as a sugar concentration, a soluble solids concentration, and the like).

Based on the assessed ripeness, the computing device 711, by executing another application, may determine a selective treatment program for the specific plant item 702A. For example, based on the identification of the plant item 702A as an avocado, and based further on an assessment of ripeness, a program to coat the top and bottom of the avocado may be selected, for example, to seal in moisture at points where the skin may typically be weakened. Additionally, or alternatively, the thickness of the applied coating may be adjusted based on the assessment of ripeness.

The computing device 711 may then cause the selective treatment program to be executed, for example, by causing, through a control interface 714A, a control valve 717A to be opened to a coating solution (e.g., from a pipe or conduit 720 coming from a mixing valve (not shown) and an overall coating system (such as that described with reference to FIG. 5) to be dispensed through sprayers 723A and 723B.

Figure 7B:
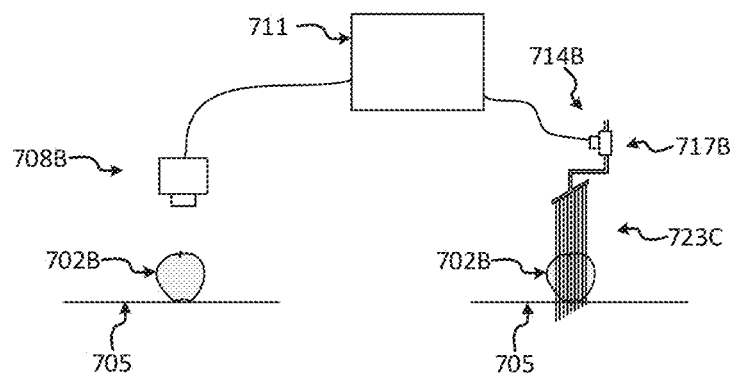

FIG. 7B depicts another exemplary application of the principles described herein. As shown, a plant item (e.g., an apple 702B) is conveyed, via the automated processing line 705, past another sensor 708B.

Using the signal and information from the sensors 708B, the computing device 711 may identify the plant item (e.g., as an apple), by, for example, optically analyzing its color and shape. The computing device 711 may further assess the ripeness of the plant item 702B (e.g., through optical or color analysis).

Based on the assessed ripeness, the computing device 711 may determine a selective treatment program for the specific plant item 702B. For example, based on the identification of the plant item 702B as an apple, and based further on an assessment of ripeness, a program to coat the entire apple may be selected, for example, to seal in moisture and provide a robust waxy sheen. The computing device 711 may then cause the selective treatment program to be executed, for example, by causing, through a control interface 714B, a control valve 717B to be opened to a coating solution to be dispensed through curtain coater 723C.

Figure 7C:
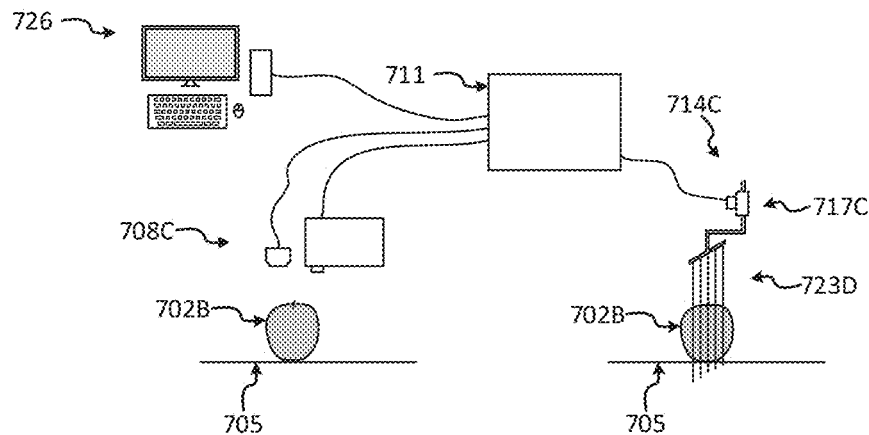

FIG. 7C depicts another exemplary application of the principles described herein. As shown, a plant item (e.g., an apple 702C) is conveyed, via the automated processing line 705, past another set of sensors 708C.

Using the signal and information from the sensors 708C, the computing device 711 may identify the plant item (e.g., as an apple), by optically analyzing its color and shape. The computing device 711 may further assess the ripeness of the plant item 702B (e.g., by sensing $CO_2$, $O_2$ or ethylene in proximity of the apple and by detecting its firmness).

Based on the assessed ripeness, the computing device 711 may determine a selective treatment program for the specific plant item 702C. In some embodiments, additional input may also be used in the selection of the treatment program. For example, user input from another computing interface 726 may be received and factored into the selection. As a more specific example, the computing interface 726 may receive input regarding a destination, projected transport time, and/or desired level of ripeness upon delivery for the plant item 702C.

In such an embodiment, different levels and types of coatings may be applied in order to preserve freshness, slow ripening or accelerate ripening during transport, depending on where the plant item is to be transported after processing. In some instances, it may be desirable to coat the plant item in a manner that will facilitate its ripening upon delivery (e.g., in a case where the plant item may be delivered to a restaurant or a retailer desiring optimally ripe produce for immediate sale). In other instances, it may be desirable to coat the plant item in a manner that delays its ripening (e.g., in a case where the plant item may be in transport and/or at a warehouse for several days or weeks prior to being sold to an end consumer). In still other instances, it may be desirable to omit a coating on plant items (e.g., if ripeness, appearance, flavor or other parameters, in conjunction with shipping information, suggest that the plant items will arrive at their destination in a manner that meets desired specifications, without application of additional coatings).

In the example depicted in FIG. 7C, a computing device 726 is shown as a possible additional input source. A database (e.g., a networked database) could also provide such additional input. The input could also be extracted from other information associated with the plant item 702B or the processing facility (e.g., shipping information to be applied to packaging for the plant item).

Based on the identification of the plant item 702C as an apple and based further on an assessment of ripeness and additional input, a program may be selected to coat the apple 702C with a different composition and at a different thickness than the apple 702B depicted in FIG. 7B. The computing device 711 may then cause the selective treatment program to be executed, for example, by causing, through a control interface 714C, a control valve 717C to be opened to a coating solution to be dispensed through curtain coater 723D.

In the foregoing examples depicted in FIGS. 7A, 7B and 7C, the same processing line 705 can be used for selectively coating different plant items or like plant items in different ways. For example, in some embodiments, each individual plant item may be individually treated. That is, in such embodiments, every plant item passing the sensors 708A, 708B or 708C may cause the computing device 711 to assess characteristics of the plant item (e.g., determine plant item type and ripeness) and select and execute a coating program for that specific plant item. In some embodiments, such a selective analysis and coating process can enable a single processing line 705 to handle a variety of different plant items. In addition, such a selective analysis and coating can allow for better outcomes for different plant items or plant item batches by, for example, more specifically tailoring the applied coating to the condition and/or customer expectations for that particular plant item or batch of plant items.

Figure 5:
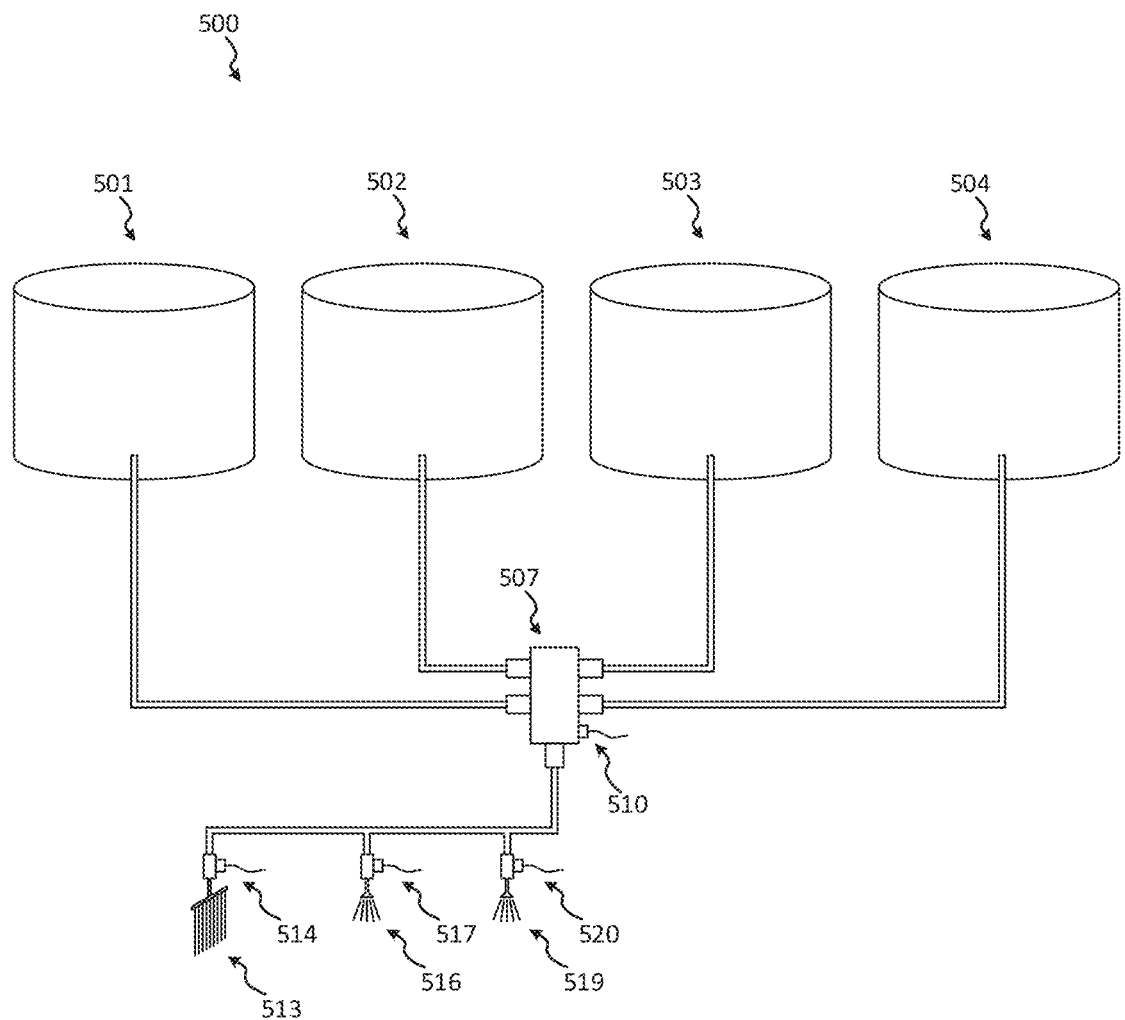
FIG. 5 illustrates an exemplary coating system.

In each of the examples, the computing device 711 may also control a specific mix of coating solution, for example, by selecting specific components from a plurality of components (e.g., compositions stored in the tanks 501, 502, 503 or 504, shown in FIG. 5), or by selecting a base solution (e.g., in tank 501) and modifying that base solution with a modifier (e.g., from tank 502, 503 or 504). In some embodiments, such control may be made by the computing device 711, through (with reference to FIG. 5) the control interface 510 associated with the mixing valve 507.

Figure 8:
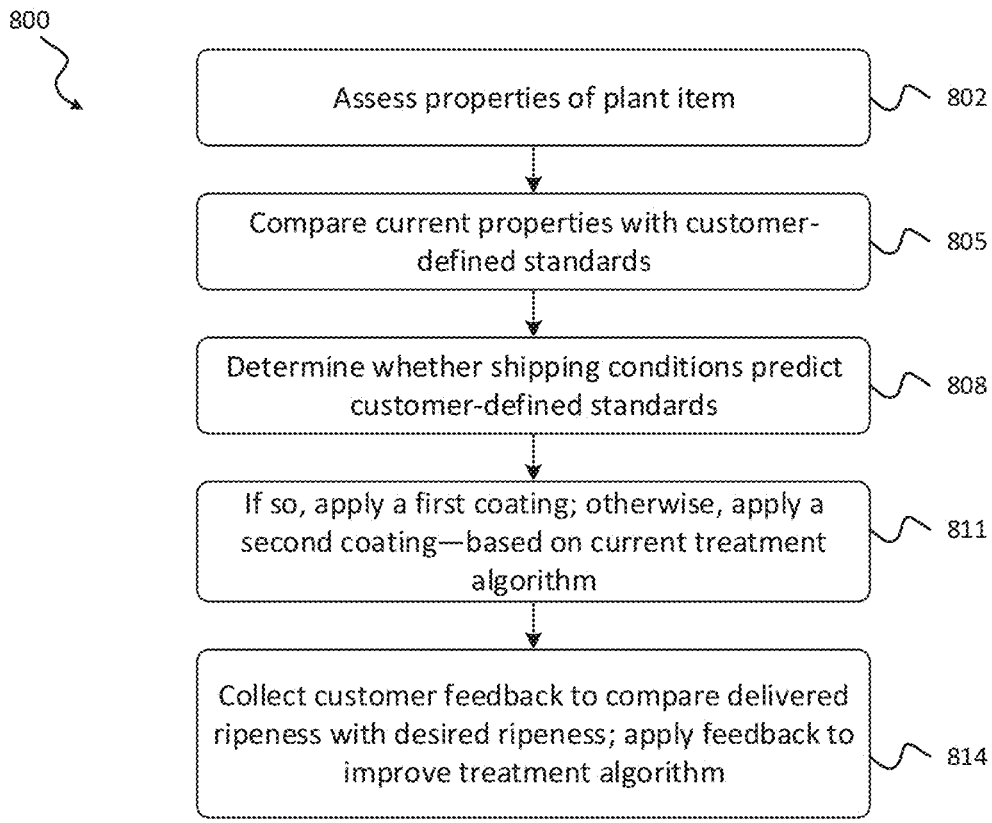
FIG. 8 depicts an exemplary method for selectively applying coatings.

FIG. 8 depicts a method 800 by which additional information (e.g., shipping information and end-customer-desired ripeness parameters) can be factored into a selective coating process. In some embodiments, artificial intelligence or machine learning may be applied to continually improve the selective coating process. The term "customer-defined standard" is used broadly and does not require that the standard actually be defined and/or communicated by a particular customer, although that may be the case in some embodiments. The term also encompasses customer-related metrics identified by method 800 as a function, for example, of the customer-type, anticipated desired state (e.g., appearance, grade, level of ripeness, other quality and/or shelf-life-related information, etc.) of the treated plant item upon arrival at the customer, other known customer-preference-related information, and the like. Artificial intelligence or machine learning can further be applied to make initial selections for the coating process. Examples for using and training machine learning models are described herein.

As shown, the method 800 includes assessing (802) properties of a plant item. For example, a plant item could be assessed by a computing device and signals and information from one or more sensors, as described herein.

The method 800 may further include comparing (805) current properties of the plant item with customer-defined standards. The customer-defined standards may be input through a computing device, like the computing device 726 of FIG. 7C; or the customer-defined standards may be saved in a database or order instructions associated with an automated processing line. In some embodiments, the customer-defined standard may be generated by an algorithm of method 800 based, for example, on customer-related information.

The method 800 may further include determining (808) whether shipping conditions predict customer-defined standards. For example, a computing device (e.g., computing device 711 in FIGS. 7A, 7B and 7C) may—using sensor data to evaluate current characteristics of a plant item (or batch of plant items to which the plant item belongs), and data about the destination and manner of shipment to the destination for the plant item (or batch of plant items)—predict whether the plant item (or batch of plant items) will ripen to a point of meeting customer-defined standards without selective coating (e.g., with no coating or with a standard, unmodified coating). Method 800 may also factor in any anticipated storage steps, if any.

If the method 800 determines (808) that customer-defined standards are likely to be met, (e.g., based on a current treatment algorithm) a first coating may be applied (e.g., a standard, unmodified coating). If, on the other hand, the method 800 determines (808) that the customer-defined standards are not likely to be met, a second (different) coating may be applied (e.g., to extend the life of the plant item during shipping, or to decelerate or accelerate its ripening). Alternatively, the first coating may be applied at a different thickness to try to better meet the customer-defined standard.

In some embodiments, the customer-defined standard may be a ripeness date or time "window" (e.g., a use by date, a best by date, a ripe by date, a "ready-to-eat" date range, an optional ripeness date range, or the like). In such embodiments, the applied coating composition and/or coating thickness may be selected as a function of such ripeness date or time "window" to try to optimally meet customer expectations. Additionally, or alternatively, the method may make a supply chain decision to change a customer and/or customer delivery location to better meet overall customer-defined standards and/or maximize sale price. For example, the method may determine, as a factor of ripeness and/or quality, that it would be more optimal to deliver the treated plant item for more immediate consumption (e.g., by delivering to a geographically closer customer and/or customer location).

In some embodiments, the method 800 further includes collecting customer feedback to compare delivered ripeness (or other customer-identified characteristics) to desired ripeness (or other customer-desired characteristics)—for example, to determine how well the treatment algorithm performed. If delivered parameters did not meet desired parameters, this feedback can be applied (814) to improve the treatment algorithm (e.g., through machine learning).

Figure 9:
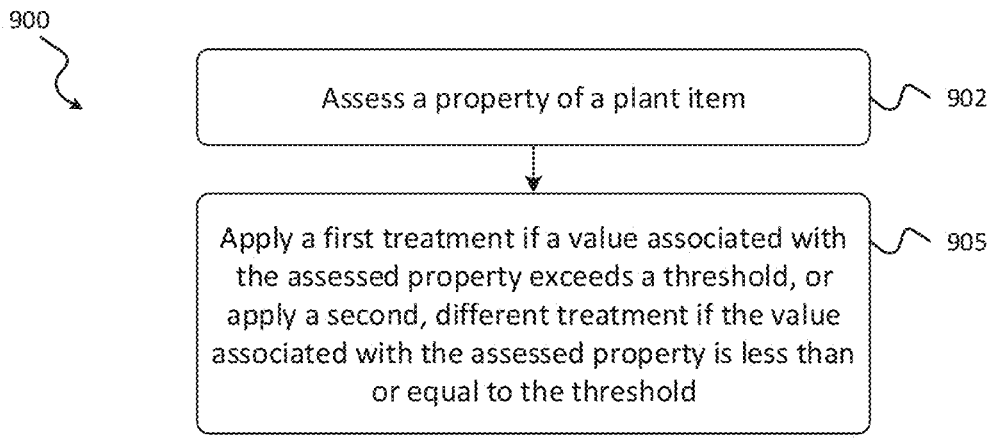
FIG. 9 depicts an exemplary method for selectively applying treatments.

FIG. 9 depicts an exemplary method 900 for selectively applying a treatment. As shown, the method 900 includes assessing (902) a property of a plant item or a batch of plant items. As described herein, a plant item could be assessed by a computing device and signals and information from one or more sensors. In some implementations, the assessed property of the plant item corresponds to a ripeness or quality parameter of the plant item. More particularly, for example, the method 900 could employ hyperspectral imaging to assess a current level of ripeness of an edible fruit or vegetable. Although for convenience purposes the present discussion has generally been in the context of a "plant item", as discussed previously, it should be understood that the sensor information and/or coating decisions may be in relation to a batch of plants items (e.g., a load of similarly-situated plant items harvested on a same day from a same agricultural field) and the sensor information and/or treatments decisions may be based on representative samples and/or averages or other calculated statistical metrics—e.g., as opposed to a one-to-one direct correlation basis between a particular sensed plant item and a particular treated plant item.

The method 900 may further include applying (905) a first treatment if a value associated with the assessed property exceeds a threshold, and applying (905) a second, different treatment if the value associated with the assessed property is less than or equal to the threshold. In some implementations, the threshold could be a percentage of ripeness, relative to full ripeness, of the plant item currently. If the plant item is, for example, more than 50% ripe, a first treatment (e.g., a coating treatment configured to slow the ripening process) may be applied; and if the plant item is less than or equal to 50% ripe, a second treatment (e.g., a wax to merely improve the appearance of the plant item but not slow the ripening process).

The method 900 can include a plurality of such thresholds, each associated with application of a different treatment. For example, in some such embodiments, the treatment applied is prepared based on a second threshold being exceeded (e.g., without exceeding a third threshold, if present in method 900) or third threshold being exceed (e.g., without exceeding a fourth threshold, if present in method 900), and so on. In some embodiments, method 900 may include about 5 or more, about 10 or more, about 20 or more, about 50 or more, or about 100 or more such thresholds, with a treatment decision associated with each threshold. In some embodiments, method 900 may include a near infinite number of such thresholds such as, for example, when after sensing the one or more parameters an algorithm tailors the chemistry of the treatment to be applied based on the one or more sensed parameters. In such embodiments, preparation of the applied treatment in method 900 may be analogous to preparation of architectural paint using point-of-sale mixing equipment, in which a base paint is modified using multiple tint compositions to achieve a finish paint of a very particular desired color. Similarly, in some embodiments, method 900 modifies a base treatment using one or more modifier compositions to achieve the desired final applied treatment composition.

In some embodiments, a model is used to select a treatment for application on at least one plant item. In some embodiments, the model is a trained machine learning model. The trained machine learning model is trained using different training data, such as the data collected by the sensors (e.g., sensed parameters) in previous plant item samples and historical data associated with the plant items. In some embodiments, the training data is further supplemented with tags. The tags can be assigned either automatically, using an algorithm, or manually, with user input. For example, a computer vision algorithm may receive an image of a plant item and automatically tag the item based on detected features. In some embodiments, the model maps the input data to predict an optimal treatment or selects an optimal treatment based on a desired ripeness date. For example, the machine learning model can correlate detected features in the plant item with an optimal treatment or a specific classification with an associated treatment. In some embodiments, the optimal treatment is further based on a desired ripeness date, desired expiration date, or a length of time in storage. In further embodiments, additional machine learning models can be used to detect certain features (e.g., current ripeness or a predicted ripe by date). In some embodiments, the model maps the input data to predict a threshold. For example, before comparing the sensed parameters to a threshold the model first predicts the threshold which provides the optimal border between selecting different treatments. In some embodiments, the model scores the plant item using the sensed parameters, wherein the output score is used to determine which treatment to apply.

Some embodiments include a model library storing a plurality of models which can be selected for use in different circumstances. For example, different models can be used for different types of plants, different predictions, and/or different types of detected features. The models stored in the model library can be updated periodically or continuously. In some embodiments, the local computing system executes instructions which cause the local computing system to retrieve and use the machine learning model. In some embodiments, this local computing system also includes a storage device for storing the library of models. In other embodiments, a centralized storage system (or storage system service) is used and the models are selected (automatically or manually) and retrieved over a network.

In some examples, a local computing system connects with a centralized computing system (e.g., a server or cloud computing system) over a network. The local computing system retrieves sensed parameters and sends the sensed parameters with other input data to the centralized computing system. The centralized computing system receives the input data from the local computing system, and/or from other services (e.g., a historical data store, customer data from a retailer, etc.), executes the machine learning model and provides the output to the local computing system. The training and the application of the machine learning model can be implemented to occur on different locations including a remote computing system, cloud computing system, a cloud computing system operated by a cloud platform and/or machine learning platform provider, or on a local computing system.

In some embodiments, the models are trained using machine learning techniques, such as convolution neural networks (CNNs), random forest modeling, linear regression, logistic regression, naïve bayes, k-nearest neighbors (kNN), support vector machines (SVM), Gaussian mixture models (GMM), artificial neural networks (ANN), etc. Unsupervised or supervised machine learning techniques can be used.

In some embodiments, the machine learning model is trained on a subset of the sensed parameters. For example, the model can be trained on specific data for color, sugar content, and/or non-destructive firmness readings. Each reading can be calibrated on a curve and properties can be identified based on one or all of the readings. The machine learning model is trained to make predictions for the fruit item based on these readings. In alternative embodiments, this is done with predetermined values and does not require training a machine learning model. Some machine learning models may focus on hyperspectral imaging. In one non-limiting example, the data collected from hyperspectral imaging sensors is used to detect features of an avocado. For example, each avocado plant may emit a signature detected using hyperspectral imaging which is indicative of the current state or quality of the avocado plant. Further examples include the use of gas sensors to create an outgas profile for a plant item.

In one non-limiting example, a machine learning model is used to predict an expected ripe by dates for a plurality of plant item. In this example, the expected ripe by dates are used to sort and arrange (and in some embodiments, label) the plant items. For example, a box or clamshell of apples is created by collecting and sorting a set of apples which have consecutive ripe by dates. In other embodiments, the treatment applied to each item is selected to create a set of items with consecutive ripe by dates. In some embodiments, the thickness of the treatment applied to each consecutive item increases to create a set of plant items ordered by an expected ripe by date. Consecutive ripe by dates includes daily, weekly, or an ordered timeline of ripe by dates at different (sometimes inconsistent) frequencies. In one example, a bundle of bananas is processed to have a different treatment (or amount of a treatment) on each banana to create a bundle of bananas comprising an ordered set of ripe by dates. In another example, a collection of avocados is packaged to create an ordered set of avocados having consecutive ripe by dates (e.g., a clamshell package including an avocado to be consumed each day of a week in which the avocados are arranged consecutively based on ripe by dates).

In some embodiments of method 900, a base treatment composition (e.g., a first treatment) may be modified via addition of particular amount(s) of one or more modifying compositions to the base composition to prepare the final applied treatment (e.g., a second treatment, third treatment, fourth treatment, fifth treatment, and the like).

Percentage ripe, relative to full ripeness is one exemplary threshold, but others are possible. For example, a threshold may be based on current color of a plant item's skin relative to its final desired color, a firmness of the plant item, a moisture content, a sugar content, or any of the other parameters described herein. In some embodiments, selection or production of the applied treatment may be determined as a function of a plurality of different threshold types. For example, a particular process might assess both ripeness (e.g., relative to one or a series of ripeness-related thresholds) and aesthetic appearance (e.g., color, relative to one or a series of appearance-related thresholds) and apply a coating composition that addresses both ripeness and desired color based on the assessments.

In some embodiments, the methods, compositions, and/or equipment of the present disclosure may be used to achieve a more standard and/or desired visual appearance across a run of treated produce. For example, based on sensed information, a coating composition including a particular amount of dye and/or colorant may be applied to produce a treated produce lot with less variation in visual appearance across individual product items and/or an overall more desirable appearance on average for individual produce items.

As previously discussed herein, in some embodiments some or all of the sensing may occur in the agricultural field using a drone or other vehicle. It is also contemplated that in addition to sensing, a drone or other vehicle may be used to apply a coating composition to the plant items in the agricultural field prior to harvest, with the applied coating composition being selected or modified based on one or more properties (e.g., any of those disclosed herein) associated with the plant item(s). In this regard, any of the treatment methods or algorithms disclosed herein in the context of an industrial processing line may be utilized by the drone (e.g., aerial drone) or other vehicle. The sensing and coating application may be accomplished by a single drone or other vehicle, or a plurality of drones or other vehicles may accomplish these tasks. For example, a first drone or other vehicle may perform the sensing and a second drone or other vehicle may perform application of the coating composition.

Exemplary Perishable Items for Treatment

Plant items, and particularly live plant items such as fresh fruits and vegetables, are preferred perishable items for processing using the methods and systems of the present disclosure. Examples of plant items that can benefit from treatments methods of the present disclosure include edible plant items and non-edible plant items, and particularly freshly harvested live plant items as well as soon-to-be-harvested live plants items. Examples of such plant items may include flowers and other plant cuttings (e.g., plant cuttings for vegetative propagation), seeds, flower bulbs, nuts, grains, fruits (including, e.g., berries or whole fruit), vegetables, and minimally processed fruit or vegetables (e.g., cut, sliced, peeled, or cored raw fresh fruit or vegetables). The plant items to be coated may be any portions of a plant that may benefit from coating including, for example, a seed, a bulb, a tuber, a corm, a rhizome, a root, a plant cutting, a plant seedling, or a flower (e.g., a cut flower). Examples of fruits that may benefit from treatment methods of the present disclosure include climacteric and non-climacteric fruit, including, for example, an akee, an apple, an apricot, an avocado, a banana, a blackberry, a blueberry, a carambola, a cherry, a coconut, a cranberry, a citrus fruit (e.g., a lemon, a lime, an orange, a mandarin, or a grape fruit), a cucumber (e.g., an English cucumber), a durian, an eggplant, a fig, a grape, a guava, a kiwi, a lychee, a mango, a melon (e.g., a watermelon, a cantaloupe, a honeydew, or a muskmelon), a nectarine, a *papaya*, a passionfruit, a peach, a peapod, a pear, a persimmon, a pineapple, a pepper (e.g., a bell peppers, a habanero pepper, a jalapeno pepper, a poblano pepper, or a serrano pepper), a plum, a pluot, a pomegranate, a raspberry, a strawberry, a squash (e.g., a pumpkin, an acorn squash, a butternut squash, a spaghetti squash, or a zucchini), a tomato, or an uchuva. Examples of vegetables that may benefit from treatment methods of the present disclosure include asparagus, herbs (e.g., fresh herbs, including herb cuttings, such as fresh basil, curry, cilantro, mint, parsley, rosemary, or thyme), beans (e.g., green beans), broccoli, Brussel sprouts, cabbage, carrots, cauliflower, celery, cilantro, corn, garlic, green onions, lettuce, other leafy greens, leeks, onions, mushrooms, parsley, potatoes, artichokes, shallots, spinach, sweet potatoes, or yams.

Additional Exemplary Embodiments

Aspects of the present description may also be described by the embodiments that follow. The features or combination of features disclosed in the following discussion may also be included in any of the other embodiments disclosed elsewhere herein. Solely for purposes of convenience the below embodiments begin with reference to Embodiments "Dx". No inference should be drawn from the embodiment nomenclature beginning with "Dx" as opposed to, e.g., an earlier letter in the alphabet Embodiment D1 is a method of coating a plant surface comprising: assessing (e.g., measuring or identifying) a characteristic of a plant item (or batch of plant items), which can optionally comprise assessing two or more different characteristics of a plant item; adjusting one or both of a wash characteristic or a coating characteristic (e.g., a cross-linking parameter, coating solids, an amount of applied coating per substrate area, a ripening agent, a ripening inhibitor, etc.) of a coating composition as a function of the assessed plant item characteristic (e.g., a carbon dioxide level, an oxygen level, an ethylene level, a sugar level, an acid level, a firmness level, a color indicator or other visual indicator, whether the plant item has been treated with a ripening agent such as ethylene gas, whether the plant item has been treated with a ripening inhibitor such as, e.g., an ethylene receptor antagonist, etc.); and applying a liquid barrier coating composition to at least a portion of a surface of the plant item.

Embodiment A1 is a method for selectively applying a treatment to at least some of a batch of plant items, the method comprising: in an industrial processing line, conveying at least one plant item in the batch of plant items to a sensing region having one or more sensors; with the one or more sensors and a computing device, assessing one or more properties of the plant item associated with ripeness and/or another attribute; conveying at least one of the batch of plant items to a treatment region; in the treatment region, applying a first treatment to at least one of the batch of plant items if the assessed one or more property exceeds a first threshold, or applying a second treatment to at least one of the batch of plant items if the assessed one or more properties is equal to or less than the first threshold, the first treatment being different than the second treatment.

Embodiment A2 is a method for selectively applying a treatment to at least some of a batch of plant items, the method comprising: in an industrial processing line, conveying at least one plant in the batch of plant items to a sensing region having one or more sensors; with the one or more sensors and a computing device, assessing one or more properties of the plant item associated with ripeness and/or another attribute; determining, based on (i) the assessed one or more properties, (ii) a customer-defined standard for a customer, and optionally (iii) shipping parameters associated with the customer, whether the plant item is likely to meet the customer-defined standard upon arrival at the customer; and based on a determination that the plant item is likely to meet the customer-defined standard upon arrival at the customer, applying a first treatment to the plant item or based on a determination that the plant item is not likely to meet the customer-defined standard upon arrival at the customer, applying a second treatment that is different than the first treatment.

Embodiment A3 is a method for selectively applying a treatment to at least some of a batch of plant items, the method comprising: with one or more sensors and a computing device, assessing one or more properties of at least one plant item in the batch of plant items, the assessed one or more properties being associated with ripeness and/or another attribute; in the treatment region of an industrial processing line, applying a first treatment to at least one of the batch of plant items if the assessed one or more properties exceeds a first threshold, or applying a second treatment to the batch of plant items if the assessed one or more properties is equal to or less than the first threshold, the first treatment being different than the second treatment.

Embodiment A4 is the method of any of embodiments A1 to A3, wherein the treatment comprises a liquid coating treatment or a liquid wash treatment.

Embodiment A5 is the method of any of embodiments A1 to A4, wherein plant items comprises an edible plant item.

Embodiment A6 is the method of embodiment A5, wherein the plant items comprises whole fruit or whole vegetables.

Embodiment A7 is the method of embodiment A5 or A6, wherein the plant item comprises a fruit selected from an akee, an apple, an apricot, an avocado, a banana, a blackberry, a blueberry, a carambola, a cherry, a coconut, a cranberry, a citrus fruit (e.g., a lemon, a lime, an orange, a mandarin, or a grape fruit), a cucumber (e.g., an English cucumber), a durian, an eggplant, a fig, a grape, a guava, a kiwi, a lychee, a mango, a melon (e.g., a watermelon, a cantaloupe, a honeydew, or a muskmelon), a nectarine, a *papaya*, a passionfruit, a peach, a peapod, a pear, a persimmon, a pineapple, a pepper (e.g., a bell pepper, a habanero pepper, a jalapeño pepper, a poblano pepper, or a serrano pepper), a plum, a pluot, a pomegranate, a raspberry, a strawberry, a squash (e.g., a pumpkin, an acorn squash, a butternut squash, a spaghetti squash, a yellow squash, or a zucchini), a tomato, or an uchuva.

Embodiment A8 is the method of embodiment A5 or A6, wherein the plant items comprise vegetables selected from asparagus, basil, beans (e.g., green beans), broccoli, Brussels sprouts, cabbage, carrots, cauliflower, celery, cilantro, corn, garlic, green onions, lettuce or other leafy greens, leeks, onions, mushrooms, parsley, potatoes, shallots, spinach, sweet potatoes, artichokes, or yams.

Embodiment A9 is the method of any of the embodiments A1 to A8, wherein applying the first treatment or second treatment comprises applying a coating composition to at least a portion of a removable skin or an inedible skin.

Embodiment A10 is the embodiment of any of embodiments 3 to 9, wherein assessing one or more properties of the at least one plant item comprises assessing from a drone equipped with the one or more sensors.

Embodiment A11 is the method of any of embodiments A3 to A10, wherein assessing the one or more properties of the at least one plant item comprises assessing within 6 hours, 12 hours, 24 hours or 48 hours of applying the first treatment or second treatment.

Embodiment A12 is the method of any of embodiments A1 to A11, wherein the one or more properties comprise an acid level, a sugar level, a ratio of sugar to acid, a level of soluble solids, a color parameter, a visible indicator, a gloss level, a gas identity, a gas amount, a vitamin content, an internal color, lycopene content, a prevalence of cotyledons, a wall thickness, a starch content, a microbial parameter, a firmness amount, or a combination thereof.

Embodiment A13 is the method of any of embodiments A1 to A12, wherein the first treatment and second treatment are each stored in separate containers that are in liquid communication with one or more dispensers in the treatment region of the industrial processing line.

Embodiment A14 is the method of any of embodiments A1 to A13, wherein the treatment is prepared, based on the one or more properties, by combining a first part and a second part, the first part and the second part comprising two or more chemically-different parts.

Embodiment A15 is the method of embodiment A14, wherein the two or more chemically-different parts are combined in a particular ratio after assessing the one or more properties and before applying the first treatment or the second treatment.

Embodiment A16 is the method of embodiment A14 or A15, wherein the first part comprises one or both of: (i) an ingredient that is reactive with an ingredient of the second part or (ii) an ingredient that facilitates the reaction of an ingredient in the second part.

Embodiment A17 is the method of any of embodiments A14 to A16, wherein an ingredient in the first or second part comprises a crosslinking agent that is reactive with an ingredient having one or more active hydrogen groups present in the other of the other of the first or second parts.

Embodiment A18 is the method of any of embodiments A14 to A17, wherein one of the first part or second part comprises a base composition comprising a base coating composition or base wash composition that is modified by combining with one or more, two or more, or three or more chemically-different other parts.

Embodiment A19 is the method of embodiment A18, wherein the base composition is a base coating composition that is modified, based on the one or more properties, to change one or more coating parameters selected from: a crosslinking parameter, total coating solids, glossiness, hydrophobicity, hydrophilicity, surface tension, gas permeability (e.g., permeability to carbon dioxide, oxygen, ethylene, and/or water vapor), dry film weight and/or coating thickness, crystallinity, pH, an antimicrobial property (e.g., presence and/or concentration of one or more anti-microbial agents), or a color parameter.

Embodiment A20 is the method of any of embodiments A1 to A19, wherein the first treatment comprises a first liquid coating composition, the second treatment comprises a second liquid coating composition, and the method further comprises hardening the first liquid coating composition or second liquid coating composition to form a hardened coating on at least a portion of each plant item in the batch of plant items.

Embodiment A21 is the method of any of embodiments A1 to A20, wherein the first treatment or second treatment includes one or more additives selected from a plasticizer, a wax, a lipid, an amino acid, a dispersing agent, an antimicrobial agent, an anti-browning or -yellowing agent (e.g., ascorbic acid or citric acid), a probiotic, a vitamin or other nutrient, an enzyme, a plant hormone or regulator, a colorant, a flavorant, an aromatic, an oxygen-scavenging agent, a compatibilizer, a leveling agent, a wetting agent, an adhesion promoter, a rheology modifier, an antifoaming agent, or a ripening inhibitor (e.g., an ethylene inhibitor and/or scavenger).

Embodiment A22 is the method of any of embodiments A1 to A21, wherein the first and second treatments are coating compositions, and wherein at least one of the first treatment or second treatment includes a monoester of a fatty acid (e.g., a mono-glyceride such as, for example, 2,3-dihydroxypropyl palmitate, 1,3-dihydroxypropan-2-yl palmitate, 2,3-dihydroxypropyl stearate (e.g., CAS Registry No. 123-94-4), 1,3-dihydroxpropan-2-yl stearate, mono-laurin and mixtures thereof.)

Embodiment A23 is the method of any of embodiments A1 to A22, wherein the first and second treatments are coating compositions, and wherein at least one of the first or second treatments includes a polypeptide (e.g., silk fibroin), a polysaccharide (e.g., pectin), or a combination thereof.

Embodiment A24 is the method of claim of any of embodiments A1 to A23, wherein the one or more sensors are selected from a firmness sensor (e.g., an acoustical firmness sensor or, an impact measurement firmness sensor), an optical sensor, a spectrophotometer, a photo-acoustic sensor, a catalytic sensor, an infrared sensor, a gloss meter, an metal-oxide gas sensor, an electrochemical gas sensor, a conducting/composite polymer gas sensors, a photo-acoustic gas sensor, a piezoelectric gas sensors, a photoionization detector gas sensor.

Embodiment A25 is the method of any of embodiments A1 to A24, wherein the one or more sensors include a sensor configured for hyperspectral imaging.

Embodiment A26 is the method of any of embodiments A1 to A25, wherein the threshold comprises a prediction of ripeness and/or another attribute at a time of delivery that is based on (i) a customer-defined standard for a customer and/or (ii) shipping parameters associated with the customer.

Embodiment A27 is the method of embodiment A26, wherein applying the first treatment comprising a first coating composition or applying the second treatment comprising a second coating comprises applying based on a current treatment algorithm, the method further comprising collecting feedback after arrival of the batch of plant items at the customer, the feedback regarding whether the batch of plant items, as delivered, met the customer-defined standard for the customer.

Embodiment A28 is the method of embodiment A27, further comprising modifying the current treatment algorithm based on the collected feedback.

Embodiment A29 is the method of any of embodiments A1 to A28, wherein the method includes a plurality of thresholds for determining the treatment to be applied, wherein each threshold is associated with application of a different treatment, and wherein the method includes more than two potential treatments for application.

Embodiment A30 is the method of any of embodiments A1 to A31, wherein the method includes accessing two or more different properties associated with ripeness and/or another attribute of the at least one plant item.

Embodiment A31 is the method of any of embodiments A1 to A30, wherein applying the first or second treatment comprises spraying, dipping, brushing or curtain coating the at least one plant item.

Embodiment D1 is a method of embodiment D1, wherein the coating characteristic is adjusted.

Embodiment D2 is a method of embodiment D1 or D1a, further comprising hardening (e.g., drying) the liquid barrier coating composition to form a coating (preferably wherein all or substantially all of any liquid carrier has been removed).

Embodiment D3 is a method of embodiment D2, wherein the step, or steps, of hardening the coating composition comprises one or more of: storing, drying, heating (i.e., above ambient temperature), UV curing, or e-beam curing.

Embodiment D4 is a method of any of embodiments D1 to D3, wherein assessing the plant item characteristic comprises measuring or identifying a characteristic associated with a sample of plant items, preferably a representative sample of plant items, from a population of harvested plant items, and coating the population of harvested plant items with the liquid barrier coating composition selected or modified based on the one or more characteristics.

Embodiment D5 is a method of any of embodiments D1 to D4, wherein the assessed plant item characteristic is an indicator of ripeness level.

Embodiment D6 is a method of embodiment D4 or D5, wherein the assessed plant item characteristic comprises an acid level (e.g., total acid, ascorbic acid, etc.), a sugar level (e.g., a degrees Brix, commonly abbreviated as Bx°), a ratio of sugar to acid, a level of soluble solids, a color parameter (e.g., a color intensity, a fraction of surface area that is a particular color, etc.), a visible indicator, a gas amount (e.g., an internal or emitted gas amount such as, e.g., carbon dioxide, ethylene, oxygen, or water vapor), vitamin content, internal color (e.g., for certain tomatoes or mangos), lycopene content (e.g., for tomatoes), prevalence of cotyledons (e.g., for certain beans or onions), wall thickness (e.g., for bell peppers), starch content, any other parameters disclosed herein, or a combination thereof.

Embodiment D7 is a method of any of embodiments D1 to D6, wherein adjusting the coating characteristic comprises selecting a particular coating composition out of a plurality of chemically different coating composition options (e.g., a coating composition inventory).

Embodiment D8 is a method of any of embodiments D1 to D6, wherein adjusting the coating characteristic comprises modifying a base coating composition.

Embodiment D9 is a method of any of embodiments D1 to D8, wherein the coating composition is selected or modified to include an additive.

Embodiment D10 is a method of any of embodiments D9, wherein the coating composition is selected or modified to include a concentration of a particular additive (e.g., any of those disclose herein such as, for example, a cross-linking related agent (e.g., a polyvalent metal crosslinking agent, an ethylenically unsaturated component, and/or an active hydrogen component preferably reactive with the polyvalent metal crosslinking reaction), an adhesion promoter, a wetting agent, etc.).

Embodiment D11 is a method of any of embodiments D1 to D6 or D8 to 10, wherein adjusting a coating characteristic comprises combining two or more chemically different parts.

Embodiment D12 is a method of embodiment D11, wherein the two or more chemically different parts are combined in a particular ratio.

Embodiment D13 is a method of embodiment D11 or D12, wherein one of the parts is a base coating composition and the other of the one or more parts is a modifier component (e.g., to add an additive to the base coating composition that is not present in the base coating composition, to increase a concentration of an ingredient present in the base coating composition, or to dilute (i.e., decrease) a concentration of an ingredient present in the base coating composition).

Embodiment D14 is a method of any of embodiments D1 to D13, wherein the average chain length of carbon atoms in a fatty acid portion (e.g., in a free fatty acid or salt thereof and/or fatty acid chain of a mono-, di-, or tri-glyceride or other esterified fatty acid compound) of the coating composition is increased or decreased.

Embodiment D15 is a method of embodiment D10 or D14, wherein a first coating part includes a first fatty acid portion and a second coating part includes a second fatty acid portion, and wherein a carbon chain length (including the carbonyl carbon) of the first fatty acid portion differs from a carbon chain length (including the carbonyl carbon) of the second fatty acid portion by at least 1, at least 2, at least 3, at least 4, at least 5, at least 6, at least 7, at least 8, or 9 or more carbon atoms.

Embodiment D16 is a method of embodiment D14 or D15, wherein the average chain length of carbon atoms in the coating composition is adjusted to a desired level by blending the at least first and second coating parts in a particular ratio.

Embodiment D17 is a method of any of embodiments D1 to D16, wherein the coating composition is selected or modified to provide a coating (preferably a continuous or substantially continuous hardened coating) on the harvested plant items that has an increased permeability (e.g., 1% or more, 2% or more, 3% or more, 4% or more, 5% or more, 7% or more, 10% or more, 12% or more, 15% or more, 20% or more, 25% or more, 30% or more, 35% or more, 40% or more, 45% or more, 50% or more, 60% or more, 70% or more, 80% or more, 90% or more, 100% or more, 150% or more, 200% or more, 250% or more, or 300% or more) to one or more, two or more, three or more, or all of: water vapor, oxygen, carbon dioxide, or ethylene gas relative to a reference coating (e.g., a coating formed from an appropriate base coating composition).

Embodiment D18 is a method of any of embodiments D1 to D17, wherein the coating composition is selected or modified to provide a coating (preferably a continuous or substantially continuous hardened coating) on the harvested plant items that has a decreased permeability (e.g., 1% or less, 2% or less, 3% or less, 4% or less, 5% or less, 7% or less, 10% or less, 12% or less, 15% or less, 20% or less, 25% or less, 30% or less, 35% or less, 40% or less, 45% or less, 50% or less, 60% or less, 70% or less, 80% or less, 90% or less, or 95% or less) to one or more, two or more, three or more, or all of water vapor, oxygen, carbon dioxide, or ethylene gas relative to a reference coating (e.g., a coating formed form an appropriate base coating composition).

Embodiment D19 is a method of any of embodiments D1 to D18, wherein the coating composition is selected or modified to provide a greater amount of crosslinking.

While not intending to be bound by theory, a greater amount of crosslinking is believed to decrease one or more permeabilities (e.g., water vapor, oxygen, carbon dioxide, or ethylene gas permeabilities) or solubilities (e.g., water solubility) of a hardened coating formed from the coating composition in most instances.

Embodiment D20 is a method of embodiment D19, wherein the coating composition is selected or modified to provide an increased amount of one or more crosslinking-related agents such as, for example, one or more of an ethylenically unsaturated component (preferably any of those disclosed herein, such as, e.g., an unsaturated fatty acid or salt thereof or unsaturated fatty acid ester such as, e.g., an unsaturated mono-glyceride), an active hydrogen compound (preferably any of those disclosed herein, e.g., such as a carboxyl-functional active hydrogen compound, typically one or more of a lipid, polysaccharide, and/or polypeptide), a metal compound (preferably any of the polyvalent metal crosslinking compounds disclosed herein, such as an iron, calcium, manganese, or zinc compound, or plant edible extract containing one or more such compounds), a crosslinking enzyme (e.g., transglutaminase), or a combination thereof.

Embodiment D21 is a method of embodiment D19 or D20, wherein the amount of crosslinking is increased by an amount that causes the water-solubility of a coating formed from the coating composition (preferably a continuous or substantially continuous hardened coating) to decrease by at least 0.1%, at least 0.5%, at least 1%, at least 2%, at least 3%, at least 4%, at least 5%, at least 6%, at least 7%, at least 8%, at least 9%, at least 10%, at least 15%, at least 20%, at least 25%, at least 30%, at least 40%, at least 50%, at least 60%, at least 70%, or at least 80%.

Embodiment D22 is a method of any of embodiments D19 to D21, wherein a hardened coating formed from the coating composition exhibits an increased gel fraction (e.g., at least 0.1% greater, at least 0.5% greater, at least 1% greater, at least 2% greater, at least 3% greater, at least 4% greater, at least 5% greater, at least 6% greater, at least 7% greater, at least 8% greater, at least 9% greater, at least 10% greater, at least 11% greater, at least 12% greater, at least 13% greater, at least 14% greater, at least 15% greater, at least 16% greater, at least 17% greater, at least 18% greater, at least 19% greater, or at least 20% greater) relative to an otherwise identical coating formed under identical conditions from a coating composition omitting the polyvalent metal crosslinker compound.

Embodiment D22 is a method of any of embodiments D1 to D18, wherein the coating composition is selected or modified to provide a reduced amount of crosslinking.

Embodiment D24 is a method of embodiment D23, wherein the coating composition is selected or modified to include a decreased amount of one or more crosslinking-related agents such as, for example, one or more of an ethylenically unsaturated component (preferably any of those disclosed herein such as, e.g., an unsaturated fatty acid or salt thereof or an unsaturated fatty acid ester such as, e.g., an unsaturated mono-glyceride or other unsaturated fatty-acid monoester), an active hydrogen compound (preferably any of those disclosed herein, e.g., such as a carboxyl-functional active hydrogen compound, typically one or more of a lipid, polysaccharide, and/or polypeptide), a metal compound (preferably any of the polyvalent metal crosslinking compounds disclosed herein, e.g., such as an iron, calcium, manganese, or zinc compound, or plant edible extract containing one or more such compounds), a crosslinking enzyme (e.g., transglutaminase), or a combination thereof.

Embodiment D25 is a method of any of embodiments D1 to D24, wherein the plant item comprises a harvested plant item.

Embodiment D26 is a method of any of embodiments D1 to D25, wherein the plant item comprises a seed, a bulb, a tuber, a corm, a rhizome, a root, a plant cutting, a plant seedling, or a flower (e.g., a cut flower).

Embodiment D27 is a method of any of embodiments D1 to D26, wherein the plant item comprises an edible plant item.

Embodiment D28 is a method of any of embodiments D1 to D27, wherein the edible plant item comprises a fruit (typically a freshly harvested fruit), a vegetable (typically a freshly harvested vegetable), a grain, or a seed.

Embodiment D29 is a method of embodiment D28, wherein the edible plant item comprises a fruit such as, e.g., an akee, an apple, an apricot, an avocado, a banana, a blackberry, a blueberry, a carambola, a cherry, a coconut, a cranberry, a citrus fruit (e.g., a lemon, a lime, an orange, a mandarin, or a grape fruit), a cucumber (e.g., an English cucumber), a durian, an eggplant, a fig, a grape, a guava, a kiwi, a lychee, a mango, a melon (e.g., a watermelon, a cantaloupe, a honeydew, or a muskmelon), a nectarine, a *papaya*, a passionfruit, a peach, a peapod, a pear, a persimmon, a pineapple, a pepper (e.g., a bell peppers, a habanero pepper, a jalapeño pepper, a poblano pepper, or a serrano pepper), a plum, a pluot, a pomegranate, a raspberry, a strawberry, a squash (e.g., a pumpkin, an acorn squash, a butternut squash, a spaghetti squash, or a zucchini), a tomato, or an uchuva.

Embodiment D30 is a method of embodiment D29, wherein the fruit comprises a whole fruit.

Embodiment D31 is a method of embodiment D29 or D30, wherein the fruit comprises a climacteric fruit.

Embodiment D32 is a method of embodiment D29 or D30, wherein the fruit comprises a non-climacteric fruit.

Embodiment D33 is a method of any of embodiments D1 to D28, wherein the edible harvested plant item comprises a vegetable such as, e.g., asparagus, basil, beans (e.g., green beans), broccoli, Brussels sprouts, cabbage, carrots, cauliflower, celery, cilantro, corn, garlic, green onions, lettuce, other leafy greens, leeks, onions, mushrooms, parsley, potatoes, shallots, spinach, sweet potatoes, or yams.

Embodiment D34 is a method of any of embodiments D27 to D33, wherein the coating composition is applied to at least a portion of a removable skin (e.g., removable peel).

Embodiment D35 is a method of any of embodiments D27 to D33, wherein the coating composition is applied to at least a portion of an inedible skin (e.g., an avocado peel, a banana peel, etc.).

Embodiment D36 is a method of any of embodiments D1 to D35, wherein the plant item to be coated is treated with UV light prior to coating.

Embodiment D37 is a method of any of embodiments D1 to D36, wherein applying the coating composition comprises spraying (which can comprise misting or fogging) the coating composition onto the plant item (preferably a freshly harvested plant item).

Embodiment D38 is a method of embodiment D37, wherein the coating composition is sprayed onto the plant item using any of the methods or equipment disclosed in WO2015/017450 (Rogers et al.), which is incorporated herein by reference in its entirety.

Embodiment D39 is a method of any of embodiments D1 to D36, wherein applying the coating composition onto the plant item comprises dipping the plant item into the liquid barrier coating composition (e.g., dipping once, twice, or three or more times, with optional hardening between one or more applications of the coating composition).

Embodiment D40 is a method of any of embodiments D1 to D36, wherein applying the liquid barrier coating composition to the plant item comprises coating the plant item using a curtain (or "waterfall") coating process. Typically, such curtain coating processes entail transporting the plant item through a flowing curtain of the liquid barrier coating composition to coat the plant item.

Embodiment D41 is a method of any of embodiments D1 to D36, wherein applying the liquid barrier coating composition to the plant item comprises brushing or rolling the coating composition onto the plant item.

Embodiment D42 is a method of any of embodiments D1 to D41, wherein a roller-containing conveyor and/or dispensing and/or inspection system is used (see, e.g., the systems of WO2019/028043 (Holland et al.) or WO2020023319 (Hegel at. al.), each of which is incorporated herein by reference in its entirety).

Embodiment D43A is a method of any of embodiments D1 to D42, wherein prior to coating, a gloss coating characteristic of the liquid barrier coating composition is modified or a liquid barrier coating composition having a particular gloss coating characteristic is selected, preferably such that a hardened coating formed from the coating composition on the plant items exhibits a gloss that is substantially similar to that exhibited by the plant item prior to coating (e.g., a gloss within 30%, within 20%, within 15%, within 10%, or within 5% of a gloss of a surface of the plant item prior to coating), wherein the gloss is measured at one or more angles such as, for example, 60°. An example of a piece of equipment for assessing the glossiness (e.g., at 60°) of the surface of plant items (e.g., fruit and vegetables) is the Elcometer 400 Nova-Curve glossmeter for curved surfaces (commercially available from Elcometer of Nova, Mich.).

Embodiment D43B is a method of any of embodiments D1 to D42, wherein after coating, a gloss of the hardened coating on the plant item is changed (e.g., to be within 30%, within 20%, within 15%, within 10%, or within 5% of a gloss of a surface of the plant item prior to coating), wherein the gloss is measured at one or more angles such as, for example, 60°. An example of a piece of equipment for assessing the glossiness (e.g., at 60°) of the surface of plant items (e.g., fruit and vegetables) is the Elcometer 400 Nova-Curve glossmeter for curved surfaces (commercially available from Elcometer of Nova, Mich.).

Embodiment D44 is a method of embodiment D43B, wherein the gloss of the coating is changed via brushing the coating, typically after hardening (e.g., to be within 30%, within 20%, within 15%, within 10%, or within 5% of the glossiness of surface plant item prior to coating), see, e.g., the equipment and methods of U.S. Pat. No. 9,648,890 (Nussinovitch et al.), which is incorporated herein by reference in its entirety.

Embodiment D45 is a method of any of embodiment D1 to D44, wherein the coating composition is selected or modified to provide a coating composition having a desired pH level (e.g., as a function of the type of the plant item to be coated and/or the condition of the plant item to be coated).

Embodiment D46 is a method of any of embodiments D1 to D45, wherein the liquid barrier coating composition applied to the plant item, or a base coating composition used to form the liquid barrier coating composition, is any of the coating compositions disclosed herein.

Embodiment D47 is a method of any of embodiment D1 to D46, wherein a sensor (or a plurality of sensors: e.g., 2 or more, 3 or more, 4 or more, 5 or more, and so on, of the same or different sensor types) is used to assess a plant characteristic (or a plurality of plant characteristics) of the plant item, which is preferably one or more ripeness parameters, one or more quality parameters, or a combination thereof.

Embodiment D48 is a method of embodiment D47, wherein the sensor is a firmness sensor, more preferably a non-destructive firmness sensor (e.g., a sensor for measuring a level of firmness of a fruit or vegetable without damaging the fruit or vegetable).

Embodiment D49 is a method of embodiment D48, wherein the hardness sensor comprises an acoustical firmness sensor, an impact measurement firmness sensor, or a sensor capable of doing both. An example of a commercially available firmness sensor with both acoustical firmness and impact firmness measurement capabilities is the AFS sensor from Aweta G&P B.V. of Pinjacker, Netherlands. See also, e.g., U.S. Pat. No. 6,539,781, which discusses sensing methods and sensors for measuring the firmness of produce such as fruit via tapping of the produce.

Embodiment D50 is a method of any of D47 to D49, wherein the sensor is capable of providing an output indicative of an internal or external gas concentration of the plant item. See, e.g., U.S. Pat. No. 9,739,737 (Swager et. al) and U.S. Pub. No. 2016/0231267 (Swager et al.), each of which is incorporated herein by reference in its entirety, for discussion of sensors and methods for measuring the amount of ethylene gas associated with a plant item.

Embodiment D51 is a method of any of embodiments D47 to D50, wherein the sensor is capable of providing an output indicative of a color parameter and/or other visible characteristic of the plant item (e.g., a color parameter indicative of a level of fruit or vegetable ripeness such as, for example, a hue angle).

Embodiment D5 is a method of any of embodiments D47 to D51, wherein the sensor comprises an optical sensor (which may optionally perform hyperspectral imaging).

Embodiment D53 is. a method of embodiment 52, wherein the optical sensor comprises an image acquisition device (e.g., a still and/or video camera).

Embodiment D54 is a method of any of embodiments D47 to D53, wherein the sensor comprises a spectrophotometer.

Embodiment D55 is a method of any of embodiments D47 to D54, wherein the sensor comprises a photo-acoustic sensor (e.g., the Sensor Sense EDT-300 device or the Gasera F10 device) capable of measuring a gas concentration, preferably one or more of an ethylene gas concentration, an oxygen concentration, or a carbon dioxide concentration.

Embodiment D56 is a method of any of embodiments D47 to D55, wherein the sensor comprises a catalytic sensor capable of measuring a gas concentration, preferably one or more of an ethylene gas concentration, an oxygen concentration, or a carbon dioxide concentration. For example, the ETH1010 instrument (commercially available from Fluid Analytics LLC of Cle Elum, Wash.) is capable of measuring ethylene gas concentration associated with fresh produce via catalytic sensing.

Embodiment D5 is a method of any of embodiments D47 to D56, wherein the sensor comprises an infrared sensor. In some embodiment the infrared sensor is configured to measure infrared light reflected off the plant item (e.g., infrared light emitted by a near infrared reflectance (NIR) device and reflected from the plant item). For discussion of such sensors and sensing methods see, for example, U.S. Pat. No. 10,408,748 (Schwartzer et al.) and U.S. Pub. No. 2019/0340749 (Schwartzer et al.), each of which are incorporated by reference in its entirety.

Embodiment D58 is a method of any of embodiment D47 to D57, wherein the sensor comprises a gloss meter.

Embodiment D59 is a method of any of embodiments D47 to D58, wherein two or more, three or more, or four or more different sensor types are used to assess multiple plant characteristics associated with the plant item.

Embodiment D60 is a method of any of embodiments, D47 to D59, wherein an output of the sensor, or optionally outputs of a plurality of sensors, is provided to a processing device (e.g., a computer processor).

Embodiment D61 is a method of embodiment D60, wherein the processing device processes the output and provides a coating composition recommendation (e.g., a selection of a coating composition or a recommendation or instruction for a modification of a base coating composition). As discussed herein, such a treatment recommendation/selection may be based upon a particular treatment threshold being exceeded (e.g., without exceeding the next treatment threshold, if any are present) such that, for example, a first treatment (e.g., a first coating composition) is applied as opposed to a second treatment (e.g., a second coating composition). In other embodiments, a machine learning model receives the output of the sensors (in some examples, with other data about the plant item) and makes a treatment recommendation/selection based on the received output. In some embodiments, a machine learning model predicts an optimal coating composition based on the received output from the sensors. In some embodiments, the plant item is classified using a machine learning model with a recommended/selected treatment associated with the classification.

Embodiment D62 is a method of embodiment D61, wherein the coating composition recommendation comprises an instruction for a coating composition to be formed from multiple separate components (e.g., by combining two or more feedstock compositions in a particular ratio based on the coating composition recommendation) to, for example, vary the amount of crosslinking in the final coating and/or the level of hydrophobicity of the final coating and/or increase or decrease any other coating characteristic (e.g., any of the other coating characteristics referenced herein).

Embodiment D63 is a method of embodiment D61 or D62, wherein the coating composition recommendation comprises an instruction affecting a thickness of a coating applied on the plant item.

Embodiment D64 is a method of any of embodiments D61 to D63, wherein a plant item is coated pursuant to the coating composition recommendation.

Embodiment D65 is a method of any of embodiments D1 to D64, wherein all, or substantially all (e.g., at least 70%, at least 80%, at least 90%, at least 95%, at least 96%, at least 97%, at least 98%, at least 99%, at least 99.9%), of the exterior surfaces of the plant item are coated with the coating composition.

Embodiment D66 is a method of any of embodiments D1 to D65, wherein all, or substantially all (e.g., at least 70%, at least 80%, at least 90%, at least 95%, at least 96%, at least 97%, at least 98%, at least 99%, at least 99.9%), of the surfaces overlying or defining edible portions of the plant item are coated with the coating composition.

Embodiment D67 is a method of any of embodiments D47 to D66, wherein the one or more sensors are selected from metal-oxide gas sensor(s), electrochemical gas sensor(s), conducting/composite polymer gas sensors(s), photoacoustic gas sensor(s), piezoelectric gas sensors(s), infrared gas sensor(s), photoionization detector gas sensor(s), hyperspectral imaging sensor(s), any other sensors disclosed herein, or combinations thereof.

Embodiment D68 is a method or plant item of any of embodiments D1 to D67, wherein the coating is disposed on the plant item with an average dry coating thickness of less than about 75 microns, less than about 50 microns, less than about 20 microns, less than about 10 microns, less than about 9 microns, less than about 8 microns, less than about 7 microns, less than about 6 microns, less than about 5 microns, less than about 4 microns, less than about 3 microns, less than about 2 microns, or less than about 1.5 microns.

Embodiment D69 is a method or plant item of any of embodiments D1 to D68, wherein the coating is disposed on the plant item with an average dry coating thickness of at least about 0.01 micron, at least about 0.100 micron, at least about 0.5 micron, at least about 1 micron, at least about 1.5 microns, at least about 2 microns.

Embodiment D70 is a method or plant item of any of embodiments D1 to D69, wherein the coating is disposed on the plant item with an average dry coating thickness of about 10 nanometers (nm), about 20 nm, about 30 nm, about 40 nm, about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, 1,000 nm, about 1,100 nm, about 1,200 nm, about 1,300 nm, about 1,400 nm, about 1,500 nm, about 1,600 nm, about 1,700 nm, about 1,800 nm, about 1,900 nm, about 2,000 nm, about 2,100 nm, about 2,200 nm, about 2,300 nm, about 2,400 nm, about 2,500 nm, about 2,600 nm, about 2,700 nm, about 2,800 nm, about 2,900 nm, or about 3,000 nm, inclusive of all ranges therebetween.

Embodiment D71 is a method of any of embodiments D1 to D70, wherein the coating composition is selected or modified to include an increase in hydrophilicity (e.g., as indicated by a decrease in contact angle that deionized water exhibits with a hardened coating formed from the coating composition).

Embodiment D72 is a method of any of embodiments D1 to D71, wherein the coating composition is selected or modified to include an increase in hydrophilic material (e.g., glycerol, lipid, lecithin, sodium lauryl sulfate, an oligosaccharide, a polysaccharide, etc.).

Embodiment D73 is a method of any of embodiments D1 to D72, wherein the coating composition is selected or modified to include an increase in plasticizer.

Embodiment D74 is a method of embodiments D73, wherein the plasticizer comprises a polyol, preferably a polyol having a molar mass of less than 500 g/mol, less than 400 g/mol, less than 300 g/mol, less than 200 g/mol, or less than 100 g/mol.

Embodiment D75 is a method of embodiments D73 or D74, wherein the plasticizer comprises glycerol, a fatty acid, an oil (preferably an edible oil, more preferably an edible plant-based oil), sorbitol, propylene glycol, triethyl citrate, triacetin, polyethylene glycols (e.g., having number average molecular weights of 400 to 10,000), diethyl sebacate, dibutyl sebacate, glycol monostearate, or a mixture thereof.

Embodiment D76 is a method of any preceding embodiment, wherein the coating composition is a liquid coating composition (e.g., an aqueous coating composition) that includes at least 0.01 wt-%, at least 0.025 wt-%, at least 0.05 wt-%, at least 0.1 wt-%, at least 0.15 wt-%, at least 0.2 wt-%, at least 0.5 wt-%, at least 1 wt-%, at least 2 wt-%, at least 3 wt-%, at least 4 wt-%, at least 5 wt-%, at least 6 wt-%, at least 7 wt-%, at least 8 wt-%, or at least 9 wt-%, or at least 10 wt-% of total solids (i.e., non-volatiles).

Embodiment D77 is a method of any preceding embodiment, wherein the coating composition is a liquid coating composition (e.g., an aqueous coating composition) that includes less than 50 wt-%, less than 30 wt-%, less than 25 wt-%, less than 20 wt-%, less than 19 wt-%, less than 18 wt-%, less than 17 wt-%, less than 16 wt-%, less than 15 wt-%, less than 14 wt-%, less than 13 wt-%, less than 12 wt-%, less than 11 wt-%, less than 10 wt-%, less than 9 wt-%, less than 8 wt-%, less than 7 wt-%, less than 6 wt-%, less than 5 wt-%, less than 4 wt-%, less than 3 wt-%, less than 2.5 wt-%, or less than 2 wt-% of total solids.

Embodiment D78 is a method of any preceding embodiment, wherein the coating composition is a liquid coating composition (e.g., an aqueous coating composition) that includes from 0.1 to 35 wt-%, more typically 0.25 to 25 wt-%, and in some embodiments 0.5 to 20 wt-%, or 1 to 10 wt-% of total solids.

Aspects of the present description may also be described by the following embodiments, of which E1 to E11 and F1 to F35 may be implemented, for example, using the computing system shown in FIG. 6.

Embodiment E1 is a computer readable storage device storing data instructions that, when executed by a processing device, cause the processing device to perform operations comprising: receive an input from one or more sensors, wherein the input comprises a measurement or identification associated with a plant item to be coated (e.g., any of those previously disclosed herein such as, e.g., in any of embodiments D1 to D78, preferably an edible fruit or vegetable, more preferably a harvested edible fruit or vegetable); and generate a coating recommendation or instruction.

Embodiment E2 is a computer readable storage device of embodiment E1, wherein the instruction further causes the processing device to output the coating recommendation or instruction.

Embodiment E3 is a computer readable storage device of embodiment E1 or E2, wherein the generated recommendation or instruction comprises a modification for a base coating composition (see, e.g., any of the base coating compositions referenced in embodiment series "D" or anywhere else herein).

Embodiment E4 is a computer readable storage device of any of embodiments E1 to E3, wherein the generated recommendation or instruction relates to crosslinking of a liquid coating composition (e.g., an edible such coating composition) for coating a plant item (e.g., a fruit or vegetable).

Embodiment E5 is a computer readable storage device of any of embodiments E1 to E4, wherein the generated recommendation or instruction relates to a coating thickness of a coating to be applied to a plant item.

Embodiment E6 is a method of any of embodiment E1 to E5, wherein the generated instruction or recommendation relates to a liquid barrier coating composition to be formed from multiple separate components (e.g., by combining two or more feedstock compositions in a particular ratio based on the coating composition recommendation) to, for example, vary the amount of crosslinking in the final coating and/or the level of hydrophobicity of the final coating and/or increase or decrease any of the other coating characteristics referenced herein.

Embodiment E7 is a computer readable storage device of any of embodiments E1 to E6, wherein the generated recommendation or instruction relates to selection of a coating composition from a plurality of options (e.g., from an inventory of different coating compositions).

Embodiment E8 is a computer readable storage device of any of embodiments E1 to E7, wherein the instructions further cause the at least one processing device to identify the type of plant item to be coated.

Embodiment E9 is a computer readable storage device of any of embodiments E1 to E8, wherein the instructions further cause the at least one processing device to receive an input identifying a projected sell date or sell date range for the coated product, wherein the coating recommendation or instruction is generated based, at least in part, on the projected consumer sales date or sales date range. By way of example, an earlier projected sell date may make it feasible or desirable to use a thinner coating and/or less crosslinked coating.

Embodiment E10 is a computer readable storage device of any of embodiments E1 to E9, wherein the instructions further cause the at least one processing device to receive an input identifying a projected sell date or sell date range for the coated product, wherein the coating recommendation or instruction is generated based, at least in part, on the projected sell date or sell date range.

Embodiment E11 is a computer readable storage device of any of embodiments E10, wherein the instructions further cause the at least one processing device to receive an input identifying a desired level of ripeness or quality at sale. By way of example, customers of certain fruit markets or Asian grocery markets may desire a fruit or vegetable that is ripe on the sale date and ready for immediate consumption, whereas, in contrast, a customer at a bulk grocery market (e.g., Costco or Sam's Club) may desire a less ripe fruit or vegetable on the date of sale. By way of example, cultural differences in customers and their expectation of the level of ripeness at sale and/or when the fruit or vegetable are consumed may also be factored in.

Embodiment E12 is a computer readable storage device of any of Embodiments E1 to E11 wherein an algorithm and/or machine learning is used to generate the instruction or recommendation. For example, a machine learning can be used to generate a model which receives the input data from the one or more sensors to generate the coating recommendation or instruction.

Aspects of the present description may also be described by the following "F" embodiments, "G" embodiments, and "H embodiments".

Embodiment F1 is a coating system for coating a plant item comprising: a sensor, more typically a plurality of sensors; and a computing device including at least a processing device and including, or in communication with (e.g., via an internet connection, wired network connection, or wireless network connection), a computer readable storage device, the computing device in communication with the sensor, the computer readable storage device storing data instruction executable by the computing device to cause the computing device to: (a) determine a level of ripeness of the plant item, and (b) generate a coating instruction for the plant item.

Embodiment F2 is a coating system of embodiment F1, wherein the coating system is configured to interact with an industrial processing line for processing plant items (e.g., a fruit or vegetable processing line of a fruit or vegetable packing house).

Embodiment F3 is a coating system of embodiments F1 or F2, wherein the coating system comprises a portion of an industrial processing line for processing plant items.

Embodiment F4 is a coating system of embodiment F2 or F3, wherein the industrial processing line is an industrial processing line for processing freshly harvested produce (e.g., fruit or vegetables, including any of those referenced herein).

Embodiment F5 is a coating system of embodiment F4, wherein the industrial processing line is configured for processing one or more of: apples, avocados, asparagus, bananas, blueberries, cherries, citrus fruit (e.g., a lemon, a lime, an orange, a mandarin, or a grapefruit), cucumbers (e.g., English cucumbers), garlic, green beans, or strawberries.

Embodiment F6 is a coating system of embodiment F5, wherein the industrial processing line is configured for processing avocados.

Embodiment F7 is coating system of F2 or F3, wherein the industrial processing line is an industrial processing line configured for processing plant cuttings for rerooting and/or replanting.

Embodiment F8 is a coating system of F2 or F3, wherein the industrial processing line is configured for processing cut flowers.

Embodiment F9 is a coating system of F2 or F3, wherein the industrial processing line is configured for processing nuts (e.g., almonds, cashews, chestnuts, hazelnuts, macadamia nuts, pecans, pine nuts, pistachios, or walnuts).

Embodiment F10 is a coating system of F2 or F3, wherein the industrial processing line is configured for processing leafy greens (e.g., loose-leaf lettuce such as spring greens or spinach).

Embodiment F11 is a coating system of any of embodiments F1 to F10, wherein the coating system includes an applicator for applying a liquid barrier coating composition.

Embodiment F11' is a coating system of F11, wherein the coating system is configured such that the plant item (e.g., freshly a harvested fruit or vegetable) is rotating as the applicator applies the liquid barrier coating composition to the plant item.

Embodiment F11" is coating system of F11', wherein the coating system is configured such that the plant item is simultaneously rotating while being transported (e.g., in the direction of travel of a conveyor, typically a longitudinal direction) as the applicator applies the liquid barrier coating composition to the plant item. See, for example, WO2019/028043 (Holland et al.), which describes a conveyor apparatus for simultaneously transporting and rotating produce during coating.

Embodiment F12 is a coating system of any of embodiments F11, F11', or F11", wherein the applicator comprises a spray applicator (e.g., a spray bar, a mister bar, and/or a series of spray and/or misting devices such as nozzles, bars, or guns).

Embodiment F13 is a coating system of embodiment F12, wherein the spray applicator is configured to spray coat a fresh fruit or vegetable.

Embodiment F14 is a coating system of any of embodiments F11, F11', or F11", wherein the applicator comprises a curtain coater or wash coater.

Embodiment F15 is a coating system of any of embodiments F11, F11', or F11", wherein the applicator includes a reservoir for dipping a plant item into a liquid coating composition for purposes of coating the plant item.

Embodiment F16 is a coating system of any of embodiments F1 to F15, wherein the coating system includes a drier (e.g., for drying a liquid barrier coating composition applied to the plant item to form a hardened coating thereon). Examples of suitable driers include devices (e.g., one or more blowers and/or air knives) configured to apply a moving volume of air or other gasses (e.g., nitrogen gas and/or air and nitrogen mixtures) onto the coated plant item to facilitate removal of solvent (i.e., hardening) from the applied coating composition.

Embodiment F17 is a coating system of any of embodiments F1 to F16, wherein the sensor is configured to output (e.g., transmit) a signal carrying a value of a measurement.

Embodiment F18 is a coating system of any of embodiments F1 to F17, wherein the coating system includes a plurality of sensors.

Embodiment F19 is a coating system of embodiment F18, wherein the coating system includes two or more different types of sensors.

Embodiment F20 is a coating system of any of embodiments F1 to F19, wherein the sensor is configured to identify, measure, or both identify and measure a ripeness or quality parameter of a plant item.

Embodiment F21 is a coating system of embodiment F20, wherein the quality parameter comprises an external property of the plant item (e.g., a size, a shape, a mass, a volume, a density, an appearance, a color, the presence or absence of visual blemishes), any of the other parameters disclosed herein, and/or an internal property (e.g., composition, flavor, aroma, a concentration, etc.)

Embodiment F22 is a coating system of any of embodiments F1 to F21, wherein the sensor is configured to identify a fruit or vegetable type.

Embodiment F23 is a coating system of any of embodiments F1 to F22, wherein the sensor comprises a firmness sensor, more preferably a non-destructive firmness sensor (e.g., a sensor for measuring a level of firmness of a fruit or vegetable without damaging the fruit or vegetable).

Embodiment F24 is a coating system of embodiment F23, wherein the firmness sensor comprises an acoustical firmness sensor, an impact measurement firmness sensor, or a sensor capable of doing both. An example of a commercially available firmness sensor with both acoustical firmness and impact firmness measurement capabilities is the AFS sensor from Aweta G&P B.V. of Pinjacker, Netherlands. See also, e.g., U.S. Pat. No. 6,539,781, which discusses sensing methods and sensors for measuring the firmness of produce such as fruit via tapping of the produce.

Embodiment F25 is a coating system of any of embodiments F1 to F24, wherein the sensor is configured to provide an output indicative of an internal or external gas concentration of the plant item. See, e.g., U.S. Pat. No. 9,739,737 (Swager et. al) and U.S. Pub. No. 2016/0231267 (Swager et al.), each of which is incorporated herein by reference in its entirety, for discussion of sensors and methods for measuring the amount of ethylene gas associated with a plant item.

Embodiment F26 is a coating system of any of embodiments F1 to F25, wherein the sensor is configured to provide an output indicative of a color parameter and/or other visible characteristic of the plant item (e.g., a color parameter indicative of a level of fruit or vegetable ripeness such as, for example, a hue angle).

Embodiment F27 is a coating system of any of embodiments F1 to F26, wherein the sensor comprises an optical sensor (which may optionally be configured for hyperspectral imaging).

Embodiment F28 is a coating system of any of embodiments F27, wherein the optical sensor comprises an image acquisition device (e.g., a still and/or video camera).

Embodiment F29 is a coating system of any of embodiments F1 to F28, wherein the sensor comprises a spectrophotometer.

Embodiment F30 is a coating system of any of embodiments F1 to F29, wherein the coating system includes one or more sensors selected from metal-oxide gas sensor(s), electrochemical gas sensor(s), conducting/composite polymer gas sensors(s), photoacoustic gas sensor(s), piezoelectric gas sensors(s), infrared gas sensor(s), photoionization detector gas sensor(s), hyperspectral imaging sensor(s), any of the other sensor(s) disclosed herein, or combinations thereof.

Embodiment F31 is a coating system of any of embodiment F1 to F30, wherein the sensor is configured to measure an acid level (e.g., total acid, ascorbic acid, etc.), a sugar level (e.g., a degrees Brix, commonly abbreviated as Bx°), a ratio of sugar to acid, a level of soluble solids, a color parameter (e.g., a color intensity, a fraction of surface area that is a particular color, etc.), a visible indicator, a gas amount (e.g., an internal or emitted gas amount such as, e.g., carbon dioxide, ethylene, oxygen, or water vapor), any of the other parameters disclosed herein, or a combination thereof.

Embodiment F32 is a coating system of any of embodiments F1 to F31, wherein the coating system is configured to communicate with a user interface.

Embodiment F33 is a coating system of embodiment F32, wherein the system includes a user interface.

Embodiment F34 is a coating system of embodiment F32 or F33, wherein the user interface comprises a mobile computing device such as, e.g., a tablet (e.g., an iPad tablet) or mobile phone.

Embodiment F35 is a coating system of embodiment F32 or F33, wherein the user interface comprises a personal computer.

A non-limiting example of a representative manufacturing process for use, for example, in relation to Embodiment series D, E, F, and G in accordance with some embodiments of the present description is provided as follows: (1) Plant item unloaded onto packing line conveyor. (2) (optional) The plant item (e.g., freshly harvested fruit or vegetable) passes within region of one or more sensors that analyzes one or more characteristics of the plant item's ripeness. (3) One or more sensors transmit ripeness data for the particular plant item into the I/O interface. Examples of sensor data include acid level (e.g., total acid, ascorbic acid, etc.), a sugar level (e.g., a degrees Brix, commonly abbreviated as Bx°), a ratio of sugar to acid, a level of soluble solids, a color parameter (e.g., a color intensity, a fraction of surface area that is a particular color, etc.), a visible indicator, a gas amount (e.g., an internal or emitted gas amount such as, e.g., carbon dioxide, ethylene, oxygen, or water vapor), or a combination thereof. (4) The computing device, which can optionally reside within the enterprise, the cloud, or a hybrid enterprise/cloud determines ripeness of the particular plant item and outputs a particular coating composition recommendation, applied thickness recommendation, or combination thereof, or a recommended wash solution from a plurality of chemically different coating composition or wash solution options (e.g., a coating or wash solution composition inventory). (5) A sanitizer and optionally, a particular wash solution determined by the computing device is applied to the plant items based on the plant item's ripeness (6) (Optional) The plant item passes within region of one or more sensors that analyzes one or more characteristics of the plant's ripeness. (7) One or more sensors transmit ripeness data into the I/O interface. Examples of sensor data include acid level (e.g., total acid, ascorbic acid, etc.), a sugar level (e.g., a degrees Brix, commonly abbreviated as Bx°), a ratio of sugar to acid, a level of soluble solids, a color parameter (e.g., a color intensity, a fraction of surface area that is a particular color, etc.), a visible indicator, a gas amount (e.g., an internal or emitted gas amount such as, e.g., carbon dioxide, ethylene, oxygen, or water vapor), or a combination thereof. (8) The computing device, which can reside within the enterprise, the cloud, or a hybrid enterprise/cloud system determines ripeness and outputs a particular coating composition, applied thickness or combination thereof from a plurality of chemically different coating compositions (e.g., a coating composition inventory). (9) Plant items that are assessed to be defective and/or of an unsuitable quality grade are sorted out. (10) A particular coating composition, applied thickness, or combination thereof is determined by the computing device and is applied to the plant items based on the plant item ripeness. (11) The coating may optionally be dried on the fruit item and then packaged.

Embodiment G1 is a method of selectively applying a treatment to a plant item, the method comprising: in an industrial processing line, conveying a plant item to a treatment region (preferably a coating region, optionally a washing region); and applying a treatment (preferably a coating composition treatment, but optionally a wash treatment) to the plant item based on a property of the plant item, or one or more other plant items of a like kind (e.g., a representative sample of plant items), determined using sensor information.

Embodiment G2 is a method of embodiment G1, wherein the treatment comprises a coating composition (e.g., any of those disclosed herein).

Embodiment G3 is a method of embodiment G1 or G2, wherein the plant item comprises an edible plant item.

Embodiment G4 is a method of embodiment G3, wherein the plant item comprises a whole fruit (e.g., a climacteric fruit or a non-climacteric fruit) or a whole vegetable.

Embodiment G5 is a method of embodiments G3 or G4, wherein the plant item comprises a fruit selected from an akee, an apple, an apricot, an avocado, a banana, a blackberry, a blueberry, a carambola, a cherry, a coconut, a cranberry, a citrus fruit (e.g., a lemon, a lime, an orange, a mandarin, or a grape fruit), a cucumber (e.g., an English cucumber), a durian, an eggplant, a fig, a grape, a guava, a kiwi, a lychee, a mango, a melon (e.g., a watermelon, a cantaloupe, a honeydew, or a muskmelon), a nectarine, a *papaya*, a passionfruit, a peach, a peapod, a pear, a persimmon, a pineapple, a pepper (e.g., a bell pepper, a habanero pepper, a jalapeño pepper, a poblano pepper, or a serrano pepper), a plum, a pluot, a pomegranate, a raspberry, a strawberry, a squash (e.g., a pumpkin, an acorn squash, a butternut squash, a spaghetti squash, a yellow squash, or a zucchini), a tomato, or an uchuva; or (B) a vegetable selected from.

Embodiment G6 is a method of embodiment G3 or G4, wherein the plant item comprises a vegetable selected from asparagus, basil, beans (e.g., green beans), broccoli, Brussels sprouts, cabbage, carrots, cauliflower, celery, cilantro, corn, garlic, green onions, lettuce or other leafy greens, leeks, onions, mushrooms, parsley, potatoes, shallots, spinach, sweet potatoes, or yams.

Embodiment G7 is a method of any of embodiments G3 to G6, wherein the coating composition is applied to at least a portion of a removable skin (e.g., removable peel).

Embodiment G8 is a method of any of embodiments G3 to G6, wherein the coating composition is applied to at least a portion of an inedible skin (e.g., an avocado peel or a banana peel).

Embodiment G9 is a method of any preceding Gx embodiment, wherein the treatment is applied to the plant item via spraying, dipping, brushing, roll coating, and/or curtain coating.

Embodiment G10 is a method of any preceding Gx embodiment, wherein all, or substantially all (e.g., at least 70%, at least 80%, at least 90%, at least 95%, at least 96%, at least 97%, at least 98%, at least 99%, at least 99.9%), of the exterior surfaces of the perishable item are coated with the coating composition. In some such embodiments, all, or substantially all (e.g., at least 70%, at least 80%, at least 90%, at least 95%, at least 96%, at least 97%, at least 98%, at least 99%, at least 99.9%), of the surfaces overlying or defining edible portions of the perishable item are coated with the coating composition.

Embodiment G11 is a method of any preceding Gx embodiment, wherein the plant item is conveyed to a sensing region of the industrial processing line having one or more sensors prior to applying the treatment to the plant item, and wherein at least some of the sensor information is generated using the one or more sensors.

Embodiment G12 is a method of any preceding Gx embodiment, wherein at least some of the sensor information is generated prior to the plant item entering the industrial processing line (e.g., in a farm field prior to harvest, during harvest, after harvest of the plant item, or at a storage facility).

Embodiment G13 is a method of embodiment G12, wherein at least some of the sensor data is generated using a drone quipped with one or more sensors.

Embodiment G14 is a method of embodiment G12 or G13, wherein the sensor information is generated within at least 72 hours, within at least 48 hours, within at least 24 hours, within at least 12 hours, or within at least 6 hours of application of the treatment to the plant item in the industrial processing line.

Embodiment G15 is a method of any preceding Gx embodiment, wherein the sensor information comprises a ripeness parameter measurement.

Embodiment G16 is a method of any preceding Gx embodiment, wherein the sensor information comprises an acid level (e.g., total acid, ascorbic acid, etc.), a sugar level (e.g., Bx°), a ratio of sugar to acid, a level of soluble solids, a color parameter (e.g., a color intensity, a fraction of surface area that is a particular color, etc.), a visible indicator, a gloss level, a gas amount (e.g., an internal or emitted gas amount such as, e.g., carbon dioxide, ethylene, oxygen, or water vapor), a vitamin content, an internal color (e.g., for certain tomatoes or mangos), lycopene content (e.g., for tomatoes), a prevalence of cotyledons (e.g., for certain beans or onions), a wall thickness (e.g., for bell peppers), a starch content, any of the other sensed parameters disclosed herein, or a combination thereof.

Embodiment G17 is a method of any preceding Gx embodiment, wherein the treatment comprises a liquid coating composition, the method further comprising hardening (e.g., via drying, UV curing, and/or e-beam curing) the liquid coating composition to form a hardened coating on at least a portion of the plant item.

Embodiment G18 is a method of any preceding Gx embodiment, wherein the treatment comprises a liquid coating composition that includes at least 0.01, at least 0.05, at least 0.1, at least 0.15, at least 0.2, at least 0.25, at least 0.5, or at least 1% by weight of total solids (and optionally less than 10% by weight, or less than 5% by weight of total solids).

Embodiment G19 is a method of any preceding Gx embodiment, wherein a computing device determines the treatment to be applied based on the sensor information.

Embodiment G20 is a method of embodiment G19, wherein the computing device determines the treatment to be applied based on the sensor information obtained relative to a plurality of plants of a like kind.

Embodiment G21 is a method of embodiment G20, wherein the computing device determines an average.

Embodiment G22 is a method of any of embodiments G18 to G21, wherein the computing device selects the treatment to be applied out of a plurality of different treatments stored in containers (e.g., tanks or totes), which are preferably each in liquid communication with the treatment region of the industrial processing line.

Embodiment G23 is a method of any of embodiments G1 to G21, wherein the applied treatment is prepared, based on the sensor information, by combining two or more chemically-different parts.

Embodiment G24 is. a method of embodiment G23, wherein, based on an algorithm factoring the sensor information, the two or more chemically-different parts are combined in a particular ratio after the sensor information is generated, but prior to application to the plant item.

Embodiment G25 is a method of embodiment G23 or G24, wherein the first part includes one or both of: (i) an ingredient that is reactive with an ingredient of a second chemically-different part or (ii) an ingredient that facilitates the reaction of an ingredient in the second chemically-different part.

Embodiment G26 is a method of embodiment G25, wherein the ingredient in the first part comprises a cross-linking agent that is reactive with an ingredient of the second part having one or more active hydrogen groups.

Embodiment G27 is a method of embodiment G23 to G26, wherein one of the parts comprises a base coating composition that is modified by combining with one or more chemically-different other parts.

Embodiment G28 is a method of embodiment G27, wherein at least 70 wt-%, at least 80 wt-%, at least 90 wt-%, or at least 95 wt-% of the overall coating solids in the applied coating composition are provided by the base coating composition.

Embodiment G29 is a method of embodiment G27 or G28, wherein the base coating composition: (i) is modified to include one or more additives (e.g., any of those recited in embodiment G38) and/or (ii) is modified to include a different amount of one or more additives already present (e.g., any of those recited in embodiment G38).

Embodiment G30 is a method of any of embodiments G2 to G29, the coating composition, preferably a liquid coating composition, includes one or more ingredients having one or more active hydrogen groups; preferably one or more: carboxyl groups; hydroxyl groups; amine groups; or any other suitable active hydrogen group having a hydrogen attached to an oxygen (O), sulfur (S), or nitrogen (N) atom, e.g., as in the groups —SH, =NH, —NH$_2$, —S(=O)$_2$(OH), —S(=O)OH, or acid groups including P, O, and H such as phosphonic or phosphinic groups; salt groups thereof (e.g., base-neutralized acid groups); or any combination thereof.

Embodiment G31 is a method of any preceding Gx embodiment, wherein the coating composition, preferably a liquid coating composition, includes one or more of a lipid (preferably a mono-glyceride, a di-glyceride, a phospho-lipid, a fatty acid, a dimer fatty acid, and/or a fatty acid salt), a polysaccharide (e.g., pectin, *psyllium*, hyaluronic acid, xanthan gum, agar, carboxy methyl cellulose, alginate, carrageenan, arabinoxylan, chitosan, or dextrin), a polypeptide (e.g., gelatin, zein, globulin, albumin, whey protein, casein, hemp protein, brown rice protein, alfalfa protein, chia protein, pea protein, flax protein, or fibroin), or a combination thereof.

Embodiment G32 is a method of embodiment G31, wherein the coating composition includes one or more of a glyceride (preferably a mono-glyceride) or a silk fibroin.

Embodiment G33 is a method of embodiment G32, wherein the coating composition includes a mono-glyceride, which is preferably a mono-glyceride of a C12 to C18 fatty acid, in an amount that comprises at least 10% by weight, preferably more than 50% by weight, based on total coating solids.

Embodiment G34 is a method of embodiment G32 or G33, wherein a fatty acid portion of the glyceride includes a reactive functional group (e.g., a carbon-carbon double bond, an epoxy group, a hydroxyl group, a carboxyl group, etc.), or optionally a plurality of reactive functional groups that are the same or different.

Embodiment G35 is a method of any preceding Gx embodiment, wherein the treatment includes a saturated or unsaturated fatty acid, or a salt thereof, wherein the fatty acid optionally includes a reactive functional group other than the carboxyl group (or salt group thereof) and any carbon-carbon double bonds that may be present.

Embodiment G36 is a method of embodiment G35, wherein the other reactive functional group comprises one or more of a hydroxyl group, an epoxy group, amine group or a carboxyl group.

Embodiment G37 is a method of embodiment G32 or G33, wherein the coating composition includes one or more mono-glycerides selected from 2,3-dihydroxypropyl palmitate, 1,3-dihydroxypropan-2-yl palmitate, 2,3-dihydroxypropyl stearate, dihydroxpropan-2-yl stearate, or monolaurin.

Embodiment G38 is a method of any of embodiments G2 to G37, wherein the coating composition, preferably a liquid coating composition, includes one or more additives selected from a plasticizer, a wax, a lipid, an amino acid, a dispersing agent, an anti-microbial agent, an anti-browning or -yellowing agent (e.g., ascorbic acid or citric acid), a probiotic, a vitamin or other nutrient, an enzyme, a plant hormone or regulator, a colorant, a flavorant, an aromatic, an oxygen-scavenging agent, a compatibilizer, a leveling agent, a wetting agent, an adhesion promoter, a rheology modifier, an antifoaming agent, or a ripening inhibitor (e.g., an ethylene inhibitor and/or scavenger).

Embodiment G39 is a method of any preceding Gx embodiment, wherein the treatment does not include any ingredients derived from animals (e.g., meat, fish, fowl, animal by-products (including silk or dyes form insects), egg or egg products, milk or milk products, honey or bee products, or clarified or finished with any animal products).

Embodiment G40 is a method of any preceding Gx embodiment, wherein the treatment is eligible for certified vegan status (e.g., fully complies with the 2020 certification standards of vegan.org for use of their trademarked "Certified Vegan" logo).

Embodiment G41 is a method of any preceding Gx embodiment, wherein the treatment is not made using any ingredients from feedstocks derived from petroleum.

Embodiment G42 is a method of any preceding Gx embodiment, wherein the treatment includes one or more organic compounds, and wherein each and every one of the one or more organic compounds comprise at least about 1.5 dpm/gC (disintegrations per minute per gram carbon) of carbon-14, more preferably at least 2 dpm/gC, most preferably at least 2.5 dpm/gC, and especially at least 4 dpm/gC.

G43. The method or system of any preceding Gx embodiment, wherein the one or more sensors are selected from a firmness sensor (e.g., an acoustical firmness sensor or, an impact measurement firmness sensor), an optical sensor (which may optionally be configured for hyperspectral imaging), a spectrophotometer, a photo-acoustic sensor, a catalytic sensor, an infrared sensor, a gloss meter, an metal-oxide gas sensor, an electrochemical gas sensor, a conducting/composite polymer gas sensors, a photo-acoustic gas sensor, a piezoelectric gas sensors, a photoionization detector gas sensor.

Embodiment G44 is a method of any preceding Gx embodiment, wherein a base treatment is modified, pursuant to instructions from a computing device based on the sensor information, to change one or more coating parameters selected from: a crosslinking parameter, total coating solids, glossiness, hydrophobicity, hydrophilicity, gas permeability (e.g., permeability to carbon dioxide, oxygen, ethylene, and/or water vapor), dry film weight and/or coating thickness, crystallinity, pH, a color parameter, or any other coating parameters disclosed herein.

Embodiment G45 is a method of embodiment G44, wherein the one or more parameters is increased or decreased, relative to the base treatment, by at least 1%, increased or decreased by at least 5%, increased or decreased by at least 10%, increased or decreased by at least 15%, increased or decreased by at least 20%, increased or decreased by at least 50%, increased or decreased by at least 75%, increased or decreased by at least 90%, increased or decreased by at least 99%, increased by at least 150%, increased by at least 200%, or increased by at least 300%.

Embodiment G46 is a method of any preceding Gx embodiment, wherein the sensor information comprises a value, wherein the method further comprises with a computing device: determining when the value equals or exceeds a first threshold, the applied treatment comprises a first treatment; and when the value is less than the first threshold, the applied treatment comprises a second treatment that is different (preferably chemically different) than the first treatment. In some embodiments, a machine learning model is used to select an optimal first threshold value. In some of these embodiments, the machine learning model is trained with training data including at least one of sensor information for previous samples, historical data, and tagged data, wherein the tagged data can be automatically or manually generated.

Embodiment G47 is a method of any preceding Gx embodiment, wherein, using a computing device and optionally a predictive algorithm, the applied treatment is determined based on the sensor information and optionally one or both of: (i) a customer-defined standard for a customer or (ii) shipping parameters associated with the customer.

Embodiment G48 is a method of embodiment G47, wherein based on a determination that the plant item is likely to meet the customer-defined standard (or any other customer-related metric) upon arrival at the customer, applying a first coating to the plant item; and based on a determination that the plant item is not likely to meet the customer-defined standard (or any other customer-related metric) upon arrival at the customer, applying a second coating that is different than the first coating.

Embodiment G49 is a method of any preceding Gx embodiment, further comprising: with a computing device, determining, based on (i) the sensor information, ii) a standard for a customer, and optionally (iii) shipping parameters associated with the customer, whether the plant item is likely to meet the customer standard upon arrival at the customer; and based on a determination that the plant item is likely to meet the customer standard upon arrival at the customer, applying a first coating composition to the plant item or, alternatively, based on a determination that the plant item is not likely to meet the customer standard upon arrival at the customer, applying a second coating composition that is different than the first coating composition.

Embodiment G50 is a method of any of embodiments G46 to G49, wherein applying the first coating or applying the second coating comprises applying based on a current treatment algorithm.

Embodiment G51 is a method of any of embodiments G46 to G50, further comprising collecting feedback (e.g., from the customer after arrival of the plant item at the customer, the feedback regarding whether the plant item, as delivered, met the customer-defined standard (or any other customer-related metric) for the customer and/or from a sensor or other data collection device shipped with the treated plant items.)

Embodiment G52 is a method of embodiment G51, further comprising modifying the current treatment algorithm based on the collected feedback.

Embodiment H1 is a system comprising an industrial processing line, or one or more portions thereof, for processing live plant items, the system comprising: (a) one or more sensors for generating sensor information for conveyed live plant items (e.g., any of the sensors disclosed herein), the sensor information relating to a ripeness parameter, quality parameter, and/or other parameter of the live plant items; (b) one or more applicators for applying a liquid treatment (preferably a coating composition and/or a wash solution or other liquid pretreatment) other than water to the live plant items; (c) a computing device configured to execute instructions that, when executed, perform a method for determining, based on the sensor information, which liquid treatment to apply to the live plant items out of a plurality of potential treatment choices.

Embodiment H2 is a system of embodiment H1, wherein the treatment is a liquid coating composition.

Embodiment H3 is a system of embodiment H2, wherein the treatment is a wash solution or other liquid pretreatment.

Embodiment H is a system of any of embodiment H1 to H3, wherein the system is configured for use with a water-based treatment.

Embodiment H5 is a system of any of embodiments H1 to H3, wherein the system is configured for use with an organic-solvent-based system.

Embodiment H6 is a system of any preceding Hx embodiment, wherein the system includes a plurality of containers (e.g., tanks) in liquid communication with the one or more applicators, the containers for holding (i) treatments and/or (ii) treatment ingredients and/or intermediates.

Embodiment H7 is a system of any preceding Hx embodiment, wherein the system includes a wash portion for initially washing the live plant items that is upstream of the one or more treatment applicators.

Embodiment H8 is a system of any preceding Hx embodiment, wherein the system includes one or more transporters (e.g., any of those disclosed herein) for conveying the plant items from a sensor region including the one or more sensors to a coating region including the one or more applicators.

Embodiment H9 is a system of any preceding Hx embodiment, wherein the computing device is configured to execute instructions, which, when executed, select a treatment for application out of a plurality of preformed treatments.

Embodiment H10 is a system of any of embodiments Hx embodiment, wherein the computing device is configured to output instructions for combining two or more chemically-different parts to prepare the treatment to be applied to the live plant items.

Embodiment H12 is a system of any preceding Hx embodiment, wherein the computing device is configured to factor in a standard for a customer and optionally shipping parameters associated with the customer, and optionally whether the plant item is likely to meet the customer standard upon arrival at the customer.

Embodiment H13 is a system of embodiment H12, wherein the computing device is configured to determine whether the plant item is likely to meet the customer standard upon arrival at the customer, and apply a first coating composition to the plant item or, alternatively, based on a determination that the plant item is not likely to meet the customer standard upon arrival at the customer, apply a second coating composition that is different than the first coating composition.

While several embodiments have been described with reference to exemplary aspects, it will be understood by those skilled in the art that various changes may be made and equivalents may be substituted for elements thereof without departing from the contemplated scope. In addition, many modifications may be made to adapt a particular situation or material to the teachings provided herein without departing from the essential scope thereof. For example, in exemplary methods, steps could be removed or reordered, or other steps could be added. Sensors described herein are merely exemplary and other sensors or combinations of sensors could be employed. Therefore, it is not intended that the scope be limited to the particular aspects or embodiments disclosed; rather, the scope includes all aspects falling within the appended claims.

The complete disclosures of the patents, patent documents, and publications cited herein are incorporated by reference in their entirety as if each were individually incorporated. To the extent that there is any conflict or discrepancy between this specification as written and the disclosure in any document that is incorporated by reference herein, this specification as written will control.

The invention claimed is:

1. A method for selectively applying treatments to at least some of a batch of plant items, the method comprising:
    conveying, in an industrial processing line, at least one plant item in the batch of plant items to a sensing region having one or more sensors, wherein the batch of plant items comprises whole fruit or whole vegetables;
    assessing, with the one or more sensors and a computing device, one or more properties of the at least one plant item associated with ripeness and/or another attribute;
    conveying the at least one plant item to a treatment region;
    determining a liquid coating treatment to apply to the at least one plant item based on the assessed one or more properties, wherein the liquid coating treatment includes at least 0.1 weight percent solids and includes an active hydrogen component including a monoester of (i) a fatty acid and (ii) glycerol or ascorbic acid or a salt thereof;
    applying, in the treatment region, the liquid coating treatment to the at least one plant item; and
    hardening the liquid coating treatment to form a hardened coating.

2. The method of claim 1, wherein the at least one plant item comprises a fruit selected from an akee, an apple, an apricot, an avocado, a banana, a blackberry, a blueberry, a carambola, a cherry, a coconut, a cranberry, a citrus fruit, a cucumber, a durian, an eggplant, a fig, a grape, a guava, a kiwi, a lychee, a mango, a melon, a nectarine, a *papaya*, a passionfruit, a peach, a peapod, a pear, a persimmon, a pineapple, a pepper, a plum, a pluot, a pomegranate, a raspberry, a strawberry, a squash, a tomato, or an uchuva.

3. The method of claim 1, wherein assessing one or more properties of the at least one plant item further comprises selecting a representative sample of plant items from the batch of plant items, and assessing one or more properties associated with ripeness and/or another attribute for each plant item in the representative sample of plant items;
    wherein determining the treatment is further based on the assessed one or more properties for each of the sampled plant items; and
    wherein the treatment is applied to the batch of plant items.

4. The method of claim 1, wherein the one or more properties comprise an acid level, a sugar level, a ratio of sugar to acid, a level of soluble solids, a color parameter, a visible indicator, a gloss level, a gas identity, a gas amount, a vitamin content, an internal color, lycopene content, a prevalence of cotyledons, a wall thickness, a starch content, a microbial parameter, a firmness amount, a reflected sound, or a combination thereof.

5. The method of claim 1, wherein the liquid coating treatment comprises a base coating composition that is modified prior to application, based on the one or more properties, to change one or more coating parameters selected from: a crosslinking parameter, total coating solids, glossiness, hydrophobicity, hydrophilicity, surface tension, gas permeability, dry film weight and/or coating thickness, crystallinity, pH, an antimicrobial property, a color parameter, or a presence or concentration of a ripening inhibitor.

6. The method of claim 1, wherein the active hydrogen component includes a polypeptide.

7. The method of claim 1, wherein the one or more sensors are selected from a firmness sensor, an optical sensor, a spectrophotometer, a photo-acoustic sensor, a catalytic sensor, an infrared sensor, a gloss meter, an metal-oxide gas sensor, an electrochemical gas sensor, a conducting/composite polymer gas sensor, a photo-acoustic gas sensor, a piezoelectric gas sensor, a photoionization detector gas sensor, or a sensor configured for ultrasound imaging.

8. The method of claim 1, wherein the one or more sensors include a sensor configured for hyperspectral imaging.

9. The method of claim 1, wherein the method includes accessing two or more different properties associated with ripeness and/or another attribute of the at least one plant item.

10. The method of claim 1, wherein applying the treatment comprises spraying, dipping, brushing or curtain coating the at least one plant item.

11. The method of claim 1, wherein the treatment is determined from a plurality of treatments including at least a first treatment or a second treatment.

12. The method of claim 11, wherein the first treatment and the second treatment are each stored in separate containers that are in liquid communication with one or more dispensers in the treatment region of the industrial processing line.

13. The method of claim 11, wherein the treatment is determined by:
    determining whether the assessed one or more properties exceeds a threshold, wherein the first treatment is applied when the assessed one or more properties exceeds the threshold and the second treatment is applied when the assessed one or more properties are equal to or less than the threshold.

14. The method of claim 13, wherein the threshold comprises a prediction of ripeness and/or another attribute at a time of delivery that is based on (i) a customer-defined standard for a customer; and/or (ii) shipping parameters associated with the customer.

15. The method of claim 14, wherein determining whether to apply the first treatment comprising a first coating composition or the second treatment comprising a second coating composition further comprises:
    using customer feedback for a previously treated batch of plant items received by the customer to determine whether to apply the first treatment or the second treatment, the customer feedback including whether a delivered set of treated plant items met the customer-defined standard.

16. The method of claim 1, wherein assessing the one or more properties of the at least one plant item further comprises:
    providing data collected by the one or more sensors to a machine learning model trained to detect properties of plant items.

17. The method of claim 16, wherein the determining the treatment is further based on a prediction output by the machine learning model.

18. The method of claim 1, wherein:
the at least one plant item comprises at least one avocado; and
the assessed one or more properties include a property associated with ripeness.

19. The method of claim 18, wherein the liquid coating treatment is determined from a plurality of treatments including at least a first treatment or a second treatment, and wherein the first treatment and the second treatment are each stored in separate containers that are in liquid communication with one or more dispensers in the treatment region of the industrial processing line.

20. The method of claim 18, wherein the liquid coating treatment is prepared by combining a base coating composition with one or more chemically-different other parts, wherein the base composition is a base coating composition that is modified, based on the one or more properties, to change one or more coating parameters selected from: a crosslinking parameter, total coating solids, glossiness, hydrophobicity, hydrophilicity, surface tension, gas permeability, dry film weight and/or coating thickness, crystallinity, pH, an antimicrobial property, or a color parameter.

21. The method of claim 18, wherein the one or more properties comprise an acid level, a sugar level, a ratio of sugar to acid, a level of soluble solids, a color parameter, a visible indicator, a gloss level, a gas identity, a gas amount, a vitamin content, an internal color, lycopene content, a prevalence of cotyledons, a wall thickness, a starch content, a microbial parameter, a firmness amount, a reflected sound, or a combination thereof.

22. The method of claim 18, wherein assessing the one or more properties of the at least one avocado further comprises:
providing data collected by the one or more sensors to a machine learning model trained to detect properties of avocados;
wherein the determining the treatment is further based on a prediction output by the machine learning model.

23. The method of claim 1, wherein the determining the treatment is further based on one or both of: (i) a customer-defined standard for a customer or (ii) shipping parameters associated with a customer.

24. The method of claim 1, wherein the method further includes:
making a supply chain decision to change a customer and/or customer delivery location for the at least one plant item.

25. The method of claim 1, further comprising:
optionally packaging the at least one treated plant item; and
based on the assessed one or more properties, providing a temporal indication of ripeness for the at least one treated plant item that is printed on the packaging for the at least one plant item or otherwise associated with the packaging or the at least one plant item.

26. The method of claim 1, wherein the computing device is at least one computing device, and wherein determining the liquid coating treatment to apply to the at least one plant item based on the assessed one or more properties is performed by the at least one computing device.

27. The method of claim 1, wherein the computing device is at least one computing device, and wherein determining the liquid coating treatment to apply further comprises providing a coating recommendation based on the determined liquid coating treatment.

* * * * *